US007084121B2

(12) United States Patent
Ekwuribe et al.

(10) Patent No.: US 7,084,121 B2
(45) **Date of Patent: *Aug. 1, 2006**

(54) MIXTURES OF CALCITONIN DRUG-OLIGOMER CONJUGATES COMPRISING POLYALKYLENE GLYCOL, USES THEREOF, AND METHODS OF MAKING SAME

(75) Inventors: Nnochiri N. Ekwuribe, Cary, NC (US); Christopher H. Price, Chapel Hill, NC (US); Aslam M. Ansari, Rockville, MD (US); Amy L. Odenbaugh, Morrisville, NC (US)

(73) Assignee: Nobex Corporation, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/806,523

(22) Filed: Mar. 23, 2004

(65) Prior Publication Data

US 2004/0180831 A1 Sep. 16, 2004

Related U.S. Application Data

(63) Continuation of application No. 09/873,777, filed on Jun. 4, 2001, now Pat. No. 6,713,452.

(51) Int. Cl.
*A61K 38/23* (2006.01)
*C07K 14/585* (2006.01)

(52) U.S. Cl. .......................... 514/21; 514/12; 530/307

(58) Field of Classification Search ................ 530/307, 530/345, 410; 514/2, 11, 12, 21; 528/425; 554/227; 562/587; 568/613, 618, 622, 623
See application file for complete search history.

(56) References Cited

U.S. PATENT DOCUMENTS

| | | | | |
|---|---|---|---|---|
| 3,256,153 | A | 6/1966 | Heimlech | 424/497 |
| 3,868,356 | A | 2/1975 | Smyth | 530/303 |
| 3,919,411 | A | 11/1975 | Glass et al. | 424/78.27 |
| 3,950,517 | A | 4/1976 | Lindsay et al. | 514/3 |
| 4,003,792 | A | 1/1977 | Mill et al. | 530/303 |
| 4,044,196 | A | 8/1977 | Huper et al. | 526/271 |
| 4,087,390 | A | 5/1978 | Shields | 525/54.11 |
| 4,093,574 | A | 6/1978 | Shields | 525/54.11 |
| 4,100,117 | A | 7/1978 | Shields | 525/54.11 |
| 4,179,337 | A | 12/1979 | Davis et al. | 435/181 |
| 4,223,163 | A | 9/1980 | Guilloty | 568/618 |
| 4,229,438 | A | 10/1980 | Fujino et al. | 514/15 |
| 4,253,998 | A | 3/1981 | Sarantakis | 525/54.11 |
| 4,277,394 | A | 7/1981 | Fujino et al. | 536/330 |
| 4,338,306 | A | 7/1982 | Kitao et al. | 514/4 |
| 4,348,387 | A | 9/1982 | Brownlee et al. | 514/4 |
| 4,410,547 | A | 10/1983 | Ueno et al. | 514/557 |
| 4,469,681 | A | 9/1984 | Brownlee et al. | 514/4 |
| 4,472,382 | A | 9/1984 | Labrie et al. | 514/15 |
| 4,554,101 | A | 11/1985 | Hopp | 514/2 |
| 4,579,730 | A | 4/1986 | Kidron et al. | 514/3 |
| 4,585,754 | A | 4/1986 | Meisner et al. | 514/8 |
| 4,662,392 | A | 5/1987 | Vadasz | 137/533.11 |
| 4,684,524 | A | 8/1987 | Eckenhoff et al. | 424/469 |
| 4,698,264 | A | 10/1987 | Steinke | 428/402.2 |
| 4,717,566 | A | 1/1988 | Eckenhoff et al. | 424/438 |
| 4,772,471 | A | 9/1988 | Vanlerberghe et al. | 424/450 |
| 4,774,976 | A | 10/1988 | Janecke et al. | 137/14 |
| 4,797,288 | A | 1/1989 | Sharma et al. | 424/47.6 |
| 4,801,575 | A | 1/1989 | Pardridge | 514/4 |
| 4,839,341 | A | 6/1989 | Massey et al. | 514/4 |
| 4,840,799 | A | 6/1989 | Appelgren et al. | 424/493 |
| 4,849,405 | A | 7/1989 | Ecanow | 514/3 |
| 4,917,888 | A | 4/1990 | Katre et al. | 424/85.91 |
| 4,935,246 | A | 6/1990 | Ahrens | 424/490 |
| 4,946,828 | A | 8/1990 | Markussen | 514/3 |
| 4,957,910 | A | 9/1990 | Sutton et al. | 514/182 |
| 4,963,367 | A | 10/1990 | Ecanow | 424/485 |
| 4,963,526 | A | 10/1990 | Ecanow | 514/3 |
| 4,994,439 | A | 2/1991 | Longenecker et al. | 514/3 |
| 5,013,556 | A | 5/1991 | Woodle et al. | 424/450 |
| 5,055,300 | A | 10/1991 | Gupta | 424/409 |
| 5,055,304 | A | 10/1991 | Makino et al. | 424/465 |
| 5,089,261 | A | 2/1992 | Nitecki et al. | 424/85.2 |
| 5,093,198 | A | 3/1992 | Speaker et al. | 428/402.21 |
| 5,099,074 | A | 3/1992 | Mueller et al. | 568/617 |
| 5,122,614 | A | 6/1992 | Zalipsky | 548/520 |
| 5,157,021 | A | 10/1992 | Balschmidt et al. | 514/3 |
| 5,162,430 | A | 11/1992 | Rhee et al. | 525/54.1 |
| 5,164,366 | A | 11/1992 | Balschmidt et al. | 514/3 |
| 5,202,415 | A | 4/1993 | Jonassen et al. | 530/303 |
| 5,206,219 | A | 4/1993 | Desai | 514/3 |
| 5,283,236 | A | 2/1994 | Chiou | 514/2 |
| 5,286,637 | A | 2/1994 | Veronese et al. | 435/183 |
| 5,292,802 | A | 3/1994 | Rhee et al. | 525/54.1 |

(Continued)

FOREIGN PATENT DOCUMENTS

DE 196 32 440 A1 2/1998

(Continued)

OTHER PUBLICATIONS

Banting et al., "Pancreatic Extracts in the Treatment of Diabetes Mellitus," *Can. Med. Assoc. J.*, 12: 141-146 (1922).

(Continued)

*Primary Examiner*—Jeffrey Edwin Russel
(74) *Attorney, Agent, or Firm*—William A. Barrett; Moore & Van Allen PLLC

(57) ABSTRACT

A mixture of conjugates in which each conjugate in the mixture comprises a calcitonin drug coupled to an oligomer that includes a polyalkylene glycol moiety is disclosed. The mixture may lower serum calcium levels in a subject by 10, 15 or even 20 percent or more. Moreover, the mixture may be more effective at surviving an in vitro model of intestinal digestion than non-conjugated calcitonin. Furthermore, the mixture may exhibit a higher bioavailability than non-conjugated calcitonin.

15 Claims, 18 Drawing Sheets

U.S. PATENT DOCUMENTS

| | | | | |
|---|---|---|---|---|
| 5,298,410 | A | 3/1994 | Phillips et al. | 435/188 |
| 5,304,473 | A | 4/1994 | Belagaje et al. | 435/69.7 |
| 5,308,889 | A | 5/1994 | Rhee et al. | 523/113 |
| 5,312,808 | A | 5/1994 | Shorr et al. | 514/6 |
| 5,320,840 | A | 6/1994 | Camble et al. | 424/85.1 |
| 5,324,775 | A | 6/1994 | Rhee et al. | 525/54.2 |
| 5,328,955 | A | 7/1994 | Rhee et al. | 525/54.1 |
| 5,349,052 | A | 9/1994 | Delgado et al. | 530/351 |
| 5,359,030 | A | 10/1994 | Ekwuribe | 530/303 |
| 5,405,621 | A | 4/1995 | Sipos | 424/490 |
| 5,405,877 | A | 4/1995 | Greenwald et al. | 514/772.3 |
| 5,413,791 | A | 5/1995 | Rhee et al. | 424/422 |
| 5,415,872 | A | 5/1995 | Sipos | 424/490 |
| 5,428,128 | A | 6/1995 | Mensi-Fattohi et al. | 530/302 |
| 5,438,040 | A | 8/1995 | Ekwuribe | 514/8 |
| 5,444,041 | A | 8/1995 | Owen et al. | 514/2 |
| 5,446,091 | A | 8/1995 | Rhee et al. | 525/54.1 |
| 5,457,066 | A | 10/1995 | Frank et al. | 435/68.1 |
| 5,461,031 | A | 10/1995 | De Felippis | 514/4 |
| 5,468,478 | A | 11/1995 | Saifer et al. | 424/78.27 |
| 5,504,188 | A | 4/1996 | Baker et al. | 530/304 |
| 5,506,203 | A | 4/1996 | Backstrom et al. | 514/4 |
| 5,518,998 | A | 5/1996 | Backstrom et al. | 514/3 |
| 5,523,348 | A | 6/1996 | Rhee et al. | 525/54.1 |
| 5,529,915 | A | 6/1996 | Phillips et al. | 435/188 |
| 5,545,618 | A | 8/1996 | Buckley et al. | 514/12 |
| 5,550,188 | A | 8/1996 | Rhee et al. | 525/54.1 |
| 5,567,422 | A | 10/1996 | Greenwald | 424/78.3 |
| 5,597,797 | A | 1/1997 | Clark | 514/12 |
| 5,606,038 | A | 2/1997 | Regen | 536/6.5 |
| 5,612,460 | A | 3/1997 | Zalipsky | 530/391.9 |
| 5,631,347 | A | 5/1997 | Baker et al. | 530/303 |
| 5,637,749 | A | 6/1997 | Greenwald | 558/6 |
| 5,643,575 | A | 7/1997 | Martinez et al. | 424/194.1 |
| 5,646,242 | A | 7/1997 | Baker et al. | 530/303 |
| 5,650,388 | A | 7/1997 | Shorr et al. | 514/6 |
| 5,658,878 | A | 8/1997 | Backstrom et al. | 514/3 |
| 5,681,567 | A | 10/1997 | Martinez et al. | 424/178.1 |
| 5,681,811 | A | 10/1997 | Ekwuribe | 514/8 |
| 5,693,609 | A | 12/1997 | Baker et al. | 514/3 |
| 5,693,769 | A | 12/1997 | Kahne et al. | 536/5 |
| 5,700,904 | A | 12/1997 | Baker et al. | 530/305 |
| 5,707,648 | A | 1/1998 | Yiv | 424/450 |
| 5,714,639 | A | 2/1998 | Bowman et al. | 568/620 |
| 5,738,846 | A | 4/1998 | Greenwald et al. | 424/85.7 |
| 5,747,445 | A | 5/1998 | Backstrom et al. | 514/4 |
| 5,747,642 | A | 5/1998 | De Felippis | 530/304 |
| 5,750,497 | A | 5/1998 | Havelund et al. | 514/3 |
| 5,763,396 | A | 6/1998 | Weiner et al. | 514/3 |
| 5,766,620 | A | 6/1998 | Heiber et al. | 424/436 |
| 5,824,638 | A | 10/1998 | Burnside et al. | 514/3 |
| 5,830,853 | A | 11/1998 | Backstrom et al. | 514/4 |
| 5,830,918 | A | 11/1998 | Sportsman et al. | 514/648 |
| 5,843,866 | A | 12/1998 | Parker et al. | 504/116 |
| 5,849,860 | A | 12/1998 | Hakimi et al. | 528/370 |
| 5,853,748 | A | 12/1998 | New | 424/450 |
| 5,854,208 | A | 12/1998 | Jones et al. | 514/3 |
| 5,856,451 | A | 1/1999 | Olsen et al. | 530/402 |
| 5,866,538 | A | 2/1999 | Norup et al. | 514/3 |
| 5,866,584 | A | 2/1999 | Cincotta et al. | 514/288 |
| 5,874,111 | A | 2/1999 | Maitra et al. | 424/499 |
| 5,898,028 | A | 4/1999 | Jensen et al. | 514/4 |
| 5,902,588 | A | 5/1999 | Greenwald et al. | 424/278.1 |
| 5,905,140 | A | 5/1999 | Hansen | 530/303 |
| 5,907,030 | A | 5/1999 | Shen et al. | 530/331 |
| 5,922,675 | A | 7/1999 | Baker et al. | 514/4 |
| 5,932,462 | A | 8/1999 | Harris et al. | 435/188 |
| 5,942,248 | A | 8/1999 | Barnwell | 424/457 |
| 5,948,751 | A | 9/1999 | Kimer et al. | 514/4 |
| 5,952,008 | A | 9/1999 | Backstrom et al. | 424/499 |
| 5,952,297 | A | 9/1999 | De Felippis et al. | 514/3 |
| 5,962,267 | A | 10/1999 | Shin et al. | 435/69.4 |
| 5,968,549 | A | 10/1999 | New et al. | 424/450 |
| 5,969,040 | A | 10/1999 | Hallahan et al. | 525/54.1 |
| 5,981,709 | A | 11/1999 | Greenwald et al. | 530/351 |
| 5,985,263 | A | 11/1999 | Lee et al. | 424/85.2 |
| 6,004,574 | A | 12/1999 | Backstrom et al. | 424/434 |
| 6,011,008 | A | 1/2000 | Domb et al. | 514/8 |
| 6,025,325 | A | 2/2000 | Campfield et al. | 514/2 |
| 6,034,054 | A | 3/2000 | DeFelippis et al. | 514/4 |
| 6,042,822 | A | 3/2000 | Gilbert et al. | 424/85.7 |
| 6,043,214 | A | 3/2000 | Jensen et al. | 514/3 |
| 6,051,551 | A | 4/2000 | Hughes et al. | 514/3 |
| 6,057,292 | A | 5/2000 | Cunningham et al. | 514/12 |
| 6,063,761 | A | 5/2000 | Jones et al. | 514/3 |
| 6,093,391 | A | 7/2000 | Kabanov et al. | 424/85.1 |
| 6,113,906 | A | 9/2000 | Greenwald et al. | 424/194.1 |
| 6,165,976 | A | 12/2000 | Backstrom et al. | 514/3 |
| 6,177,087 | B1 | 1/2001 | Greenwald et al. | 424/278.1 |
| 6,191,105 | B1 | 2/2001 | Ekwuribe et al. | 514/3 |
| 6,200,602 | B1 | 3/2001 | Watts et al. | 424/463 |
| 6,211,144 | B1 | 4/2001 | Havelund | 514/4 |
| 6,248,363 | B1 | 6/2001 | Patel et al. | 424/497 |
| 6,251,856 | B1 | 6/2001 | Markussen et al. | 514/3 |
| 6,258,377 | B1 | 7/2001 | New et al. | 424/450 |
| 6,268,335 | B1 | 7/2001 | Brader | 514/3 |
| 6,306,440 | B1 | 10/2001 | Backstrom et al. | 424/499 |
| 6,309,633 | B1 | 10/2001 | Ekwuribe et al. | 424/85.1 |
| 6,310,038 | B1 | 10/2001 | Havelund | 514/4 |
| 6,323,311 | B1 | 11/2001 | Liu et al. | 530/303 |
| 6,335,316 | B1 | 1/2002 | Hughes et al. | 514/3 |
| 6,342,225 | B1 | 1/2002 | Jones et al. | 424/193.1 |
| 6,506,730 | B1 | 1/2003 | Lee et al. | |
| 6,713,452 | B1* | 3/2004 | Ekwuribe et al. | 514/21 |
| 6,770,625 | B1* | 8/2004 | Soltero et al. | 514/12 |
| 6,835,802 | B1* | 12/2004 | Ekwuribe et al. | 528/425 |
| 2002/0160938 | A1 | 10/2002 | Brandenburg et al. | 514/3 |
| 2003/0004304 | A1 | 1/2003 | Ekwuribe et al. | 528/425 |
| 2003/0027748 | A1 | 2/2003 | Ekwuribe et al. | 514/3 |
| 2003/0027995 | A1 | 2/2003 | Ekwuribe et al. | 514/399 |
| 2003/0050228 | A1 | 3/2003 | Ekwuribe et al. | 514/3 |
| 2003/0069170 | A1 | 4/2003 | Soltero et al. | 514/2 |
| 2003/0083232 | A1 | 5/2003 | Soltero et al. | 514/3 |
| 2003/0087808 | A1 | 5/2003 | Soltero et al. | 514/3 |
| 2003/0144468 | A1 | 7/2003 | Ekwuribe et al. | 528/425 |

FOREIGN PATENT DOCUMENTS

| | | |
|---|---|---|
| EP | 0 031 567 | 7/1981 |
| EP | 0483465 B1 | 5/1992 |
| EP | 0 511 903 A2 | 11/1992 |
| EP | 0 483 465 | 8/1995 |
| EP | 0 597 007 | 10/1996 |
| EP | 0 621 777 | 11/1996 |
| EP | 0797615 B1 | 1/1997 |
| EP | 0 822 218 A2 | 2/1998 |
| GB | 1 492 997 | 11/1977 |
| JP | 01207320 | 8/1989 |
| JP | 1 254 699 | 10/1989 |
| WO | WO93/01802 | 2/1993 |
| WO | WO95/09831 | 4/1995 |
| WO | WO95/30641 | 11/1995 |
| WO | WO97/14740 | 4/1997 |
| WO | WO98/07745 | 2/1998 |
| WO | WO99/32134 | 7/1999 |
| WO | WO99/65941 | 12/1999 |
| WO | WO 01/12230 | 2/2001 |

OTHER PUBLICATIONS

H. Allcock & F. Lampe, "Contemporary Polymer Chemistry," 394-403 (2nd. ed., 1991).

Y. Chen & G. Baker, "Synthesis and Properties of AMA Amphiphiles," *J. Org. Chem.*, 64: 6870-6873 (1999).

"Pharmaceutical Research: Official Journal of the American Association of Pharmaceutical Scientists," 3(6): 318-326 (1986).

Coudert et al., "A Novel, Unequivocal Synthesis of Polyethylene Glycols," *Synthetic Communications*, 16(1): 19-26 (1986).

J. Milton Harris, "Laboratory Synthesis of Polyethylene Glycol Derivatives," *J. Macromol. Science—Rev. Macromol. Chem. Phys.*, C25(3): 325-373 (1985).

International Search Report corresponding to PCT/US02/17575; Date of Mailing: Sep. 25, 2002.

Francis, G.E., et al., *Polyethylene Glycol Modification: Relevance of Improved Methodology to Tumour Targeting*, Journal of Drug Targeting, vol. 3, pp. 321-340 (1996).

Guzman, Angel, et al., *Effects of Fatty Ethers and Stearic Acid of the Gastrointestinal Absorption of Insulin*, PRHSJ, vol. 9, No. 2, pp. 155-159 (Aug. 1990).

Krishnan, B. Radha, et al., *Stability and Physical Characteristics of Orally Active Amphiphilic Human Insulin Analog, Methoxy (Polyethylene Glycol) Hexanoyl Human Recombinant Insulin ( HIM2), Proceed. Int'l. Symp. Control. Rel. Bioact. Mater.*, vol. 27 pp. 1038-1039 (2000).

Lindsay, D.G., et al., *The Acetylation of Insulin, Biochem J.*, vol. 121, pp. 737-745 (1971).

Mesiha, M.S., et al., *Hypoglycaemic effect of oral insulin preparations containing Brij 35, 52, 58 or 92 and stearic acid, J. Pharm. Pharmacol.*, vol. 33, pp. 733-734 (1981).

Moghaddam, Amir, *Use of polyethylene glycol polymers for bioconjugations and drug development, American Biotechnology Laboratory*, pp. 42, 44 (Jul. 2001).

Neubauer, H. Paul, et al., *Influence of Polyethylene Glycol Insulin on Lipid Tissues of Experimental Animals, Diabetes*, vol. 32, pp. 953-958 (Oct. 1983).

Shen, Wei-Chiang, et al., *(C) Means to Enhance Penetration; (3) Enhancement of polypeptide and protein absorption by macromolecular carriers via endocytosis and transcytosis, Advanced Drug Delivery Reviews*, vol. 8, pp. 93-113 (1992).

Sirokman, Geza, et al., *Refolding and proton pumping activity of a polyethylene glycol-bacteriohodopsin water-soluble conjugate, Protein Science*, vol. 2, pp. 1161-1170 (1993).

Torchilin, Vladimir P., *Immunoliposomes and PEGylated Immunoliposomes: Possible Use for Targeted Delivery of Imaging Agents, Immunomethods*, vol. 4, pp. 244-258 (1994).

Wei, Jiang, et al., *A Poly(Ethylene Glycol) Water-soluble Conjugate of Porin: Refolding to the Native State, Biochemistry*, vol. 34, pp. 6408-6415 (1995).

Xia, Jiding, et al., *Effects of polyoxyethylene chain length distribution on the interfacial properties of polyethylene glycol n-dodecyl ether, Yingyong Huaxue*, vol. 2, No. 4, pp. 59-65 (Abstract Only) (1985).

Zalipsky, Samuel, et al., *Peptide Attachment to Extremities of Liposomal Surface Grafted PEC Chains: Preparation of the Long-Circulating Form of Laminin Pentapeptide, YIGSR, Bioconjugate Chem.*, vol. 6, pp. 705-708 (1995).

Still et al., *Methods of Reducing Hypoglycemic Episodes in the Treatment of Diabetes Mellitus*, U.S. Appl. No. 10/461,199, filed Jun. 13, 2003.

Radhakrishnan et al., *Insulin Polypeptide-Oligomer Conjugates, Proinsulin Polypeptide-Oligomer Conjugates and Methods of Synthesizing Same*, U.S. Appl. No. 10/389,499, filed Mar. 17, 2003.

Soltero et al., *Pharmaceutical Compositions of Insulin Drug-Oligomer Conjugates and Methods of Treating Diseases Therewith*, U.S. Appl. No. 10/382,155, filed Mar. 5, 2003.

Soltero et al., *Pharmaceutical Compositions of Drug-Oligomer Conjugates and Methods of Treating Diseases Therewith*, U.S. Appl. No. 10/382,069, filed Mar. 5, 2003.

Soltero et al., *Insulin Polypeptide-Oligomer Conjugates, Proinsulin Polypeptide-Oligomer Conjugates and Methods of Synthesizing Same*, U.S. Appl. No. 10/382,022, filed Mar. 5, 2003.

Ekwuribe et al., *Calcitonin Drug-Oligomer Conjugates, and Uses Thereof*, U.S. Appl. No. 10/166,355, filed Nov. 8, 2002, including Preliminary Amendment dated Feb. 26, 2003 and Supplemental Preliminary Amendment dated Mar. 31, 2003.

Ekwuribe et al., *Mixtures of Drug-Oligomer Conjugates Comprising Polyalkylene Glycol, Uses Thereof, and Methods of Making Same*, U.S. Appl. No. 09/743,797, filed Jun. 4, 2001.

Ekwuribe et al., *Hydrophilic and Lipophilic Balanced Microemulsion Formulations of Free-Form and/or Conjugation-Stabilized Therapeutic Agents Such as Insulin*, U.S. Appl. No. 09/614,203, filed Jul. 12, 2000.

Hinds et al., *Synthesis and Characterization of Poly9ethylene glycol)-insulin*, Bioconjugate Chem., vol. 11, 2000, pp. 195-201.

Ekwuribe et al., *Amphiphilic Prodrugs*, U.S. Appl. No. 09/474, 915, filed Dec. 31, 1999.

Abuchowski, A. and F. F. Davis "Soluble Polymer-Enzyme Adducts" pp. 367-383, *Enzymes as Drugs*, Ed. J. S. Holcenberg, John Wiley (1981).

Agarwal et al. "Polymethyacrylate-based Microparticulates of Insulin for Oral Delivery: Preparation and In Vitro Dissolution Stability in the Presence of Enzyme Inhibitors" *International Journal of Pharmaceutics* 225:31-39 (2001).

Akiyama et al. "The Synthesis of New Derivatives of 1-β-D-Arabinofuranosylcytosine" *Chem. Pharm. Bull.* 26(3):981-984 (1978).

Allaudeen et al. "Orally Active Insulin: A Single Insulin Conjugate Selected for Future Studies" 60th Annual Meeting of the American Diabetes Assoc., Atlanta, GA, Jun. 2000 (Abstract).

Anderson et al. "HIM2, a Novel Modified Insulin, has Improved Systemic Pharmacokinetics in Normal Dogs, Compared to Unmodified Insulin" American Diabetes Association 62nd Annual Meeting, Jun. 2002 (Abstract).

Ansell et al. "Application of Oligo-(14-amino-3,6,9,12-tetraoxatetradecanoic acid) Lipid Conjugates as Steric Barrier Molecules in Liposomal Formulations" *Bioconjugate Chem.* 10:653-666 (1999).

Aoshima et al. "$N^4$-Behenoyl-1- β-D-Arabinofuranosylcytosine as a Potential New Antitumor Agent" *Cancer Research* 37:2481-2486 (1977).

Baker, D. C. et al. "Prodrugs of 9-β-D-Arabinofuranosyladenine. 1. Synthesis and Evaluation of Some 5'-(O-Acyl) Derivatives" *J. Med. Chem.* 21(12):1218-1221 (1978).

Banting et al. "Pancreatic Extracts in the Treatment of Diabetes Mellitus: Preliminary Report" *Can. Med. Assoc. J.* 145(10):1281-1286 (1991).

Baudys et al. "Stabilization and Instestinal Absorption of Human Calcitonin" *J. Contr. Rel.* 39:145-51 (1996).

Baudys et al. "Synthesis and Characterization of Different Glycosylated Derivatives of Insulin" *Proceed Interr. Symp. Cont. Rel. Bioactive. Mater.* 19:210-211 (1992).

Block, Lawrence H. "Pharmaceutical Emulsions and Microemulsions" *Pharmaceutical Dosage Forms: Disperse Systems* vol. 2, Ed. Lieberman et al., pp. 47-109 (1996).

Boccu et al. "Pharmacokinetic Properties of Polyethylene Glycol Derivatized Superoxide Dismutase" *Pharm. Res. Comm.* 14:113-120 (1982).

Bone et al. "Successful Treatment of an Insulin Dependent Rat Model of Human Type I Diabetes with Orally Active Insulin" Program and Abstracts, 4th International Workshop on Lessons from Animal Diabetes, Omiya, Japan, Nov. 1994 (Abstract).

Bone et al. "Successful Treatment of Type I Diabetes with Orally-Active Insulin: Studies in The Insulin Dependent BB/S Rat" Program and Abstracts, 55th Annual Meeting of the American Diabetes Association, Atlanta Georgia, Jun. 1995 (Abstract).

Brange and Volund "Insulin Analogs with Improved Pharmacokinetic Profiles" *Advanced Drug Delivery Reviews* 35:307-335 (1999).

Brange et al. "Chemical Stability of Insulin. 1. Hydrolytic Degradation During Storage of Pharmaceutical Preparations" *Pharm. Res.* 9(6):715-726 (1992).

Brange et al. "Chemical Stability of Insulin. 2. Formation of Higher Molecular Weight Transformation Product During Storage of Pharmaceutical Preparations" *Pharm. Res.* 9(6):727-734 (1992).

Brange, J. "Galenics of Insulin: The Physico-Chemical and Pharmaceutical Aspects of Insulin and Insulin Preparations" Novo Research Institute, Denmark, pp. 18-100 (1987).

Chien, Y. W., Novel Drug Delivery Systems, pp. 678-679, Marcell Deffer, Inc., New York, N.Y. (1992).

Cleland et al. "Emerging Protein Delivery Methods" *Current Opinion in Biotechnology* 12:212-219 (2001).

Clement et al. "Effects of Multiple Doses of Orally Administered Hexyl Insulin M2 (HIM2) on Postprandial Blood Glucose (PPG) Concentrations in Type 1 Diabetic (T1) Patients" American Diabetes Association 62nd Annual Meeting, Jun. 2002 (Poster).

Clement et al. "Oral Insulin Product Hexyl-Insulin Monoconjugate 2 (HIM2) in Type 1 Diabetes Mellitus: The Glucose Stabilization Effects of HIM2" *Diabetes Technology & Therapeutics* 4(4):459-466 (2002).

Clement, Stephen "A Dose-Escalation Study of the Effects of Two Sequential Doses of Oral Modified Insulin on Blood Glucose Concentrations in Patients with Type 1 Diabetes Mellitus" American Diabetes Association Annual Meeting (Jun. 25, 2001) (Abstract).

Clement, Stephen "A Dose-Escalation Study of the Effects of Two Sequential Doses of Oral Modified Insulin on Blood Glucose Concentrations in Patients with Type 1 Diabetes Mellitus" American Diabetes Association Annual Meeting (Jun. 25, 2001) (Poster).

Conradi et al. "The Influence of Peptide Structure on Transport Across Caco-2 Cells" *Pharm. Res.* 8(12):1453-1459 (1991).

Coombes et al. "Biodegradable Polymeric Microparticles for Drug Delivery and Vaccine Formulation: the Surface Attachment of Hydrophilic Species Using the Concept of Poly(Ethylene Glycol) Anchoring Segments" *Biomaterials* 18:1153-1161 (1997).

Damge et al. "Poly(alkyl cyanoacrylate) Nanospheres for Oral Administration of Insulin" *Journal of Pharmaceutical Sciences* 86(12):1403-1409 (Dec. 1997).

Dandona et al. "Effect of an Oral Modified Insulin on Blood Glucose Levels in Fasting and Fed Type 1 Diabetic Patients Receiving a 'Basal' Regimen of Injected Insulin" American Diabetes Association Annual Meeting (Jun. 25, 2001) (Abstract).

Delgado et al. "The Uses and Properties of PEG-Linked Proteins" *Critical Reviews in Therapeutic Drug Carrier Systems* 9(3,4):249-304 (1992).

Ekwuribe et al. *Calcitonin Drug-Oligomer Conjugates, and Uses Thereof,* U.S. Appl. No. 10/166,355, filed Nov. 8, 2002, including Preliminary Amendment dated Feb. 26, 2003 and Supplemental Preliminary Amendment dated Mar. 31, 2003.

Ekwuribe et al. *Mixtures of Drug-Oligomer Conjugates Comprising Polyalkylene Glycol, Uses Thereof, and Methods of Making Same,* U.S. Appl. No. 09/873,797, filed Jun. 4, 2001.

Ekwuribe, Nnochiri "Conjugation-Stabilized Polypeptide Compositions, Therapeutic Delivery and Diagnostic Formulations Comprising Same, and Method of Making and Using the Same" *Biotechnology Advances* 14(4):575-576 (1996) (Abstract).

Engel et al. "Insulin: Intestinal Absorption as Water-in-Oil-in-Water Emulsions" *Nature* 219:856-857 (1968).

Fasano, Alessio "Innovative strategies for the oral delivery of drugs and peptides" *TIBTECH* 16:152-157 (1998).

Forst et al. "New Aspects on Biological Activity of C-peptide in IDDM Patients" *Exp. Clin. Endocrinol. Diabetes* 106:270-276 (1998).

Gish et al. "Nucleic Acids. 11. Synthesis of 5'-Esters of 1-β-D-Arabinofuranosylcytosine Possessing Antileukemic and Immunosuppressive Activity" *J. Med. Chem.* 14(12):1159-1162 (1971).

Gombotz & Pettit "Biodegradable Polymers for Protein and Peptide Drug Delivery" *Bioconjugate Chem.* 6:332-351 (1995).

Hashimoto et al. "Synthesis of Palmitoyl Derivatives of Insulin and Their Biological Activities" *Pharmaceutical Research* 6(2):171-176 (1989).

Hinds et al. "Synthesis and Characterization of Poly(ethylene glycol)-Insulin Conjugates" *Bioconjugate Chem.* 11:195-201 (2000).

Hong et al. "Nucleoside Conjugates. 7. Synthesis and Antitumor Activity of 1-β-D-Arabinofuranosylcytosine Conjugates of Ether Lipids" *J. Med. Chem.* 29:2038-2044 (1986).

Hostetler et al. "Synthesis and Antiretroviral Activity of Phospholipid Analogs of Azidothymidine and Other Antiviral Nucleosides" *The Journal of Biological Chemistry* 265(11):6112-6117 (1990).

Igarashi et al. "Biologically Active Peptides Conjugated with Lecithin for DDS" *Proceed. Intern. Symp. Cont. Rel. Bioactiv. Mater.* 17:367-368 (1990).

Kemmler et al. "On the Nature and Subcellular Localization of the Proinsulin Converting Enzymes" *Federation Proceedings* 30(Abstract 924):1210Abs (1971).

Kemmler et al. "Studies on the Conversion of Proinsulin to Insulin: I. Converison in Vitro with Trypsin and Carboxypeptidase B" *The Journal of Biological Chemistry* 246(22):6786-6791 (1971).

King et al. "Preparation of Protein Conjugates with Alkoxypolyethylene Glycols" *Int. J. Peptide Protein Res.* 16:147-155 (1980).

Kipnes et al. "Control of Postprandial Plasma Glucose by an Oral Insulin Product (HIM2) in Patients with Type 2 Diabetes" *Emerging Treatments and Technologies* 26:2 (2003).

Kipnes et al. "The Effects of an Oral Modified Insulin on Postprandial Blood Glucose Levels in Patients with Type 2 Diabetes Mellitus" American Diabetes Association Annual Meeting (Jun. 2001) (Poster).

Kipnes et al. "The Effects of an Oral Modified Insuling on Postprandial Blood Glucose Levels in Patients with Type 2 Diabetes" American Diabetes Association Annual Meeting (Jun. 24, 2001) (Abstract).

Kube, D.M. "Multitalented Proteins Play a Key Role in Therapeutics" *Genomics and Proteomics* (Sep. 2002).

Maislos et al. "The Source of the Circulating Aggregate of Insulin in Type I Diabetic Patients is Therapeutic Insulin" *J. Clin. Invest.* 77:717-723 (1986).

Savva & Huang "Effect of PEG Homopolymer and Grafted Amphiphilic PEG-Palmityl on the Thermotropic Phase Behavior of 1,2-Dipalmitoyl-SN-Glycero-3-Phosphocholine Bilayer" *Journal of Liposome Research* 9(3):357-365 (1999).

Marshutz et al. "Oral Peptide Drug Delivery: Polymer-Inhibitor Conjugates Protecting Insulin from Enzymatic Degradation In Vitro" *Biomaterials* 21:1499-1507 (2000).

Musabayane et al. "Orally Administered, Insulin-Loaded Amidated Pectin Hydrogel Beads Sustain Plasma Concentrations of Insulin in Streptozotocin-Diabetic Rats" *Journal of Endocrinology* 164:1-6 (2000).

Nucci et al. "The Therapeutic Value of Poly(ethylene Glycol)—Modified Proteins" *Ad. Drug. Del. Rev.* 6:133-151 (1991).

Oka et al. "Enhanced Intestinal Absorption of a Hydrophobic Polymer-Conjugated Protein Drug, Smancs, in an Oily Formulation" *Pharm. Res.* 7(8):852-855 (1990).

Pang, David C. "Bridging Gaps in Drug Discovery and Development" *Pharmaceutical Technology* 22:82-94 (Nov. 1998).

Patel et al. "Oral Administration on Insulin By Encapsulation Within Liposomes" *FEBS Lett.* 62(1):60-63 (1976).

Price, JC *Polyethlyene Glycol*, pp. 355-361, not dated.

Puskas et al. "Investigation of Chymotrypsin Digestion Profile of Orally Active Insulin Conjugate HIM2" *AAPS Pharm Sci.* 3(3) 2001 (Abstract).

Radhakrishnan et al. "Chemical Modification of Insulin with Amphiphilic Polymers Improves Intestinal Delivery," *Proceed. Intl. Symp. Control. Rel. Bioact. Mater.* 25:124-125 (1998) (Abstract).

Radhakrishnan et al. "Oral Delivery of Insulin: Single Selective Modification at B29-LYS With Amphiphilic Oligomer" Program and Abstracts, 1999 National Meeting of the Ameri. Assoc. Pharm. Scient., New Orleans, LA (1999) (Abstract).

Radhakrishnan et al. "Structure-Activity Relationship of Insulin Modified with Amphiphilic Polymers" Program and Abstracts, 1998 National Meeting of the Amer. Assoc. Pharm. Scient., San Francisco, CA *Pharm. Sci.* 1(1):S-59 (1998) (Abstract).

Radhakrishnan et al.. *Insulin Polypeptide-Oligomer Conjugates, Proinsulin Polypeptide-Oligomer Conjugates and Methods of Synthesizing Same*, U.S. Appl. No. 10/389,499, filed Mar. 17, 2003.

Ratner, R. E. et al. "Persistent Cutaneous Insulin Allergy Resulting from High-Molecular Weight Insulin Aggregates" *Diabetes* 39:728-733 (1990).

Richards et al. "Self-Association Properties of Monomeric Insulin Analogs Under Formulation Conditions" *Pharmaceutical Research* 15(9):1434-1441 (1998).

Robbins et al. "Antibodies to Covalent Aggregates of Insulin in Blood of Insulin-Using Diabetic Patients" *Diabetes* 36:838-841 (1987).

Russell-Jones, G. J. "Vitamin B12 Drug Delivery" *Proceed. Intern. Symp. Control. Rel. Bioactive. Mater.* 19:102-103 (1992).

Saffran et al. "A Model for the Study of the Oral Administration of Peptide Hormones" *Can. J. Biochem.* 57:548-553 (1979).

Saffran, M. et al. "A New Approach to the Oral Administration of Insulin and Other Peptide Drugs" *Science* 233:1081-1084 (1986).

Santiago et al. "Oral Immunization of Rats with Influenza Virus M Protein (M1) Microspheres" *Proceed. Intern.Symp. Cont. Rel. Bioactive. Mater.* 19:116-117 (1992).

Shah and Shen "Transcellular Delivery of an Insulin-Transferrin Conjugate in Enterocyte-like Caco-2 Cells" *Journal of Pharmaceutical Sciences* 85(12):1306-1311 (1996).

Shichiri et al. "Enteral Absorption of Water-in-Oil-in-Water Insulin Emulsions in Rabbits" *Diabetologia* 10:317-321 (1974).

Soltero et al. *Insulin Polypeptide-Oligomer Conjugates, Proinsulin Polypeptide-Oligomer Conjugates and Methods of Synthesizing Same* U.S. Appl. No. 10/382,022, filed Mar. 5, 2003.

Soltero et al. *Pharmaceutical Compositions of Drug-Oligomer Conjugates and Methods of Treating Diseases Therewith* U.S. Appl. No. 10/382,069, filed Mar. 5, 2003.

Soltero et al. *Pharmaceutical Compositions of Insulin Drug-Oligomer Conjugates and Methods of Treating Diseases Therewith* U.S. Appl. No. 10/382,155, filed Mar. 5, 2003.

Still and McAllister "Effects of Orally Active Modified Insulin in Type I Diabetic Patients" *Clinical Pharmacol. Therap.* 69(2):P95 (Feb. 2001) (Abstract).

Still and McAllister "Effects of Orally Active Modified Insulin in Type I Diabetic Patients" Slide Presentation Annual Meeting of the American Society for Clinical Pharmacology & Therapeutics, Orlando, FL, Mar. 9, 2001.

Still and McAllister "Effects of Orally Active Modified Insulin in Type I Diabetic Patients" Annual Meeting of the American Society for Clinical Pharmacology & Therapeutics, Orlando, FL, Mar. 9, 2001 (Handout).

Still et al. "Magnitude and Variability of Pharmacokinetic and Glucodynamic Responses to Modified Human Insulin Administered Orally to Healthy Volunteers" *Diabetes Research and Clinical Practice* 56:S77 (2002).

Still et al. *Methods of Reducing Hypoglycemic Episodes in the Treatment of Diabetes Mellitus*, U.S. Appl. No. 10/461,199, filed Jun. 13, 2003.

Still, J. Gordon "Development of Oral Insulin: Progress and Current Status" *Diabetes/Metabolism Research and Reviews* 18(1):S29-S37 (2002).

Still, J. Gordon "Oral Insulin Development" Slide Presentation, VI International St. Barts Symposium Diabetes 2000: Therapy and Technology, London, England, May 12, 2000.

Szleifer et al. "Spontaneous Liposome Formation Induced by Grafted Poly(Ethylene Oxide) Layers: Theoretical Prediction and Experimental Verification" *Proceedings of the National Academy of Sciences of the United States of America* 95(3):1032-1037 (1998).

Taniguchi et al. "Synthesis of Acyloyl Lysozyme and Improvement of its Lymphatic Transport Following Small Intestinal Administration in Rats" *Proceed. Intern. Symp. Control. Rel. Bioactiv. Mater.* 19:104-105 (1992).

Uchio et al. "Site-Specific Insulin Conjugates with Enhanced Stability and Extended Action Profile" *Advanced Drug Delivery Reviews* 35:289-306 (1999).

Vreeland et al. "Molar Mass Profiling of Synthetic Polymers by Free-Solution Capillary Electrophoresis of DNA-Polymer Conjugates" *Analytical Chemistry* 73(8):1795-1803 (2001).

Wahren et al. "Role of C-peptide in Human Physiology" *Am. J. Physiol. Endocrinol. Metab.* 278:E759-E768 (2000).

Zalipsky et al. "Attachment of Drugs to Polyethylene Glycols" *Eur. Polym. J.* 19(12):1177-1183 (1983).

Ziv and Bendayan "Intestinal Absorption of Peptides Through the Enterocytes" *Microscopy Research and Technique* 49:346-352 (2000).

Mehvar, Reza; Modulation of the Pharmacokinetics and Pharmacodynamics of Proteins by Polyethylene Glycol Conjugation; *J. Pharm. Pharmaceut Sci.*; 3(1):125-136; 2000.

* cited by examiner

(50) $CH_3(OC_2H_4)_6\text{-}OH$ +

(51) $CH_3(OC_2H_4)_6\text{-}O$  + TEA (52)

1° alcohol extension dimer (66) + 1° alcohol extension dimer mesylate (70) → (72)

(73) + (74) → (75)

MIXTURES OF CALCITONIN DRUG-OLIGOMER CONJUGATES COMPRISING POLYALKYLENE GLYCOL, USES THEREOF, AND METHODS OF MAKING SAME

RELATED APPLICATION

This application is a continuation of U.S. patent application Ser. No. 09/873,777, filed Jun. 4, 2001, issued Mar. 30, 2004 as U.S. Pat. No. 6,713,452, assigned to the assignee of the present invention, the disclosure of which is incorporated by reference herein in its entirety.

FIELD OF THE INVENTION

The present invention relates to drug-oligomer conjugates, and, more particularly, to calcitonin drug-oligomer conjugates.

BACKGROUND OF THE INVENTION

Calcitonin is a naturally occurring hormone with a short half-life that is believed to act directly on osteoclasts (via receptors on the cell surface for calcitonin). This action may directly inhibit osteoclastic bone resorption, which may lead to hypocalcemic and/or hypophosphatemic serum effects. Calcitonin may be useful in treating various bone disorders including, but not limited to, osteoporosis and Paget's disease.

Osteoporosis is a bone disease in which bone tissue is normally mineralized, but the amount of bone is decreased and the structural integrity of trabecular bone is impaired. Cortical bone becomes more porous and thinner. This makes the bone weaker and more likely to fracture. In the United States, about 21% of postmenopausal women have osteoporosis (low bone density), and about 16% have had a fracture. In women older than 80, about 40% have experienced a fracture of the hip, vertebra, arm, or pelvis. The population of older men and women has been increasing, and therefore the number of people with osteoporosis is increasing.

Calcitonin given as a subcutaneous injection has shown significant improvements in bone density; however, a high incidence of side effects, including pain at the injection site, flushing and nausea, have been reported which may limit the use of the drug.

Paget's disease of bone is a metabolic bone disorder of unknown origin which normally affects older people. The disease causes an increased and irregular formation of bone as the bone cells, which are responsible for dissolving the body's old bone and replacing it with new, become out of control. Over a period of time the deformed new bone becomes larger, weaker and has more blood vessels than normal bone. Unlike normal bone, the structure is irregular and consequently weaker, which makes it prone to fracture even after a minor injury.

In its mildest form the disease has no symptoms. In more severe cases the pain can be intense. The relentless progression of the disease may cause bones to bow, the skull may increase in size and the spinal column may curve. As the bones enlarge they may cause pressure on nearby nerves which can result in muscle weakness. In the case of severe skull enlargement this pressure can result in deafness, disturbed vision, dizziness and tinnitus.

Calcitonin may be effective in treating disorders of increased skeletal remodeling, such as Paget's disease. In treating Paget's disease, chronic use of calcitonin may produce long-term reduction in symptoms; however, side effects of calcitonin administration may include nausea, hand swelling, urticaria, and intestinal cramping.

Various references have proposed conjugating polypeptides such as calcitonin with polydispersed mixtures of polyethylene glycol or polyethylene glycol-containing polymers. For example, U.S. Pat. No. 5,359,030 to Ekwuribe proposes conjugating polypeptides such as calcitonin with polydispersed mixtures of polyethylene glycol modified glycolipid polymers and polydispersed mixtures of polyethylene glycol modified fatty acid polymers. The number average molecular weight of polymer resulting from each combination is preferred to be in the range of from about 500 to about 10,000 Daltons.

The polydispersity of the polymer mixtures and conjugates described in Ekwuribe is likely a result of the use of polydispersed polyethylene glycol in the polymer synthesis. PEG is typically produced by base-catalyzed ring-opening polymerization of ethylene oxide. The reaction is initiated by adding ethylene oxide to ethylene glycol, with potassium hydroxide as catalyst. This process results in a polydispersed mixture of polyethylene glycol polymers having a number average molecular weight within a given range of molecular weights. For example, PEG products offered by Sigma-Aldrich of Milwaukee, Wis. are provided in polydispersed mixtures such as PEG 400 ($M_n$ 380–420); PEG 1,000 ($M_n$ 950–1,050); PEG 1,500 ($M_n$ 1,400–1,600); and PEG 2,000 ($M_n$ 1,900–2,200).

It is desirable to provide non-polydispersed mixtures of calcitonin drug-oligomer conjugates where the oligomer comprises polyethylene glycol.

SUMMARY OF THE INVENTION

It has unexpectedly been discovered that a mixture of calcitonin-oligomer conjugates comprising polyethylene glycol according to embodiments of the present invention may lower serum calcium levels by 10, 15 or even 20 percent or more. Moreover, a mixture of calcitonin-oligomer conjugates comprising polyethylene glycol according to embodiments of the present invention may be more effective at surviving an in vitro model of intestinal digestion than non-conjugated calcitonin. Furthermore, mixtures of calcitonin-oligomer conjugates comprising polyethylene glycol according to embodiments of the present invention may exhibit a higher bioavailability than non-conjugated calcitonin.

According to embodiments of the present invention, a substantially monodispersed mixture of conjugates each comprising a calcitonin drug coupled to an oligomer that comprises a polyethylene glycol moiety is provided. The polyethylene glycol moiety preferably has at least 2, 3, or 4 polyethylene glycol subunits and, most preferably, has at least 7 polyethylene glycol subunits. The oligomer preferably further comprises a lipophilic moiety. The calcitonin drug is preferably salmon calcitonin. Oligomers are preferably coupled at $Lys^{11}$ and $Lys^{18}$ of the salmon calcitonin. The conjugate is preferably amphiphilically balanced such that the conjugate is aqueously soluble and able to penetrate biological membranes.

According to other embodiments of the present invention, a substantially monodispersed mixture of conjugates is provided where each conjugate includes salmon calcitonin covalently coupled at $Lys^{18}$ of the salmon calcitonin to a carboxylic acid moiety of a first oligomer that comprises octanoic acid covalently coupled at the end distal to the carboxylic acid moiety to a methyl terminated polyethylene glycol moiety having at least 7 polyethylene glycol subunits, and covalently coupled at Lys[18] of the salmon calcitonin to a carboxylic acid moiety of a second oligomer that comprises octanoic acid covalently coupled at the end distal to the carboxylic acid moiety to a methyl terminated polyethylene glycol moiety having at least 7 polyethylene glycol subunits.

According to still other embodiments of the present invention, a substantially monodispersed mixture of conjugates is provided where each conjugate comprises a calcitonin drug coupled to an oligomer comprising a polyethylene glycol moiety, and the mixture is capable of lowering serum calcium levels in a subject by at least 5 percent.

According to yet other embodiments of the present invention, a substantially monodispersed mixture of conjugates is provided where each conjugate comprises a calcitonin drug coupled to an oligomer comprising a polyethylene glycol moiety, and the mixture has an increased resistance to degradation by chymotrypsin and/or trypsin when compared to the resistance to degradation by chymotrypsin and/or trypsin of the calcitonin drug which is not coupled to the oligomer.

According to other embodiments of the present invention, a substantially monodispersed mixture of conjugates is provided where each conjugate comprises a calcitonin drug coupled to an oligomer comprising a polyethylene glycol moiety, and the mixture has a higher bioefficacy than the bioefficacy of the calcitonin drug which is not coupled to the oligomer.

According to still other embodiments of the present invention, a mixture of conjugates is provided where each conjugate includes a calcitonin drug coupled to an oligomer that comprises a polyethylene glycol moiety, and the mixture has a molecular weight distribution with a standard deviation of less than about 22 Daltons.

According to yet other embodiments of the present invention, a mixture of conjugates is provided where each conjugate includes a calcitonin drug coupled to an oligomer that comprises a polyethylene glycol moiety, and the mixture has a dispersity coefficient (DC) greater than 10,000 where $$DC = \frac{\left(\sum_{i=1}^{n} N_i M_i\right)^2}{\sum_{i=1}^{n} N_i M_i^2 \sum_{i=1}^{n} N_i - \left(\sum_{i=1}^{n} N_i M_i\right)^2}$$

wherein:
n is the number of different molecules in the sample;
$N_i$ is the number of $i^{th}$ molecules in the sample; and
$M_i$ is the mass of the $i^{th}$ molecule.

According to other embodiments of the present invention, a mixture of conjugates is provided in which each conjugate includes a calcitonin drug coupled to an oligomer and has the same number of polyethylene glycol subunits.

According to still other embodiments of the present invention, a mixture of conjugates is provided in which each conjugate has the same molecular weight and has the formula:

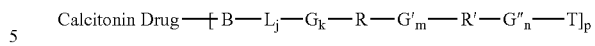

(A)

wherein:
B is a bonding moiety;
L is a linking group;
G, G' and G" are individually selected spacer groups;
R is a lipophilic group and R' is a polyalkylene glycol group, or R' is the lipophilic group and R is the polyalkylene oxide group;
T is a terminating group;
j, k, m and n are individually 0 or 1; and
p is an integer from 1 to the number of nucleophilic residues on the calcitonin drug.

Pharmaceutical compositions comprising conjugate mixtures of the present invention as well as methods of treating osteoporosis in a subject in need of such treatment by administering an effective amount of such pharmaceutical compositions are also provided. Additionally, methods of synthesizing such conjugate mixtures are provided.

Calcitonin-oligomer conjugate mixtures according to embodiments of the present invention may lower serum calcium levels by 20 percent or more. Moreover, such conjugates may provide decreased degradation by intestinal enzymes and/or provide increased bioavailability when compared to non-conjugated calcitonin.

DETAILED DESCRIPTION OF PREFERRED EMBODIMENTS

Figure 1:
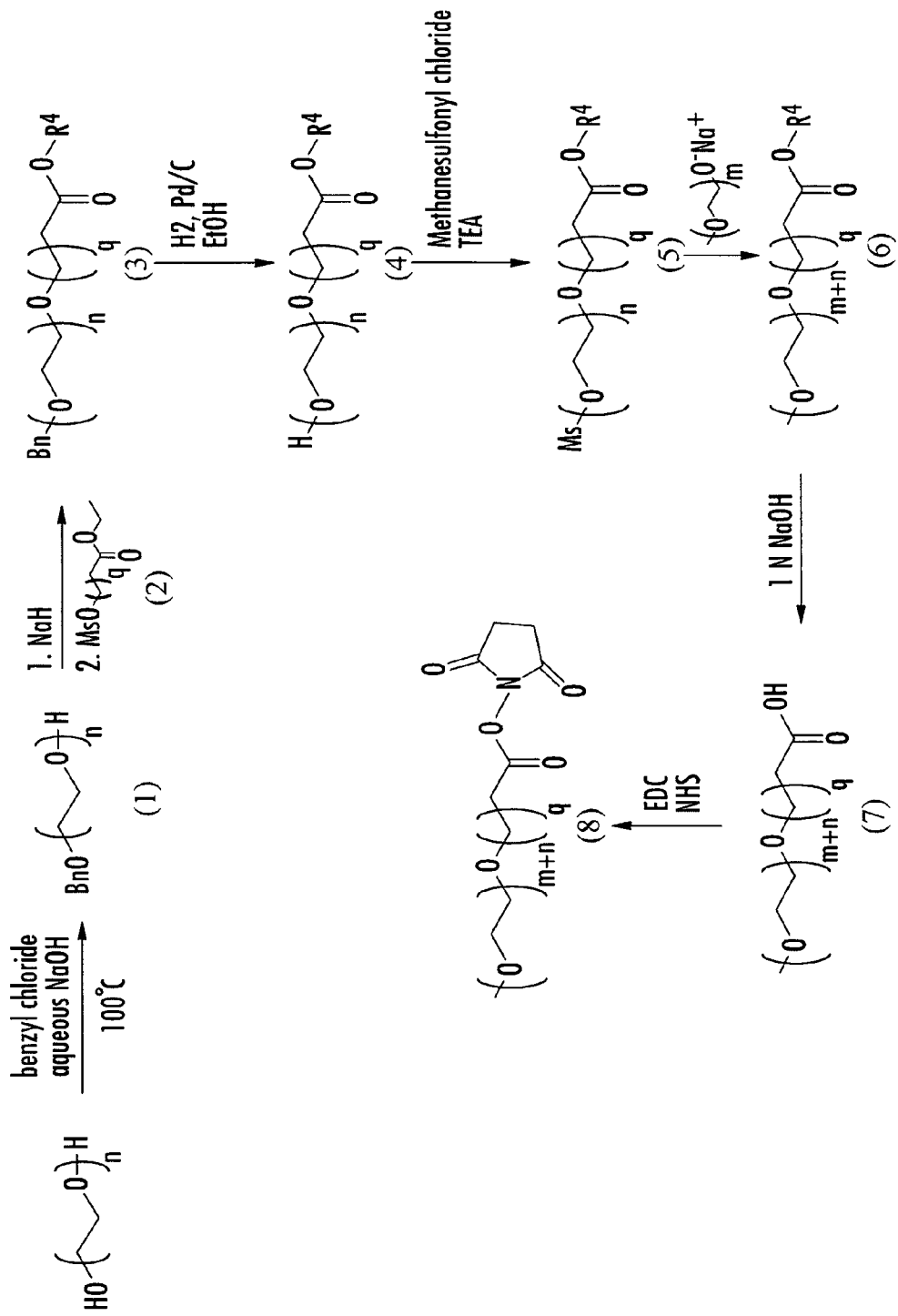
FIG. 1 illustrates a generic scheme for synthesizing a mixture of activated polymers comprising a polyethylene glycol moiety and a fatty acid moiety according to embodiments of the present invention.

The invention will now be described with respect to preferred embodiments described herein. It should be appreciated however that these embodiments are for the purpose of illustrating the invention, and are not to be construed as limiting the scope of the invention as defined by the claims.

As used herein, the term "non-polydispersed" is used to describe a mixture of compounds having a dispersity that is in contrast to the polydispersed mixtures described in U.S. Pat. No. 5,359,030 to Ekwuribe.

As used herein, the term "substantially monodispersed" is used to describe a mixture of compounds wherein at least about 95 percent of the compounds in the mixture have the same molecular weight.

As used herein, the term "monodispersed" is used to describe a mixture of compounds wherein about 100 percent of the compounds in the mixture have the same molecular weight.

As used herein, the term "substantially purely monodispersed" is used to describe a mixture of compounds wherein at least about 95 percent of the compounds in the mixture have the same molecular weight and have the same molecular structure. Thus, a substantially purely monodispersed mixture is a substantially monodispersed mixture, but a substantially monodispersed mixture is not necessarily a substantially purely monodispersed mixture.

As used herein, the term "purely monodispersed" is used to describe a mixture of compounds wherein about 100 percent of the compounds in the mixture have the same molecular weight and have the same molecular structure. Thus, a purely monodispersed mixture is a monodispersed mixture, but a monodispersed mixture is not necessarily a purely monodispersed mixture.

As used herein, the term "weight average molecular weight" is defined as the sum of the products of the weight fraction for a given molecule in the mixture times the mass of the molecule for each molecule in the mixture. The "weight average molecular weight" is represented by the symbol $M_w$.

As used herein, the term "number average molecular weight" is defined as the total weight of a mixture divided by the number of molecules in the mixture and is represented by the symbol $M_n$.

As used herein, the term "dispersity coefficient" (DC) is defined by the formula:

$$DC = \frac{\left(\sum_{i=1}^{n} N_i M_i\right)^2}{\sum_{i=1}^{n} N_i M_i^2 \sum_{i=1}^{n} N_i - \left(\sum_{i=1}^{n} N_i M_i\right)^2}$$

wherein:
n is the number of different molecules in the sample;
$N_i$ is the number of $i^{th}$ molecules in the sample; and
$M_i$ is the mass of the $i^{th}$ molecule.

As used herein, the term "intra-subject variability" means the variability in activity occurring within the same subject when the subject is administered the same dose of a drug or pharmaceutical composition at different times.

As used herein, the term "inter-subject variability" means the variability in activity between two or more subjects when each subject is administered the same dose of a given drug or pharmaceutical formulation.

As used herein, the term "bioefficacy" means the ability of a drug or drug conjugate to interact with one or more desired receptors in vivo.

As used herein, the term "calcitonin drug" means a drug possessing all or some of the biological activity of calcitonin.

As used herein, the term "calcitonin" means chicken calcitonin, eel calcitonin, human calcitonin, porcine calcitonin, rat calcitonin or salmon calcitonin provided by natural, synthetic, or genetically engineered sources.

As used herein, the term "calcitonin analog" means calcitonin wherein one or more of the amino acids have been replaced while retaining some or all of the activity of the calcitonin. The analog is described by noting the replacement amino acids with the position of the replacement as a superscript followed by a description of the calcitonin. For example, "$Pro^2$ calcitonin, human" means that the glycine typically found at the 2 position of a human calcitonin molecule has been replaced with proline.

Calcitonin analogs may be obtained by various means, as will be understood by those skilled in the art. For example, certain amino acids may be substituted for other amino acids in the calcitonin structure without appreciable loss of interactive binding capacity with structures such as, for example, antigen-binding regions of antibodies or binding sites on substrate molecules. As the interactive capacity and nature of calcitonin defines its biological functional activity, certain amino acid sequence substitutions can be made in the amino acid sequence and nevertheless remain a polypeptide with like properties.

In making such substitutions, the hydropathic index of amino acids may be considered. The importance of the hydropathic amino acid index in conferring interactive biologic function on a polypeptide is generally understood in the art. It is accepted that the relative hydropathic character of the amino acid contributes to the secondary structure of the resultant polypeptide, which in turn defines the interaction of the polypeptide with other molecules, for example, enzymes, substrates, receptors, DNA, antibodies, antigens, and the like. Each amino acid has been assigned a hydropathic index on the basis of its hydrophobicity and charge characteristics as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). As will be understood by those skilled in the art, certain amino acids may be substituted by other amino acids having a similar hydropathic index or score and still result in a polypeptide with similar biological activity, i.e., still obtain a biological functionally equivalent polypeptide. In making such changes, the substitution of amino acids whose hydropathic indices are within ±2 of each other is preferred, those which are within +1 of each other are particularly preferred, and those within ±0.5 of each other are even more particularly preferred.

It is also understood in the art that the substitution of like amino acids can be made effectively on the basis of hydrophilicity. U.S. Pat. No. 4,554,101 provides that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (±3.0); aspartate (+3.0±1); glutamate (+3.0±1); seine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). As is understood by those skilled in the art, an amino acid can be substituted for another having a similar hydrophilicity value and still obtain a biologically equivalent, and in particular, an immunologically equivalent polypeptide. In such changes, the substitution of amino acids whose hydrophilicity values are within ±2 of each other is preferred, those which are within ±1 of each other are particularly preferred, and those within ±0.5 of each other are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions (i.e., amino acids that may be interchanged without significantly altering the biological activity of the polypeptide) that take various of the foregoing characteristics into consideration are well known to those of skill in the art and include, for example: arginine and lysine; glutamate and aspartate; serine and threonine; glutamine and asparagine; and valine, leucine and isoleucine.

As used herein, the term "calcitonin fragment" means a segment of the amino acid sequence found in the calcitonin that retains some or all of the activity of the calcitonin.

As used herein, the term "calcitonin fragment analog" means a segment of the amino acid sequence found in the calcitonin molecule wherein one or more of the amino acids in the segment have been replace while retaining some or all of the activity of the calcitonin.

As used herein, the term "PEG" refers to straight or branched polyethylene glycol polymers, and includes the monomethylether of polyethylene glycol (mPEG). The terms "PEG subunit" and polyethylene glycol subunit refer to a single polyethylene glycol unit, i.e., —(CH$_2$CH$_2$O)—.

As used herein, the term "lipophilic" means the ability to dissolve in lipids and/or the ability to penetrate, interact with and/or traverse biological membranes, and the term, "lipophilic moiety" or "lipophile" means a moiety which is lipophilic and/or which, when attached to another chemical entity, increases the lipophilicity of such chemical entity. Examples of lipophilic moieties include, but are not limited to, alkyls, fatty acids, esters of fatty acids, cholesteryl, adamantyl and the like.

As used herein, the term "lower alkyl" refers to substituted or unsubstituted alkyl moieties having from 1 to 5 carbon atoms.

As used herein, the term "higher alkyl" refers to substituted or unsubstituted alkyl moieties having 6 or more carbon atoms.

In embodiments of the present invention, a substantially monodispersed mixture of calcitonin drug-oligomer conjugates is provided. Each calcitonin drug-oligomer conjugate in the monodispersed mixture includes a calcitonin drug coupled to an oligomer that comprises a polyethylene glycol moiety. Preferably, at least about 96, 97, 98 or 99 percent of the conjugates in the mixture have the same molecular weight. More preferably, the mixture is a monodispersed mixture. Even more preferably, the mixture is a substantially purely monodispersed mixture. Still more preferably, at least about 96, 97, 98 or 99 percent of the conjugates in the mixture have the same molecular weight and have the same molecular structure. Most preferably, the mixture is a purely monodispersed mixture.

The calcitonin drug is preferably calcitonin. More preferably, the calcitonin drug is salmon calcitonin. However, it is to be understood that the calcitonin drug may be selected from various calcitonin drugs known to those skilled in the art including, for example, calcitonin precursor peptides, calcitonin, calcitonin analogs, calcitonin fragments, and calcitonin fragment analogs. Calcitonin precursor peptides include, but are not limited to, katacalcin (PDN-21) (C-procalcitonin), and N-proCT (amino-terminal procalcitonin cleavage peptide), human. Calcitonin analogs may be provided by substitution of one or more amino acids in calcitonin as described above. Calcitonin fragments include, but are not limited to, calcitonin 1–7, human; and calcitonin 8–32, salmon. Calcitonin fragment analogs may be provided by substitution of one or more of the amino acids in a calcitonin fragment as described above.

The oligomer may be various oligomers comprising a polyethylene glycol moiety as will be understood by those skilled in the art. Preferably, the polyethylene glycol moiety of the oligomer has at least 2, 3 or 4 polyethylene glycol subunits. More preferably, the polyethylene glycol moiety has at least 5 or 6 polyethylene glycol subunits and, most preferably, the polyethylene glycol moiety has at least 7 polyethylene glycol subunits.

The oligomer may comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The oligomer may further comprise one or more additional hydrophilic moieties (i.e., moieties in addition to the polyethylene glycol moiety) including, but not limited to, sugars, polyalkylene oxides, and polyamine/PEG copolymers. As polyethylene glycol is a polyalkylene oxide, the additional hydrophilic moiety may be a polyethylene glycol moiety. Adjacent polyethylene glycol moieties will be considered to be the same moiety if they are coupled by an ether bond. For example, the moiety

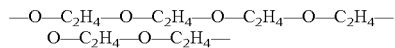

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties will be considered to be different moieties if they are coupled by a bond other than an ether bond. For example, the moiety

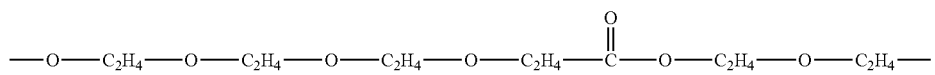

is a polyethylene glycol moiety having four polyethylene glycol subunits and an additional hydrophilic moiety having two polyethylene glycol subunits. Preferably, oligomers according to embodiments of the present invention comprise a polyethylene glycol moiety and no additional hydrophilic moieties.

The oligomer may further comprise one or more lipophilic moieties as will be understood by those skilled in the art. The lipophilic moiety is preferably a saturated or unsaturated, linear or branched alkyl moiety or a saturated or unsaturated, linear or branched fatty acid moiety. When the lipophilic moiety is an alkyl moiety, it is preferably a linear, saturated or unsaturated alkyl moiety having 1 to 28 carbon atoms. More preferably, the alkyl moiety has 2 to 12 carbon atoms. When the lipophilic moiety is a fatty acid moiety, it is preferably a natural fatty acid moiety that is linear, saturated or unsaturated, having 2 to 18 carbon atoms. More preferably, the fatty acid moiety has 3 to 14 carbon atoms. Most preferably, the fatty acid moiety has at least 4, 5 or 6 carbon atoms.

The oligomer may further comprise one or more spacer moieties as will be understood by those skilled in the art. Spacer moieties may, for example, be used to separate a hydrophilic moiety from a lipophilic moiety, to separate a lipophilic moiety or hydrophilic moiety from the calcitonin drug, to separate a first hydrophilic or lipophilic moiety from a second hydrophilic or lipophilic moiety, or to separate a hydrophilic moiety or lipophilic moiety from a linker moiety. Spacer moieties are preferably selected from the group consisting of sugar, cholesterol and glycerine moieties.

The oligomer may further comprise one or more linker moieties that are used to couple the oligomer with the calcitonin drug as will be understood by those skilled in the art. Linker moieties are preferably selected from the group consisting of alkyl and fatty acid moieties.

The oligomer may further comprise one or more terminating moieties at the one or more ends of the oligomer which are not coupled to the calcitonin drug. The terminating moiety is preferably an alkyl or alkoxy moiety, and is more preferably a lower alkyl or lower alkoxy moiety. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugars, cholesterol, alcohols, and fatty acids.

The oligomer is preferably covalently coupled to the calcitonin drug. In some embodiments, the calcitonin drug is coupled to the oligomer utilizing a hydrolyzable bond (e.g., an ester or carbonate bond). A hydrolyzable coupling may provide a calcitonin drug-oligomer conjugate that acts as a prodrug. In certain instances, for example where the calcitonin drug-oligomer conjugate is inactive (i.e., the conjugate lacks the ability to affect the body through the calcitonin drug's primary mechanism of action), a hydrolyzable coupling may provide for a time-release or controlled-release effect, administering the calcitonin drug over a given time period as one or more oligomers are cleaved from their respective calcitonin drug-oligomer conjugates to provide the active drug. In other embodiments, the calcitonin drug is coupled to the oligomer utilizing a non-hydrolyzable bond (e.g., a carbamate, amide, or ether bond). Use of a non-hydrolyzable bond may be preferable when it is desirable to allow the calcitonin drug-oligomer conjugate to circulate in the bloodstream for an extended period of time, preferably at least 2 hours. When the oligomer is covalently coupled to the calcitonin drug, the oligomer further comprises one or more bonding moieties that are used to covalently couple the oligomer with the calcitonin drug as will be understood by those skilled in the art. Bonding moieties are preferably selected from the group consisting of covalent bond(s), ester moieties, carbonate moieties, carbamate moieties, amide moieties and secondary amine moieties. More than one moiety on the oligomer may be covalently coupled to the calcitonin drug.

While the oligomer is preferably covalently coupled to the calcitonin drug, it is to be understood that the oligomer may be non-covalently coupled to the calcitonin drug to form a non-covalently conjugated calcitonin drug-oligomer complex. As will be understood by those skilled in the art, non-covalent couplings include, but are not limited to, hydrogen bonding, ionic bonding, Van der Waals bonding, and micellular or liposomal encapsulation. According to embodiments of the present invention, oligomers may be suitably constructed, modified and/or appropriately functionalized to impart the ability for non-covalent conjugation in a selected manner (e.g., to impart hydrogen bonding capability), as will be understood by those skilled in the art. According to other embodiments of present invention, oligomers may be derivatized with various compounds including, but not limited to, amino acids, oligopeptides, peptides, bile acids, bile acid derivatives, fatty acids, fatty acid derivatives, salicylic acids, salicylic acid derivatives, aminosalicylic acids, and aminosalicylic acid derivatives. The resulting oligomers can non-covalently couple (complex) with drug molecules, pharmaceutical products, and/or pharmaceutical excipients. The resulting complexes preferably have balanced lipophilic and hydrophilic properties. According to still other embodiments of the present invention, oligomers may be derivatized with amine and/or alkyl amines. Under suitable acidic conditions, the resulting oligomers can form non-covalently conjugated complexes with drug molecules, pharmaceutical products and/or pharmaceutical excipients. The products resulting from such complexation preferably have balanced lipophilic and hydrophilic properties.

More than one oligomer (i.e., a plurality of oligomers) may be coupled to the calcitonin drug. The oligomers in the plurality are preferably the same. However, it is to be understood that the oligomers in the plurality may be different from one another, or, alternatively, some of the oligomers in the plurality may be the same and some may be different. When a plurality of oligomers are coupled to the calcitonin drug, it may be preferable to couple one or more of the oligomers to the calcitonin drug with hydrolyzable bonds and couple one or more of the oligomers to the calcitonin drug with non-hydrolyzable bonds. Alternatively, all of the bonds coupling the plurality of oligomers to the calcitonin drug may be hydrolyzable, but have varying degrees of hydrolyzability such that, for example, one or more of the oligomers is rapidly removed from the calcitonin drug by hydrolysis in the body and one or more of the oligomers is slowly removed from the calcitonin drug by hydrolysis in the body.

The oligomer may be coupled to the calcitonin drug at various nucleophilic residues of the calcitonin drug including, but not limited to, nucleophilic hydroxyl functions and/or amino functions. When the calcitonin drug is a polypeptide, a nucleophilic hydroxyl function may be found, for example, at serine and/or tyrosine residues, and a nucleophilic amino function may be found, for example, at histidine and/or lysine residues, and/or at the one or more N-termini of the polypeptide. When an oligomer is coupled to the one or more N-terminus of the calcitonin polypeptide, the coupling preferably forms a secondary amine. When the calcitonin drug is salmon calcitonin, for example, the oligomer may be coupled to an amino functionality of the salmon calcitonin, including the amino functionality of $Lys^{11}$, $Lys^{18}$ and/or the N-terminus. While one or more oligomers may be coupled to the salmon calcitonin, a higher bioefficacy, such as improved serum calcium lowering ability, is observed for the di-conjugated salmon calcitonin where an oligomer is coupled to the amino functionalities of $Lys^{11}$ and the $Lys^{18}$.

Figure 3:
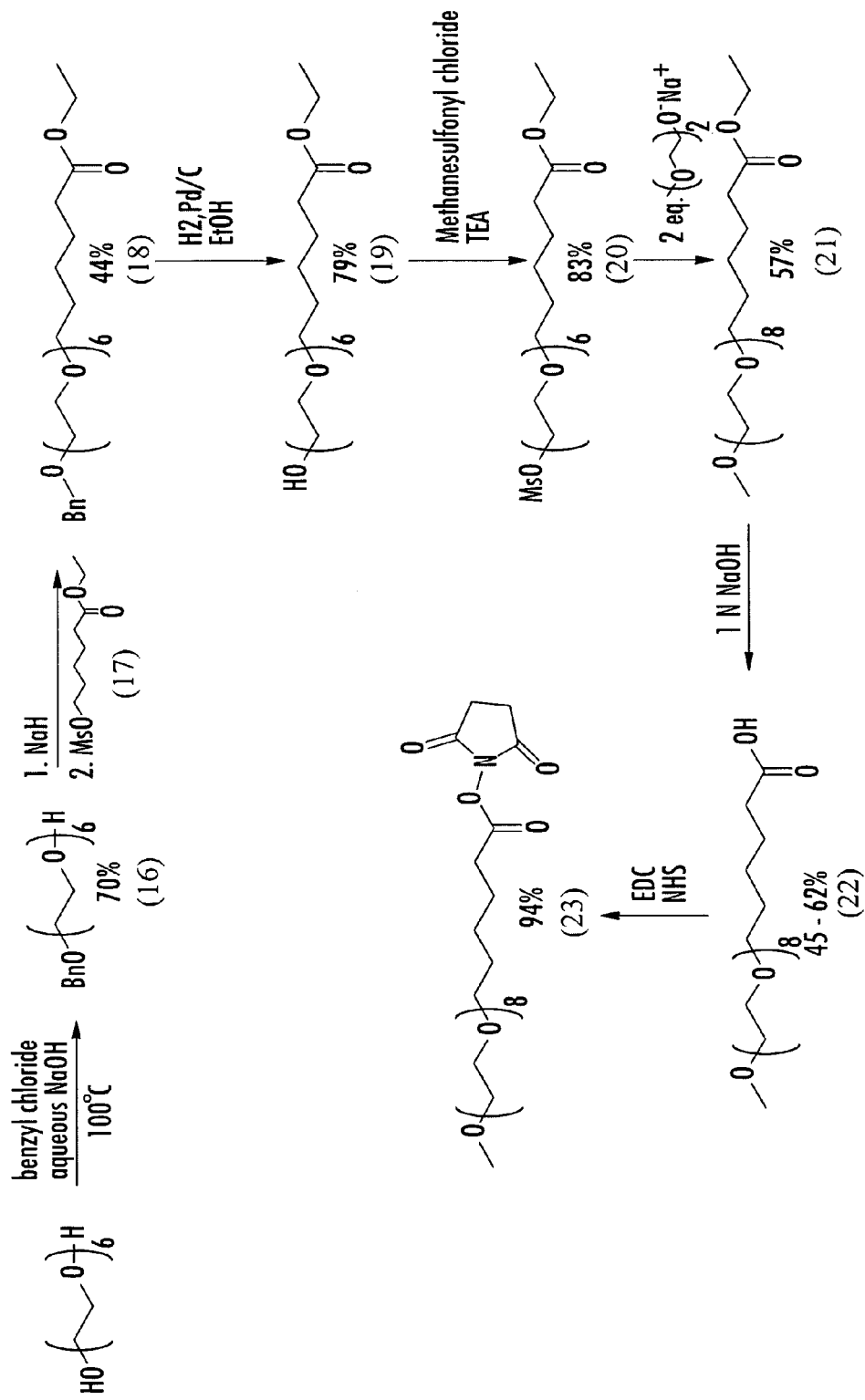
FIG. 3 illustrates a scheme for synthesizing a mixture of activated mPEG7-hexyl oligomers according to embodiments of the present invention.
Figure 4:
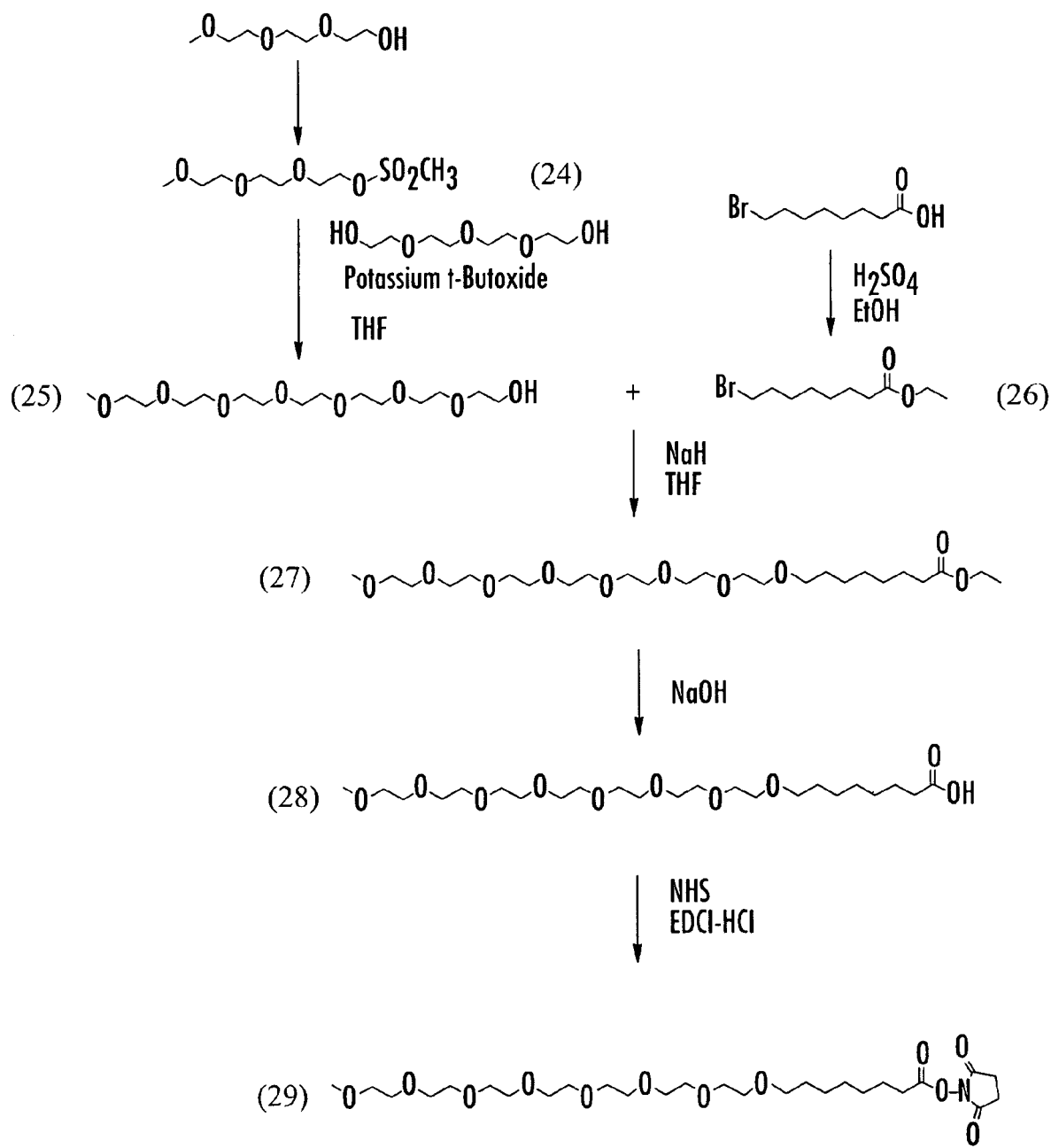
FIG. 4 illustrates a scheme for synthesizing a mixture of activated mPEG7-octyl oligomers according to embodiments of the present invention.
Figure 5:
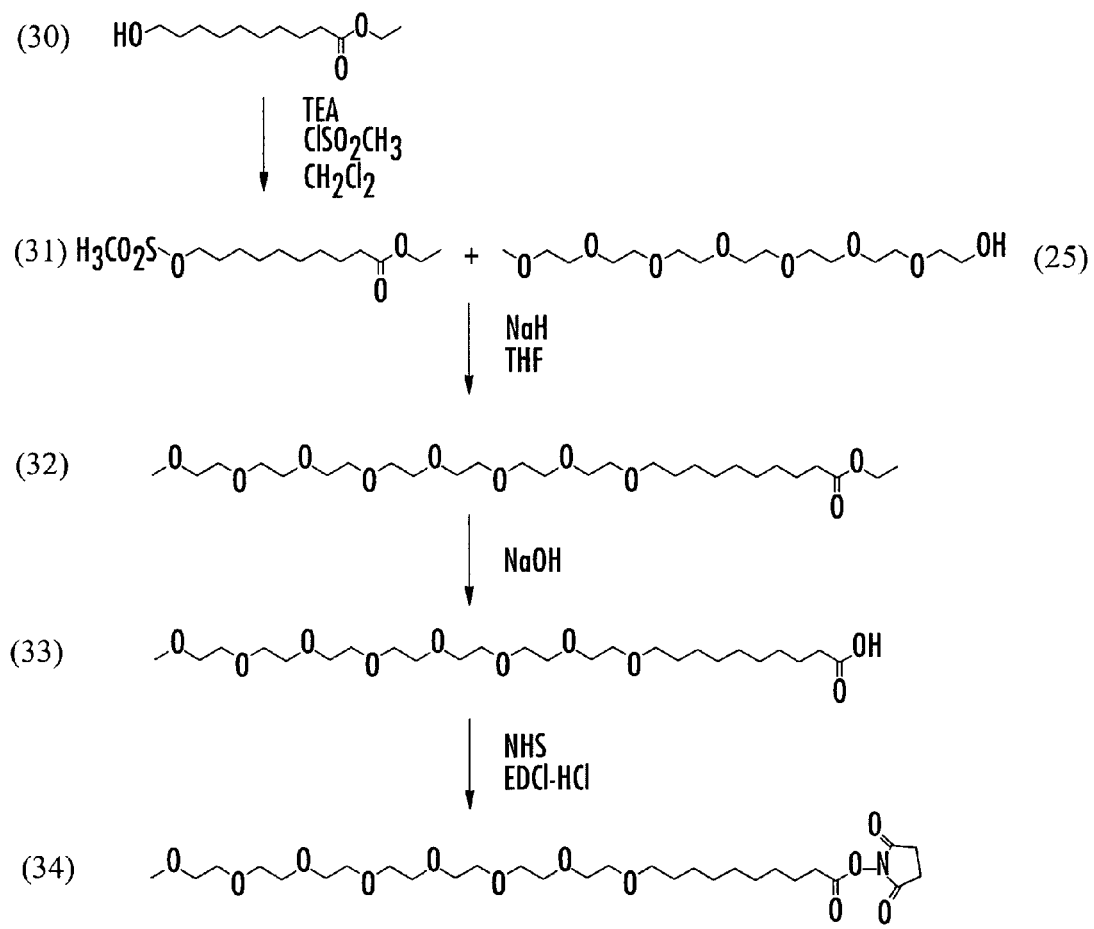
FIG. 5 illustrates a scheme for synthesizing a mixture of activated mPEG-decyl oligomers according to embodiments of the present invention.
Figure 6:
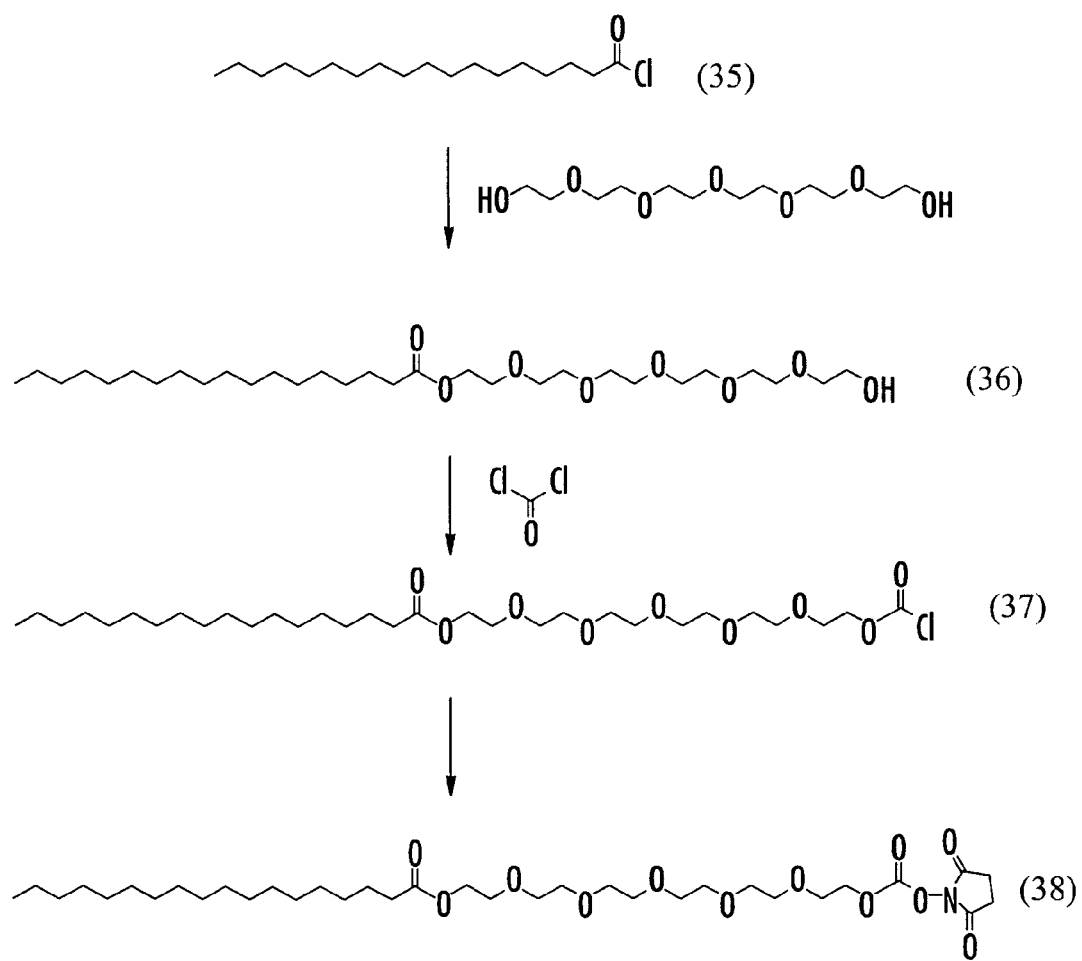
FIG. 6 illustrates a scheme for synthesizing a mixture of activated stearate-PEG6 oligomers according to embodiments of the present invention.
Figure 7:
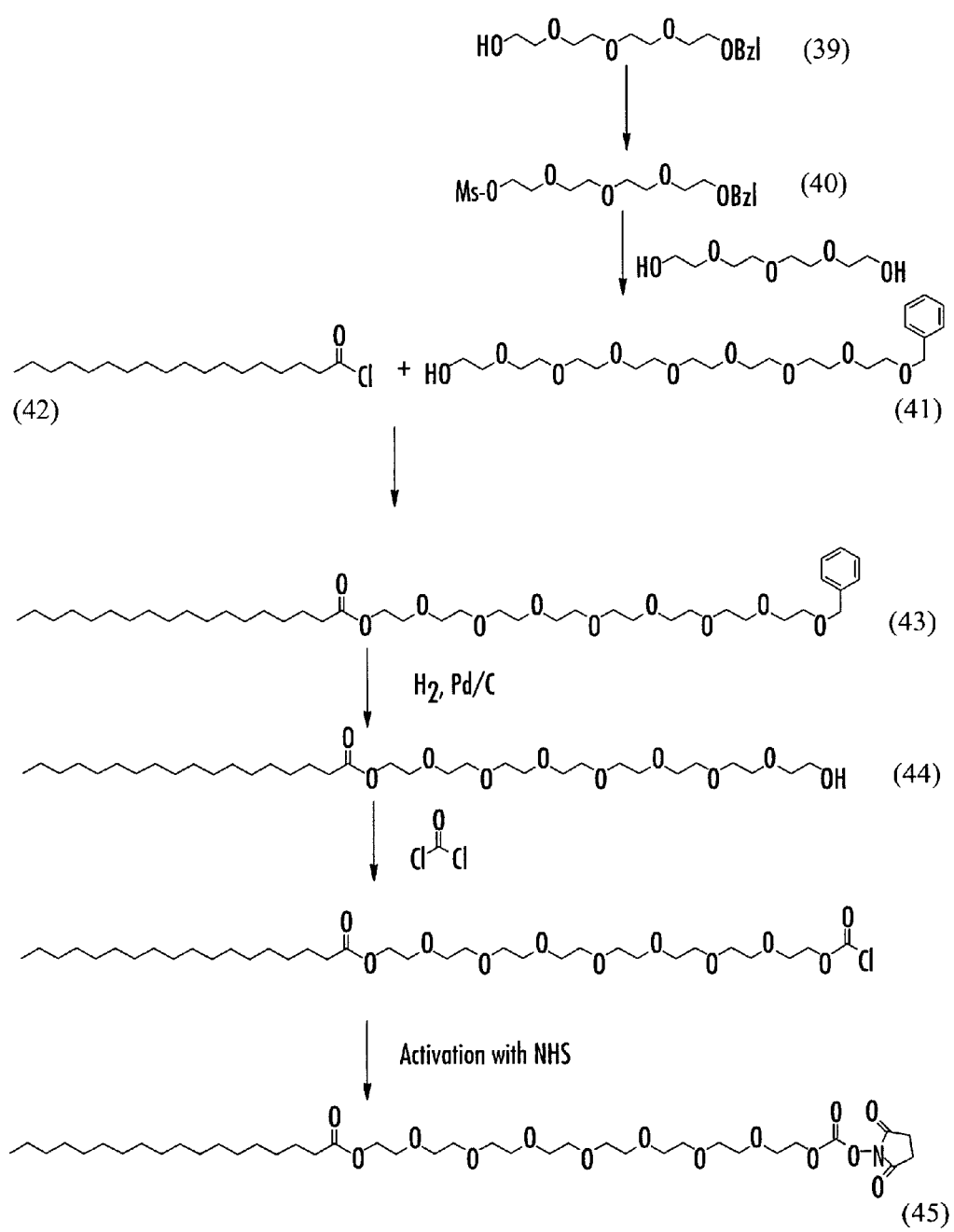
FIG. 7 illustrates a scheme for synthesizing a mixture of activated stearate-PEG8 oligomers according to embodiments of the present invention.
Figure 8:
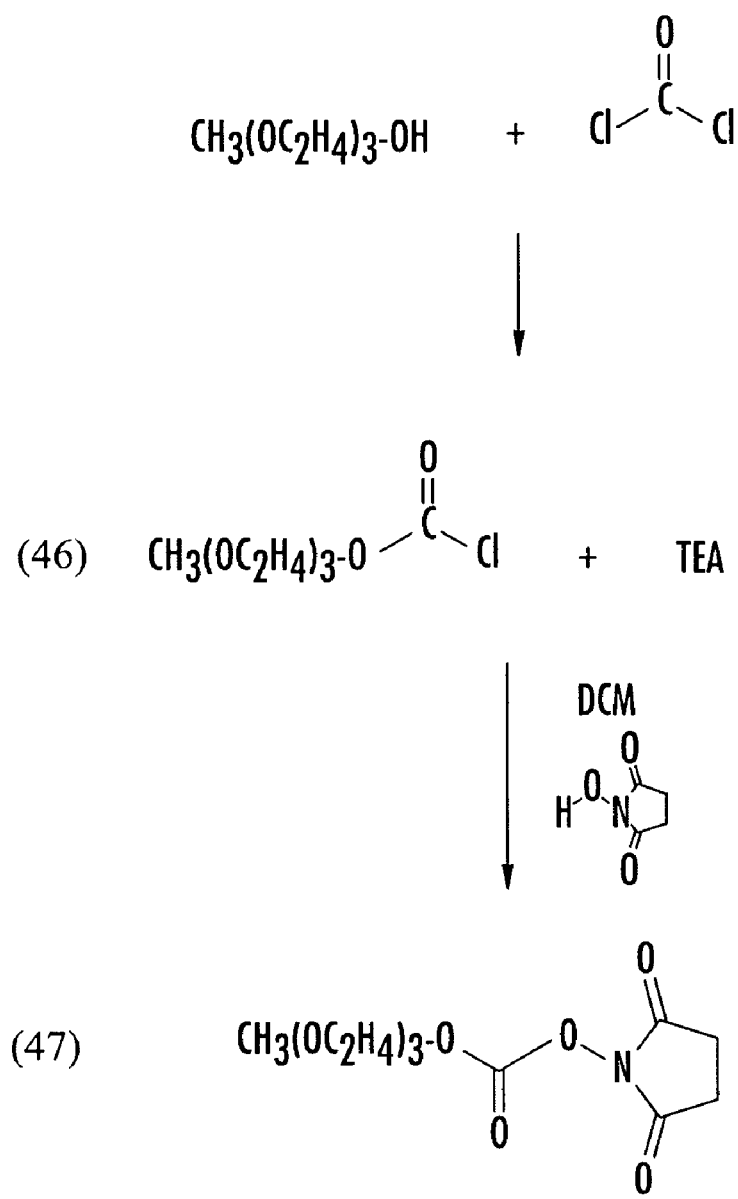
FIG. 8 illustrates a scheme for synthesizing a mixture of activated PEG3 oligomers according to embodiments of the present invention.
Figure 9:
FIG. 9 illustrates a scheme for synthesizing a mixture of activated palmitate-PEG3 oligomers according to embodiments of the present invention.
Figure 9:
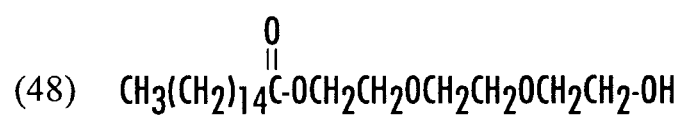
Figure 9:
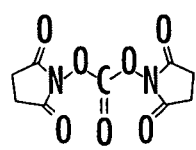
Figure 9:
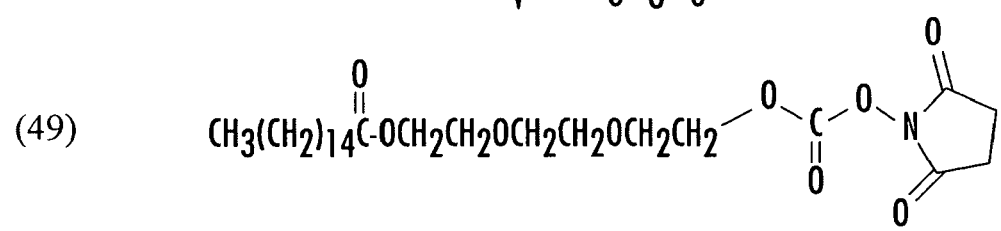
Figure 10:
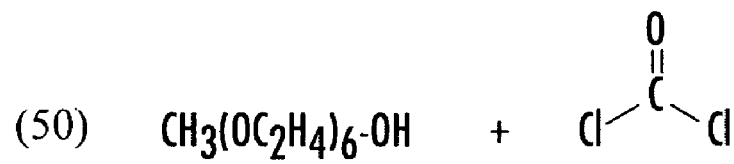
FIG. 10 illustrates a scheme for synthesizing a mixture of activated PEG6 oligomers according to embodiments of the present invention.
Figure 10:
Figure 10:
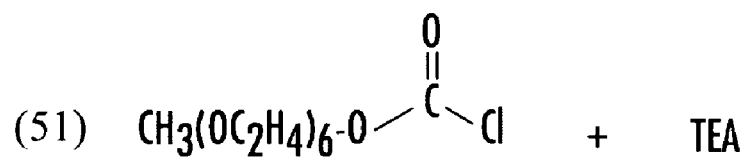
Figure 10:
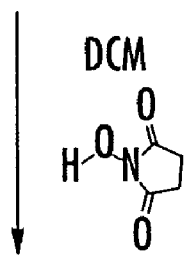
Figure 10:
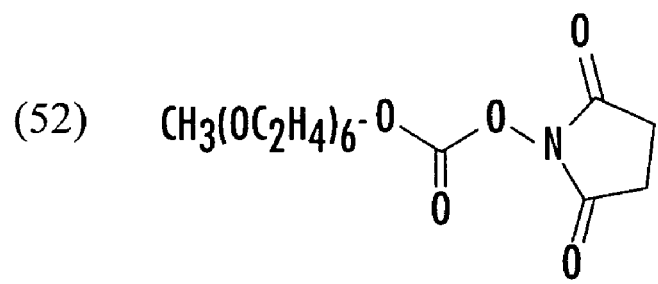

Substantially monodispersed mixtures of calcitonin drug-oligomer conjugates of the present invention may be synthesized by various methods. For example, a substantially monodispersed mixture of oligomers consisting of carboxylic acid and polyethylene glycol is synthesized by contacting a substantially monodispersed mixture of carboxylic acid with a substantially monodispersed mixture of polyethylene glycol under conditions sufficient to provide a substantially monodispersed mixture of oligomers. The oligomers of the substantially monodispersed mixture are then activated so that they are capable of reacting with a calcitonin drug to provide a calcitonin drug-oligomer conjugate. One embodiment of a synthesis route for providing a substantially monodispersed mixture of oligomers is illustrated in FIG. 3 and described in Examples 11–18 hereinbelow. Another embodiment of a synthesis route for providing a substantially monodispersed mixture of oligomers is illustrated in FIG. 4 and described in Examples 19–24 hereinbelow. Still another embodiment of a synthesis route for providing a substantially monodispersed mixture of oligomers is illustrated in FIG. 5 and described in Examples 25–29 hereinbelow. Yet another embodiment of a synthesis route for providing a substantially monodispersed mixture of oligomers is illustrated in FIG. 6 and described in Examples 30–31 hereinbelow. Another embodiment of a synthesis route for providing a substantially monodispersed mixture of oligomers is illustrated in FIG. 7 and described in Examples 32–37 hereinbelow. Still another embodiment of a synthesis route for providing a substantially monodispersed mixture of oligomers is illustrated in FIG. 8 and described in Example 38 hereinbelow. Yet another embodiment of a synthesis route for providing a substantially monodispersed mixture of oligomers is illustrated in FIG. 9 and described in Example 39 hereinbelow. Another embodiment of a synthesis route for providing a substantially monodispersed mixture of oligomers is illustrated in FIG. 10 and described in Example 40 hereinbelow.

The substantially monodispersed mixture of activated oligomers may be reacted with a substantially monodispersed mixture of calcitonin drugs under conditions sufficient to provide a mixture of calcitonin drug-oligomer conjugates. A preferred synthesis is described in Example 41 hereinbelow. As will be understood by those skilled in the art, the reaction conditions (e.g., selected molar ratios, solvent mixtures and/or pH) may be controlled such that the mixture of calcitonin drug-oligomer conjugates resulting from the reaction of the substantially monodispersed mixture of activated oligomers and the substantially monodispersed mixture of calcitonin drugs is a substantially monodispersed mixture. For example, conjugation at the amino functionality of lysine may be suppressed by maintaining the pH of the reaction solution below the $pK_a$ of lysine. Alternatively, the mixture of calcitonin drug-oligomer conjugates may be separated and isolated utilizing, for example, HPLC to provide a substantially monodispersed mixture of calcitonin drug-oligomer conjugates, for example mono-, di-, or tri-conjugates. The degree of conjugation (e.g., whether the isolated molecule is a mono-, di-, or tri-conjugate) of a particular isolated conjugate may be determined and/or verified utilizing various techniques as will be understood by those skilled in the art including, but not limited to, mass spectroscopy. The particular conjugate structure (e.g., whether the oligomer is at $Lys^{11}$, $Lys^{18}$ or the N-terminus of a salmon calcitonin monoconjugate) may be determined and/or verified utilizing various techniques as will be understood by those skilled in the art including, but not limited to, sequence analysis, peptide mapping, selective enzymatic cleavage, and/or endopeptidase cleavage.

As will be understood by those skilled in the art, one or more of the reaction sites on the calcitonin drug may be blocked by, for example, reacting the calcitonin drug with a suitable blocking reagent such as N-tert-butoxycarbonyl (t-BOC), or N-(9-fluorenylmethoxycarbonyl) (N-FMOC). This process may be preferred, for example, when the calcitonin drug is a polypeptide and it is desired to form an unsaturated conjugate (i.e., a conjugate wherein not all nucleophilic residues are conjugated) having an oligomer at the N-terminus of the polypeptide. Following such blocking, the substantially monodispersed mixture of blocked calcitonin drugs may be reacted with the substantially monodispersed mixture of activated oligomers to provide a mixture of calcitonin drug-oligomer conjugates having oligomer(s) coupled to one or more nucleophilic residues and having blocking moieties coupled to other nucleophilic residues. After the conjugation reaction, the calcitonin drug-oligomer conjugates may be de-blocked as will be understood by those skilled in the art. If necessary, the mixture of calcitonin drug-oligomer conjugates may then be separated as described above to provide a substantially monodispersed mixture of calcitonin drug-oligomer conjugates. Alternatively, the mixture of calcitonin drug-oligomer conjugates may be separated prior to de-blocking.

Substantially monodispersed mixtures of calcitonin drug-oligomer conjugates according to embodiments of the present invention preferably have improved properties when compared with those of conventional mixtures. For example, a substantially monodispersed mixture of calcitonin-oligomer conjugates preferably is capable of lowering serum calcium levels by at least 5 percent. Preferably, the mixture of conjugates is capable of lowering serum calcium levels by at least 10, 11, 12, 13 or 14 percent. More preferably, the mixture of conjugates is capable of lowering serum calcium levels by at least 15, 16, 17, 18 or 19 percent, and, most preferably, the mixture of conjugates is capable of lowering serum calcium levels by at least 20 percent.

As another example, a substantially monodispersed mixture of calcitonin-oligomer conjugates preferably has an increased resistance to degradation by chymotrypsin and/or trypsin when compared to the resistance to degradation by chymotrypsin and/or trypsin, respectively, of the calcitonin drug which is not coupled to the oligomer. Resistance to chymotrypsin or trypsin corresponds to the percent remaining when the molecule to be tested is digested in the applicable enzyme using the procedure outlined in Example 51 below. Preferably, the resistance to degradation by chymotrypsin of the mixture of calcitonin drug-oligomer conjugates is about 10 percent greater than the resistance to degradation by chymotrypsin of the mixture of calcitonin drugs that is not conjugated with the oligomer. More preferably, the resistance to degradation by chymotrypsin of the mixture of calcitonin drug-oligomer conjugates is about 15 percent greater than the resistance to degradation by chymotrypsin of the mixture of calcitonin drug that is not conjugated with the oligomer, and, most preferably, the resistance to degradation by chymotrypsin of the mixture of calcitonin drug-oligomer conjugates is about 20 percent greater than the resistance to degradation by chymotrypsin of the mixture of calcitonin drug that is not conjugated with the oligomer. Preferably, the resistance to degradation by trypsin of the mixture of calcitonin drug-oligomer conjugates is about 10 percent greater than the resistance to degradation by trypsin of the mixture of calcitonin drug that is not conjugated with the oligomer. More preferably, the resistance to degradation by trypsin of the mixture of calcitonin drug-oligomer conjugates is about 20 percent greater than the resistance to degradation by trypsin of the mixture of calcitonin drug that is not conjugated with the oligomer, and, most preferably, the resistance to degradation by trypsin of the mixture of calcitonin drug-oligomer conjugates is about 30 percent greater than the resistance to degradation by trypsin of the mixture of calcitonin drug that is not conjugated with the oligomer.

As still another example, a substantially monodispersed mixture of calcitonin-oligomer conjugates preferably has a higher bioefficacy than the bioefficacy of the calcitonin drug which is not coupled to the oligomer. The bioefficacy of a particular compound corresponds to its area-under-the-curve (AUC) value. Preferably, the bioefficacy of the mixture is about 5 percent greater than the bioefficacy of the calcitonin drug which is not coupled to the oligomer. More preferably, the bioefficacy of the mixture is about 10 percent greater than the bioefficacy of the calcitonin drug which is not coupled to the oligomer.

As yet another example, a substantially monodispersed mixture of calcitonin-oligomer conjugates preferably has an in vivo activity that is greater than the in vivo activity of a polydispersed mixture of calcitonin drug-oligomer conjugates having the same number average molecular weight as the substantially monodispersed mixture. As will be understood by those skilled in the art, the number average molecular weight of a mixture may be measured by various methods including, but not limited to, size exclusion chromatography such as gel permeation chromatography as described, for example, in H. R. Allcock & F. W. Lampe, CONTEMPORARY POLYMER CHEMISTRY 394–402 (2d. ed., 1991).

As another example, a substantially monodispersed mixture of calcitonin-oligomer conjugates preferably has an in vitro activity that is greater than the in vitro activity of a polydispersed mixture of calcitonin drug-oligomer conjugates having the same number average molecular weight as the substantially monodispersed mixture. As will be understood by those skilled in the art, the number average molecular weight of a mixture may be measured by various methods including, but not limited to, size exclusion chromatography.

As still another example, a substantially monodispersed mixture of calcitonin-oligomer conjugates preferably has an increased resistance to degradation by chymotrypsin and/or trypsin when compared to the resistance to degradation by chymotrypsin and/or trypsin of a polydispersed mixture of calcitonin drug-oligomer conjugates having the same number average molecular weight as the substantially monodispersed mixture. As will be understood by those skilled in the art, the number average molecular weight of a mixture may be measured by various methods including, but not limited to, size exclusion chromatography.

As yet another example, a substantially monodispersed mixture of calcitonin-oligomer conjugates preferably has an inter-subject variability that is less than the inter-subject variability of a polydispersed mixture of calcitonin drug-oligomer conjugates having the same number average molecular weight as the substantially monodispersed mixture. As will be understood by those skilled in the art, the number average molecular weight of a mixture may be measured by various methods including, but not limited to, size exclusion chromatography. The inter-subject variability may be measured by various methods, as will be understood by those skilled in the art. The inter-subject variability is preferably calculated as follows. The area under a dose response curve (AUC) (i.e., the area between the dose-response curve and a baseline value) is determined for each subject. The average AUC for all subjects is determined by summing the AUCs of each subject and dividing the sum by the number of subjects. The absolute value of the difference between the subject's AUC and the average AUC is then determined for each subject. The absolute values of the differences obtained are then summed to give a value that represents the inter-subject variability. Lower values represent lower inter-subject variabilities and higher values represent higher inter-subject variabilities.

Substantially monodispersed mixtures of calcitonin drug-oligomer conjugates according to embodiments of the present invention preferably have two or more of the above-described improved properties. More preferably, substantially monodispersed mixtures of calcitonin drug-oligomer conjugates according to embodiments of the present invention have three or more of the above-described improved properties. Most preferably, substantially monodispersed mixtures of calcitonin drug-oligomer conjugates according to embodiments of the present invention have four or more of the above-described improved properties.

In still other embodiments according to the present invention, a mixture of conjugates having a molecular weight distribution with a standard deviation of less than about 22 Daltons is provided. Each conjugate in the mixture includes a calcitonin drug coupled to an oligomer that comprises a polyethylene glycol moiety. The standard deviation is preferably less than about 14 Daltons and is more preferably less than about 11 Daltons. The molecular weight distribution may be determined by methods known to those skilled in the art including, but not limited to, size exclusion chromatography such as gel permeation chromatography as described, for example, in H. R. Allcock & F. W. Lampe, CONTEMPORARY POLYMER CHEMISTRY 394–402 (2d. ed., 1991). The standard deviation of the molecular weight distribution may then be determined by statistical methods as will be understood by those skilled in the art.

The calcitonin drug is preferably calcitonin. More preferably, the calcitonin drug is salmon calcitonin. However, it is to be understood that the calcitonin drug may be selected from various calcitonin drugs known to those skilled in the art including, for example, calcitonin precursor peptides, calcitonin, calcitonin analogs, calcitonin fragments, and calcitonin fragment analogs. Calcitonin precursor peptides include, but are not limited to, katacalcin (PDN-21) (C-procalcitonin), and N-proCT (amino-terminal procalcitonin cleavage peptide), human. Calcitonin analogs may be provided by substitution of one or more amino acids in calcitonin as described above. Calcitonin fragments include, but are not limited to, calcitonin 1–7, human; and calcitonin 8–32, salmon. Calcitonin fragment analogs may be provided by substitution of one or more of the amino acids in a calcitonin fragment as described above.

The oligomer may be various oligomers comprising a polyethylene glycol moiety as will be understood by those skilled in the art. Preferably, the polyethylene glycol moiety of the oligomer has at least 2, 3 or 4 polyethylene glycol subunits. More preferably, the polyethylene glycol moiety has at least 5 or 6 polyethylene glycol subunits and, most preferably, the polyethylene glycol moiety has at least 7 polyethylene glycol subunits.

The oligomer may comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The oligomer may further comprise one or more additional hydrophilic moieties (i.e., moieties in addition to the polyethylene glycol moiety) including, but not limited to, sugars, polyalkylene oxides, and polyamine/PEG copolymers. As polyethylene glycol is a polyalkylene oxide, the additional hydrophilic moiety may be a polyethylene glycol moiety. Adjacent polyethylene glycol moieties will be considered to be the same moiety if they are coupled by an ether bond. For example, the moiety

—O—C₂H₄—O—C₂H₄—O—C₂H₄—O —C₂H₄—O—C₂H₄—O—C₂H₄— is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties will be considered to be different moieties if they are coupled by a bond other than an ether bond. For example, the moiety

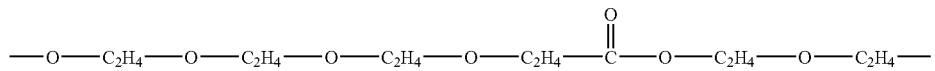

is a polyethylene glycol moiety having four polyethylene glycol subunits and an additional hydrophilic moiety having two polyethylene glycol subunits. Preferably, oligomers according to embodiments of the present invention comprise a polyethylene glycol moiety and no additional hydrophilic moieties.

The oligomer may further comprise one or more lipophilic moieties as will be understood by those skilled in the art. The lipophilic moiety is preferably a saturated or unsaturated, linear or branched alkyl moiety or a saturated or unsaturated, linear or branched fatty acid moiety. When the lipophilic moiety is an alkyl moiety, it is preferably a linear, saturated or unsaturated alkyl moiety having 1 to 28 carbon atoms. More preferably, the alkyl moiety has 2 to 12 carbon atoms. When the lipophilic moiety is a fatty acid moiety, it is preferably a natural fatty acid moiety that is linear, saturated or unsaturated, having 2 to 18 carbon atoms. More preferably, the fatty acid moiety has 3 to 14 carbon atoms. Most preferably, the fatty acid moiety has at least 4, 5 or 6 carbon atoms.

The oligomer may further comprise one or more spacer moieties as will be understood by those skilled in the art. Spacer moieties may, for example, be used to separate a hydrophilic moiety from a lipophilic moiety, to separate a lipophilic moiety or hydrophilic moiety from the calcitonin drug, to separate a first hydrophilic or lipophilic moiety from a second hydrophilic or lipophilic moiety, or to separate a hydrophilic moiety or lipophilic moiety from a linker moiety. Spacer moieties are preferably selected from the group consisting of sugar, cholesterol and glycerine moieties.

The oligomer may further comprise one or more linker moieties that are used to couple the oligomer with the calcitonin drug as will be understood by those skilled in the art. Linker moieties are preferably selected from the group consisting of alkyl and fatty acid moieties.

The oligomer may further comprise one or more terminating moieties at the one or more ends of the oligomer which are not coupled to the calcitonin drug. The terminating moiety is preferably an alkyl or alkoxy moiety, and is more preferably a lower alkyl or lower alkoxy moiety. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugars, cholesterol, alcohols, and fatty acids.

The oligomer is preferably covalently coupled to the calcitonin drug. In some embodiments, the calcitonin drug is coupled to the oligomer utilizing a hydrolyzable bond (e.g., an ester or carbonate bond). A hydrolyzable coupling may provide a calcitonin drug-oligomer conjugate that acts as a prodrug. In certain instances, for example where the calcitonin drug-oligomer conjugate is inactive (i.e., the conjugate lacks the ability to affect the body through the calcitonin drug's primary mechanism of action), a hydrolyzable coupling may provide for a time-release or controlled-release effect, administering the calcitonin drug over a given time period as one or more oligomers are cleaved from their respective calcitonin drug-oligomer conjugates to provide the active drug. In other embodiments, the calcitonin drug is coupled to the oligomer utilizing a non-hydrolyzable bond (e.g., a carbamate, amide, or ether bond). Use of a non-hydrolyzable bond may be preferable when it is desirable to allow the calcitonin drug-oligomer conjugate to circulate in the bloodstream for an extended period of time, preferably at least 2 hours. When the oligomer is covalently coupled to the calcitonin drug, the oligomer further comprises one or more bonding moieties that are used to covalently couple the oligomer with the calcitonin drug as will be understood by those skilled in the art. Bonding moieties are preferably selected from the group consisting of covalent bond(s), ester moieties, carbonate moieties, carbamate moieties, amide moieties and secondary amine moieties. More than one moiety on the oligomer may be covalently coupled to the calcitonin drug.

While the oligomer is preferably covalently coupled to the calcitonin drug, it is to be understood that the oligomer may be non-covalently coupled to the calcitonin drug to form a non-covalently conjugated calcitonin drug-oligomer complex. As will be understood by those skilled in the art, non-covalent couplings include, but are not limited to, hydrogen bonding, ionic bonding, Van der Waals bonding, and micellular or liposomal encapsulation. According to embodiments of the present invention, oligomers may be suitably constructed, modified and/or appropriately functionalized to impart the ability for non-covalent conjugation in a selected manner (e.g., to impart hydrogen bonding capability), as will be understood by those skilled in the art. According to other embodiments of present invention, oligomers may be derivatized with various compounds including, but not limited to, amino acids, oligopeptides, peptides, bile acids, bile acid derivatives, fatty acids, fatty acid derivatives, salicylic acids, salicylic acid derivatives, aminosalicylic acids, and aminosalicylic acid derivatives. The resulting oligomers can non-covalently couple (complex) with drug molecules, pharmaceutical products, and/or pharmaceutical excipients. The resulting complexes preferably have balanced lipophilic and hydrophilic properties. According to still other embodiments of the present invention, oligomers may be derivatized with amine and/or alkyl amines. Under suitable acidic conditions, the resulting oligomers can form non-covalently conjugated complexes with drug molecules, pharmaceutical products and/or pharmaceutical excipients. The products resulting from such complexation preferably have balanced lipophilic and hydrophilic properties.

More than one oligomer (i.e., a plurality of oligomers) may be coupled to the calcitonin drug. The oligomers in the plurality are preferably the same. However, it is to be understood that the oligomers in the plurality may be different from one another, or, alternatively, some of the oligomers in the plurality may be the same and some may be different. When a plurality of oligomers are coupled to the calcitonin drug, it may be preferable to couple one or more of the oligomers to the calcitonin drug with hydrolyzable bonds and couple one or more of the oligomers to the calcitonin drug with non-hydrolyzable bonds. Alternatively, all of the bonds coupling the plurality of oligomers to the calcitonin drug may be hydrolyzable, but have varying degrees of hydrolyzability such that, for example, one or more of the oligomers is rapidly removed from the calcitonin drug by hydrolysis in the body and one or more of the oligomers is slowly removed from the calcitonin drug by hydrolysis in the body.

The oligomer may be coupled to the calcitonin drug at various nucleophilic residues of the calcitonin drug including, but not limited to, nucleophilic hydroxyl functions and/or amino functions. When the calcitonin drug is a polypeptide, a nucleophilic hydroxyl function may be found, for example, at serine and/or tyrosine residues, and a nucleophilic amino function may be found, for example, at histidine and/or lysine residues, and/or at the one or more N-termini of the polypeptide. When an oligomer is coupled to the one or more N-terminus of the calcitonin polypeptide, the coupling preferably forms a secondary amine.

When the calcitonin drug is salmon calcitonin, for example, the oligomer may be coupled to an amino functionality of the salmon calcitonin, including the amino functionality of $Lys^{11}$, $Lys^{18}$ and/or the N-terminus. While one or more oligomers may be coupled to the salmon calcitonin, a higher bioefficacy, such as improved serum calcium lowering ability, is observed for the di-conjugated salmon calcitonin where an oligomer is coupled to the amino functionalities of $Lys^{11}$ and the $Lys^{18}$.

Mixtures of calcitonin drug-oligomer conjugates having a molecular weight distribution with a standard deviation of less than about 22 Daltons may be synthesized by various methods. For example, a mixture of oligomers having a molecular weight distribution with a standard deviation of less than about 22 Daltons consisting of carboxylic acid and polyethylene glycol is synthesized by contacting a mixture of carboxylic acid having a molecular weight distribution with a standard deviation of less than about 22 Daltons with a mixture of polyethylene glycol having a molecular weight distribution with a standard deviation of less than about 22 Daltons under conditions sufficient to provide a mixture of oligomers having a molecular weight distribution with a standard deviation of less than about 22 Daltons. The oligomers of the mixture having a molecular weight distribution with a standard deviation of less than about 22 Daltons are then activated so that they are capable of reacting with a calcitonin drug to provide a calcitonin drug-oligomer conjugate. One embodiment of a synthesis route for providing a mixture of activated oligomers having a molecular weight distribution with a standard deviation of less than about 22 Daltons is illustrated in FIG. 3 and described in Examples 11–18 hereinbelow. Another embodiment of a synthesis route for providing a mixture of activated oligomers having a molecular weight distribution with a standard deviation of less than about 22 Daltons is illustrated in FIG. 4 and described in Examples 19–24 hereinbelow. Still another embodiment of a synthesis route for providing a mixture of activated oligomers having a molecular weight distribution with a standard deviation of less than about 22 Daltons is illustrated in FIG. 5 and described in Examples 25–29 hereinbelow. Yet another embodiment of a synthesis route for providing a mixture of activated oligomers having a molecular weight distribution with a standard deviation of less than about 22 Daltons is illustrated in FIG. 6 and described in Examples 30–31 hereinbelow. Another embodiment of a synthesis route for providing a mixture of activated oligomers having a molecular weight distribution with a standard deviation of less than about 22 Daltons is illustrated in FIG. 7 and described in Examples 32–37 hereinbelow. Still another embodiment of a synthesis route for providing a mixture of activated oligomers having a molecular weight distribution with a standard deviation of less than about 22 Daltons is illustrated in FIG. 8 and described in Example 38 hereinbelow. Yet another embodiment of a synthesis route for providing a mixture of activated oligomers having a molecular weight distribution with a standard deviation of less than about 22 Daltons is illustrated in FIG. 9 and described in Example 39 hereinbelow. Another embodiment of a synthesis route for providing a mixture of activated oligomers having a molecular weight distribution with a standard deviation of less than about 22 Daltons is illustrated in FIG. 10 and described in Example 40 hereinbelow.

The mixture of activated oligomers having a molecular weight distribution with a standard deviation of less than about 22 Daltons is reacted with a mixture of calcitonin drugs having a molecular weight distribution with a standard deviation of less than about 22 Daltons under conditions sufficient to provide a mixture of calcitonin drug-oligomer conjugates. A preferred synthesis is described in Example 41 hereinbelow. As will be understood by those skilled in the art, the reaction conditions (e.g., selected molar ratios, solvent mixtures and/or pH) may be controlled such that the mixture of calcitonin drug-oligomer conjugates resulting from the reaction of the mixture of activated oligomers having a molecular weight distribution with a standard deviation of less than about 22 Daltons and the mixture of calcitonin drugs having a molecular weight distribution with a standard deviation of less than about 22 Daltons is a mixture having a molecular weight distribution with a standard deviation of less than about 22 Daltons. For example, conjugation at the amino functionality of lysine may be suppressed by maintaining the pH of the reaction solution below the $pK_a$ of lysine. Alternatively, the mixture of calcitonin drug-oligomer conjugates may be separated and isolated utilizing, for example, HPLC to provide a mixture of calcitonin drug-oligomer conjugates, for example mono-, di-, or tri-conjugates, having a molecular weight distribution with a standard deviation of less than about 22 Daltons. The degree of conjugation (e.g., whether the isolated molecule is a mono-, di-, or tri-conjugate) of a particular isolated conjugate may be determined and/or verified utilizing various techniques as will be understood by those skilled in the art including, but not limited to, mass spectroscopy. The particular conjugate structure (e.g., whether the oligomer is at $Lys^{11}$, $Lys^{18}$ or the N-terminus of a salmon calcitonin monoconjugate) may be determined and/or verified utilizing various techniques as will be understood by those skilled in the art including, but not limited to, sequence analysis, peptide mapping, selective enzymatic cleavage, and/or endopeptidase cleavage.

As will be understood by those skilled in the art, one or more of the reaction sites on the calcitonin drug may be blocked by, for example, reacting the calcitonin drug with a suitable blocking reagent such as N-tert-butoxycarbonyl (t-BOC), or N-(9-fluorenylmethoxycarbonyl) (N-FMOC). This process may be preferred, for example, when the calcitonin drug is a polypeptide and it is desired to form an unsaturated conjugate (i.e., a conjugate wherein not all nucleophilic residues are conjugated) having an oligomer at the N-terminus of the polypeptide. Following such blocking, the mixture of blocked calcitonin drugs having a molecular weight distribution with a standard deviation of less than about 22 Daltons may be reacted with the mixture of activated oligomers having a molecular weight distribution with a standard deviation of less than about 22 Daltons to provide a mixture of calcitonin drug-oligomer conjugates having oligomer(s) coupled to one or more nucleophilic residues and having blocking moieties coupled to other nucleophilic residues. After the conjugation reaction, the calcitonin drug-oligomer conjugates may be de-blocked as will be understood by those skilled in the art. If necessary, the mixture of calcitonin drug-oligomer conjugates may then be separated as described above to provide a mixture of calcitonin drug-oligomer conjugates having a molecular weight distribution with a standard deviation of less than about 22 Daltons. Alternatively, the mixture of calcitonin drug-oligomer conjugates may be separated prior to de-blocking.

Mixtures of calcitonin drug-oligomer conjugates having a molecular weight distribution with a standard deviation of less than about 22 Daltons according to embodiments of the present invention preferably have improved properties when compared with those of conventional mixtures. For example, a mixture of calcitonin drug-oligomer conjugates having a molecular weight distribution with a standard deviation of less than about 22 Daltons preferably is capable of lowering serum calcium levels by at least 5 percent. Preferably, the mixture of conjugates is capable of lowering serum calcium levels by at least 10, 11, 12, 13 or 14 percent. More preferably, the mixture of conjugates is capable of lowering serum calcium levels by at least 15, 16, 17, 18 or 19 percent, and, most preferably, the mixture of conjugates is capable of lowering serum calcium levels by at least 20 percent.

As another example, a mixture of calcitonin drug-oligomer conjugates having a molecular weight distribution with a standard deviation of less than about 22 Daltons preferably has an increased resistance to degradation by chymotrypsin and/or trypsin when compared to the resistance to degradation by chymotrypsin and/or trypsin, respectively, of the calcitonin drug which is not coupled to the oligomer. Resistance to chymotrypsin or trypsin corresponds to the percent remaining when the molecule to be tested is digested in the applicable enzyme using a procedure similar to the one outlined in Example 51 below. Preferably, the resistance to degradation by chymotrypsin of the mixture of calcitonin drug-oligomer conjugates is about 10 percent greater than the resistance to degradation by chymotrypsin of the mixture of calcitonin drugs that is not conjugated with the oligomer. More preferably, the resistance to degradation by chymotrypsin of the mixture of calcitonin drug-oligomer conjugates is about 15 percent greater than the resistance to degradation by chymotrypsin of the mixture of calcitonin drug that is not conjugated with the oligomer, and, most preferably, the resistance to degradation by chymotrypsin of the mixture of calcitonin drug-oligomer conjugates is about 20 percent greater than the resistance to degradation by chymotrypsin of the mixture of calcitonin drug that is not conjugated with the oligomer. Preferably, the resistance to degradation by trypsin of the mixture of calcitonin drug-oligomer conjugates is about 10 percent greater than the resistance to degradation by trypsin of the mixture of calcitonin drug that is not conjugated with the oligomer. More preferably, the resistance to degradation by trypsin of the mixture of calcitonin drug-oligomer conjugates is about 20 percent greater than the resistance to degradation by trypsin of the mixture of calcitonin drug that is not conjugated with the oligomer, and, most preferably, the resistance to degradation by trypsin of the mixture of calcitonin drug-oligomer conjugates is about 30 percent greater than the resistance to degradation by trypsin of the mixture of calcitonin drug that is not conjugated with the oligomer.

As still another example, a mixture of calcitonin drug-oligomer conjugates having a molecular weight distribution with a standard deviation of less than about 22 Daltons preferably has a higher bioefficacy than the bioefficacy of the calcitonin drug which is not coupled to the oligomer. The bioefficacy of a particular compound corresponds to its area-under-the-curve (AUC) value. Preferably, the bioefficacy of the mixture is about 5 percent greater than the bioefficacy of the calcitonin drug which is not coupled to the oligomer. More preferably, the bioefficacy of the mixture is about 10 percent greater than the bioefficacy of the calcitonin drug which is not coupled to the oligomer.

As yet another example, a mixture of calcitonin drug-oligomer conjugates having a molecular weight distribution with a standard deviation of less than about 22 Daltons preferably has an in vivo activity that is greater than the in vivo activity of a polydispersed mixture of calcitonin drug-oligomer conjugates having the same number average molecular weight as the mixture of calcitonin drug-oligomer conjugates having a molecular weight distribution with a standard deviation of less than about 22 Daltons. As will be understood by those skilled in the art, the number average molecular weight of a mixture may be measured by various methods including, but not limited to, size exclusion chromatography such as gel permeation chromatography as described, for example, in H. R. Allcock & F. W. Lampe, CONTEMPORARY POLYMER CHEMISTRY 394–402 (2d. ed., 1991).

As another example, a mixture of calcitonin drug-oligomer conjugates having a molecular weight distribution with a standard deviation of less than about 22 Daltons preferably has an in vitro activity that is greater than the in vitro activity of a polydispersed mixture of calcitonin drug-oligomer conjugates having the same number average molecular weight as the mixture of calcitonin drug-oligomer conjugates having a molecular weight distribution with a standard deviation of less than about 22 Daltons. As will be understood by those skilled in the art, the number average molecular weight of a mixture may be measured by various methods including, but not limited to, size exclusion chromatography.

As still another example, a mixture of calcitonin drug-oligomer conjugates having a molecular weight distribution with a standard deviation of less than about 22 Daltons preferably has an increased resistance to degradation by chymotrypsin and/or trypsin when compared to the resistance to degradation by chymotrypsin and/or trypsin of a polydispersed mixture of calcitonin drug-oligomer conjugates having the same number average molecular weight as the mixture of calcitonin drug-oligomer conjugates having a molecular weight distribution with a standard deviation of less than about 22 Daltons. As will be understood by those skilled in the art, the number average molecular weight of a mixture may be measured by various methods including, but not limited to, size exclusion chromatography.

As yet another example, a mixture of calcitonin drug-oligomer conjugates having a molecular weight distribution with a standard deviation of less than about 22 Daltons preferably has an inter-subject variability that is less than the inter-subject variability of a polydispersed mixture of calcitonin drug-oligomer conjugates having the same number average molecular weight as the mixture of calcitonin drug-oligomer conjugates having a molecular weight distribution with a standard deviation of less than about 22 Daltons. As will be understood by those skilled in the art, the number average molecular weight of a mixture may be measured by various methods including, but not limited to, size exclusion chromatography. The inter-subject variability may be measured by various methods, as will be understood by those skilled in the art. The inter-subject variability is preferably calculated as follows. The area under a dose response curve (AUC) (i.e., the area between the dose-response curve and a baseline value) is determined for each subject. The average AUC for all subjects is determined by summing the AUCs of each subject and dividing the sum by the number of subjects. The absolute value of the difference between the subject's AUC and the average AUC is then determined for each subject. The absolute values of the differences obtained are then summed to give a value that represents the inter-subject variability. Lower values represent lower inter-subject variabilities and higher values represent higher inter-subject variabilities.

Mixtures of calcitonin drug-oligomer conjugates having a molecular weight distribution with a standard deviation of less than about 22 Daltons according to embodiments of the present invention preferably have two or more of the above-described improved properties. More preferably, mixtures of calcitonin drug-oligomer conjugates having a molecular weight distribution with a standard deviation of less than about 22 Daltons according to embodiments of the present invention have three or more of the above-described improved properties. Most preferably, mixtures of calcitonin drug-oligomer conjugates having a molecular weight distribution with a standard deviation of less than about 22 Daltons according to embodiments of the present invention have four or more of the above-described improved properties.

According to yet other embodiments of the present invention, a mixture of conjugates is provided where each conjugate includes a calcitonin drug coupled to an oligomer comprising a polyethylene glycol moiety, and the mixture has a dispersity coefficient (DC) greater than 10,000 where $$DC = \frac{\left(\sum_{i=1}^{n} N_i M_i\right)^2}{\sum_{i=1}^{n} N_i M_i^2 \sum_{i=1}^{n} N_i - \left(\sum_{i=1}^{n} N_i M_i\right)^2}$$

wherein:

n is the number of different molecules in the sample;

$N_i$ is the number of $i^{th}$ molecules in the sample; and $M_i$ is the mass of the $i^{th}$ molecule.

The mixture of conjugates preferably has a dispersity coefficient greater than 100,000. More preferably, the dispersity coefficient of the conjugate mixture is greater than 500,000 and, most preferably, the dispersity coefficient is greater than 10,000,000. The variables n, $N_i$, and $M_i$ may be determined by various methods as will be understood by those skilled in the art, including, but not limited to, methods described below in Example 49.

The calcitonin drug is preferably calcitonin. More preferably, the calcitonin drug is salmon calcitonin. However, it is to be understood that the calcitonin drug may be selected from various calcitonin drugs known to those skilled in the art including, for example, calcitonin precursor peptides, calcitonin, calcitonin analogs, calcitonin fragments, and calcitonin fragment analogs. Calcitonin precursor peptides include, but are not limited to, katacalcin (PDN-21) (C-procalcitonin), and N-proCT (amino-terminal procalcitonin cleavage peptide), human. Calcitonin analogs may be provided by substitution of one or more amino acids in calcitonin as described above. Calcitonin fragments include, but are not limited to, calcitonin 1–7, human; and calcitonin 8–32, salmon. Calcitonin fragment analogs may be provided by substitution of one or more of the amino acids in a calcitonin fragment as described above.

The oligomer may be various oligomers comprising a polyethylene glycol moiety as will be understood by those skilled in the art. Preferably, the polyethylene glycol moiety of the oligomer has at least 2, 3 or 4 polyethylene glycol subunits. More preferably, the polyethylene glycol moiety has at least 5 or 6 polyethylene glycol subunits and, most preferably, the polyethylene glycol moiety has at least 7 polyethylene glycol subunits.

The oligomer may comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The oligomer may further comprise one or more additional hydrophilic moieties (i.e., moieties in addition to the polyethylene glycol moiety) including, but not limited to, sugars, polyalkylene oxides, and polyamine/PEG copolymers. As polyethylene glycol is a polyalkylene oxide, the additional hydrophilic moiety may be a polyethylene glycol moiety. Adjacent polyethylene glycol moieties will be considered to be the same moiety if they are coupled by an ether bond. For example, the moiety $$-O-C_2H_4-O-C_2H_4-O-C_2H_4-O-C_2H_4-$$
$$O-C_2H_4-O-C_2H_4-$$

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties will be considered to be different moieties if they are coupled by a bond other than an ether bond. For example, the moiety $$-O-C_2H_4-O-C_2H_4-O-C_2H_4-O-C_2H_4-\overset{\overset{O}{\|}}{C}-O-C_2H_4-O-C_2H_4-$$

is a polyethylene glycol moiety having four polyethylene glycol subunits and an additional hydrophilic moiety having two polyethylene glycol subunits. Preferably, oligomers according to embodiments of the present invention comprise a polyethylene glycol moiety and no additional hydrophilic moieties.

The oligomer may further comprise one or more lipophilic moieties as will be understood by those skilled in the art. The lipophilic moiety is preferably a saturated or unsaturated, linear or branched alkyl moiety or a saturated or unsaturated, linear or branched fatty acid moiety. When the lipophilic moiety is an alkyl moiety, it is preferably a linear, saturated or unsaturated alkyl moiety having 1 to 28 carbon atoms. More preferably, the alkyl moiety has 2 to 12 carbon atoms. When the lipophilic moiety is a fatty acid moiety, it is preferably a natural fatty acid moiety that is linear, saturated or unsaturated, having 2 to 18 carbon atoms. More preferably, the fatty acid moiety has 3 to 14 carbon atoms. Most preferably, the fatty acid moiety has at least 4, 5 or 6 carbon atoms.

The oligomer may further comprise one or more spacer moieties as will be understood by those skilled in the art. Spacer moieties may, for example, be used to separate a hydrophilic moiety from a lipophilic moiety, to separate a lipophilic moiety or hydrophilic moiety from the calcitonin drug, to separate a first hydrophilic or lipophilic moiety from a second hydrophilic or lipophilic moiety, or to separate a hydrophilic moiety or lipophilic moiety from a linker moiety. Spacer moieties are preferably selected from the group consisting of sugar, cholesterol and glycerine moieties.

The oligomer may further comprise one or more linker moieties that are used to couple the oligomer with the calcitonin drug as will be understood by those skilled in the art. Linker moieties are preferably selected from the group consisting of alkyl and fatty acid moieties.

The oligomer may further comprise one or more terminating moieties at the one or more ends of the oligomer which are not coupled to the calcitonin drug. The terminating moiety is preferably an alkyl or alkoxy moiety, and is more preferably a lower alkyl or lower alkoxy moiety. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugars, cholesterol, alcohols, and fatty acids.

The oligomer is preferably covalently coupled to the calcitonin drug. In some embodiments, the calcitonin drug is coupled to the oligomer utilizing a hydrolyzable bond (e.g., an ester or carbonate bond). A hydrolyzable coupling may provide a calcitonin drug-oligomer conjugate that acts as a prodrug. In certain instances, for example where the calcitonin drug-oligomer conjugate is inactive (i.e., the conjugate lacks the ability to affect the body through the calcitonin drug's primary mechanism of action), a hydrolyzable coupling may provide for a time-release or controlled-release effect, administering the calcitonin drug over a given time period as one or more oligomers are cleaved from their respective calcitonin drug-oligomer conjugates to provide the active drug. In other embodiments, the calcitonin drug is coupled to the oligomer utilizing a non-hydrolyzable bond (e.g., a carbamate, amide, or ether bond). Use of a non-hydrolyzable bond may be preferable when it is desirable to allow the calcitonin drug-oligomer conjugate to circulate in the bloodstream for an extended period of time, preferably at least 2 hours. When the oligomer is covalently coupled to the calcitonin drug, the oligomer further comprises one or more bonding moieties that are used to covalently couple the oligomer with the calcitonin drug as will be understood by those skilled in the art. Bonding moieties are preferably selected from the group consisting of covalent bond(s), ester moieties, carbonate moieties, carbamate moieties, amide moieties and secondary amine moieties. More than one moiety on the oligomer may be covalently coupled to the calcitonin drug.

While the oligomer is preferably covalently coupled to the calcitonin drug, it is to be understood that the oligomer may be non-covalently coupled to the calcitonin drug to form a non-covalently conjugated calcitonin drug-oligomer complex. As will be understood by those skilled in the art, non-covalent couplings include, but are not limited to, hydrogen bonding, ionic bonding, Van der Waals bonding, and micellular or liposomal encapsulation. According to embodiments of the present invention, oligomers may be suitably constructed, modified and/or appropriately functionalized to impart the ability for non-covalent conjugation in a selected manner (e.g., to impart hydrogen bonding capability), as will be understood by those skilled in the art. According to other embodiments of present invention, oligomers may be derivatized with various compounds including, but not limited to, amino acids, oligopeptides, peptides, bile acids, bile acid derivatives, fatty acids, fatty acid derivatives, salicylic acids, salicylic acid derivatives, aminosalicylic acids, and aminosalicylic acid derivatives. The resulting oligomers can non-covalently couple (complex) with drug molecules, pharmaceutical products, and/or pharmaceutical excipients. The resulting complexes preferably have balanced lipophilic and hydrophilic properties. According to still other embodiments of the present invention, oligomers may be derivatized with amine and/or alkyl amines. Under suitable acidic conditions, the resulting oligomers can form non-covalently conjugated complexes with drug molecules, pharmaceutical products and/or pharmaceutical excipients. The products resulting from such complexation preferably have balanced lipophilic and hydrophilic properties.

More than one oligomer (i.e., a plurality of oligomers) may be coupled to the calcitonin drug. The oligomers in the plurality are preferably the same. However, it is to be understood that the oligomers in the plurality may be different from one another, or, alternatively, some of the oligomers in the plurality may be the same and some may be different. When a plurality of oligomers are coupled to the calcitonin drug, it may be preferable to couple one or more of the oligomers to the calcitonin drug with hydrolyzable bonds and couple one or more of the oligomers to the calcitonin drug with non-hydrolyzable bonds. Alternatively, all of the bonds coupling the plurality of oligomers to the calcitonin drug may be hydrolyzable, but have varying degrees of hydrolyzability such that, for example, one or more of the oligomers is rapidly removed from the calcitonin drug by hydrolysis in the body and one or more of the oligomers is slowly removed from the calcitonin drug by hydrolysis in the body.

The oligomer may be coupled to the calcitonin drug at various nucleophilic residues of the calcitonin drug including, but not limited to, nucleophilic hydroxyl functions and/or amino functions. When the calcitonin drug is a polypeptide, a nucleophilic hydroxyl function may be found, for example, at serine and/or tyrosine residues, and a nucleophilic amino function may be found, for example, at histidine and/or lysine residues, and/or at the one or more N-termini of the polypeptide. When an oligomer is coupled to the one or more N-terminus of the calcitonin polypeptide, the coupling preferably forms a secondary amine. When the calcitonin drug is salmon calcitonin, for example, the oligomer may be coupled to an amino functionality of the salmon calcitonin, including the amino functionality of $Lys^{11}$, $Lys^{18}$ and/or the N-terminus. While one or more oligomers may be coupled to the salmon calcitonin, a higher bioefficacy, such as improved serum calcium lowering ability, is observed for the di-conjugated salmon calcitonin where an oligomer is coupled to the amino functionalities of $Lys^{11}$ and the $Lys^{18}$.

Mixtures of calcitonin drug-oligomer conjugates having a dispersity coefficient greater than 10,000 may be synthesized by various methods. For example, a mixture of oligomers having a dispersity coefficient greater than 10,000 consisting of carboxylic acid and polyethylene glycol is synthesized by contacting a mixture of carboxylic acid having a dispersity coefficient greater than 10,000 with a mixture of polyethylene glycol having a dispersity coefficient greater than 10,000 under conditions sufficient to provide a mixture of oligomers having a dispersity coefficient greater than 10,000. The oligomers of the mixture having a dispersity coefficient greater than 10,000 are then activated so that they are capable of reacting with a calcitonin drug to provide a calcitonin drug-oligomer conjugate. One embodiment of a synthesis route for providing a mixture of activated oligomers having a dispersity coefficient greater than 10,000 is illustrated in FIG. 3 and described in Examples 11–18 hereinbelow. Another embodiment of a synthesis route for providing a mixture of activated oligomers having a dispersity coefficient greater than 10,000 is illustrated in FIG. 4 and described in Examples 19–24 hereinbelow. Still another embodiment of a synthesis route for providing a mixture of activated oligomers having a dispersity coefficient greater than 10,000 is illustrated in FIG. 5 and described in Examples 25–29 hereinbelow. Yet another embodiment of a synthesis route for providing a mixture of activated oligomers having a dispersity coefficient greater than 10,000 is illustrated in FIG. 6 and described in Examples 30–31 hereinbelow. Another embodiment of a synthesis route for providing a mixture of activated oligomers having a dispersity coefficient greater than 10,000 is illustrated in FIG. 7 and described in Examples 32–37 hereinbelow. Still another embodiment of a synthesis route for providing a mixture of activated oligomers having a dispersity coefficient greater than 10,000 is illustrated in FIG. 8 and described in Example 38 hereinbelow. Yet another embodiment of a synthesis route for providing a mixture of activated oligomers having a dispersity coefficient greater than 10,000 is illustrated in FIG. 9 and described in Example 39 hereinbelow. Another embodiment of a synthesis route for providing a mixture of activated oligomers having a dispersity coefficient greater than 10,000 is illustrated in FIG. 10 and described in Example 40 hereinbelow.

The mixture of activated oligomers having a dispersity coefficient greater than 10,000 is reacted with a mixture of calcitonin drugs having a dispersity coefficient greater than 10,000 under conditions sufficient to provide a mixture of calcitonin drug-oligomer conjugates. A preferred synthesis is described in Example 41 hereinbelow. As will be understood by those skilled in the art, the reaction conditions (e.g., selected molar ratios, solvent mixtures and/or pH) may be controlled such that the mixture of calcitonin drug-oligomer conjugates resulting from the reaction of the mixture of activated oligomers having a dispersity coefficient greater than 10,000 and the mixture of calcitonin drugs having a dispersity coefficient greater than 10,000 is a mixture having a dispersity coefficient greater than 10,000. For example, conjugation at the amino functionality of lysine may be suppressed by maintaining the pH of the reaction solution below the $pK_a$ of lysine. Alternatively, the mixture of calcitonin drug-oligomer conjugates may be separated and isolated utilizing, for example, HPLC to provide a mixture of calcitonin drug-oligomer conjugates, for example mono-, di-, or tri-conjugates, having a dispersity coefficient greater than 10,000. The degree of conjugation (e.g., whether the isolated molecule is a mono-, di-, or tri-conjugate) of a particular isolated conjugate may be determined and/or verified utilizing various techniques as will be understood by those skilled in the art including, but not limited to, mass spectroscopy. The particular conjugate structure (e.g., whether the oligomer is at $Lys^{11}$, $Lys^{18}$ or the N-terminus of a salmon calcitonin monoconjugate) may be determined and/or verified utilizing various techniques as will be understood by those skilled in the art including, but not limited to, sequence analysis, peptide mapping, selective enzymatic cleavage, and/or endopeptidase cleavage.

As will be understood by those skilled in the art, one or more of the reaction sites on the calcitonin drug may be blocked by, for example, reacting the calcitonin drug with a suitable blocking reagent such as N-tert-butoxycarbonyl (t-BOC), or N-(9-fluorenylmethoxycarbonyl) (N-FMOC). This process may be preferred, for example, when the calcitonin drug is a polypeptide and it is desired to form an unsaturated conjugate (i.e., a conjugate wherein not all nucleophilic residues are conjugated) having an oligomer at the N-terminus of the polypeptide. Following such blocking, the mixture of blocked calcitonin drugs having a dispersity coefficient greater than 10,000 may be reacted with the mixture of activated oligomers having a dispersity coefficient greater than 10,000 to provide a mixture of calcitonin drug-oligomer conjugates having oligomer(s) coupled to one or more nucleophilic residues and having blocking moieties coupled to other nucleophilic residues. After the conjugation reaction, the calcitonin drug-oligomer conjugates may be de-blocked as will be understood by those skilled in the art. If necessary, the mixture of calcitonin drug-oligomer conjugates may then be separated as described above to provide a mixture of calcitonin drug-oligomer conjugates having a dispersity coefficient greater than 10,000. Alternatively, the mixture of calcitonin drug-oligomer conjugates may be separated prior to de-blocking.

Mixtures of calcitonin drug-oligomer conjugates having a dispersity coefficient greater than 10,000 according to embodiments of the present invention preferably have improved properties when compared with those of conventional mixtures. For example, a mixture of calcitonin drug-oligomer conjugates having a dispersity coefficient greater than 10,000 preferably is capable of lowering serum calcium levels by at least 5 percent. Preferably, the mixture of conjugates is capable of lowering serum calcium levels by at least 10, 11, 12, 13 or 14 percent. More preferably, the mixture of conjugates is capable of lowering serum calcium levels by at least 15, 16, 17, 18 or 19 percent, and, most preferably, the mixture of conjugates is capable of lowering serum calcium levels by at least 20 percent.

As another example, a mixture of calcitonin drug-oligomer conjugates having a dispersity coefficient greater than 10,000 preferably has an increased resistance to degradation by chymotrypsin and/or trypsin when compared to the resistance to degradation by chymotrypsin and/or trypsin, respectively, of the calcitonin drug which is not coupled to the oligomer. Resistance to chymotrypsin or trypsin corresponds to the percent remaining when the molecule to be tested is digested in the applicable enzyme using a procedure similar to the one outlined in Example 51 below. Preferably, the resistance to degradation by chymotrypsin of the mixture of calcitonin drug-oligomer conjugates is about 10 percent greater than the resistance to degradation by chymotrypsin of the mixture of calcitonin drugs that is not conjugated with the oligomer. More preferably, the resistance to degradation by chymotrypsin of the mixture of calcitonin drug-oligomer conjugates is about 15 percent greater than the resistance to degradation by chymotrypsin of the mixture of calcitonin drug that is not conjugated with the oligomer, and, most preferably, the resistance to degradation by chymotrypsin of the mixture of calcitonin drug-oligomer conjugates is about 20 percent greater than the resistance to degradation by chymotrypsin of the mixture of calcitonin drug that is not conjugated with the oligomer. Preferably, the resistance to degradation by trypsin of the mixture of calcitonin drug-oligomer conjugates is about 10 percent greater than the resistance to degradation by trypsin of the mixture of calcitonin drug that is not conjugated with the oligomer. More preferably, the resistance to degradation by trypsin of the mixture of calcitonin drug-oligomer conjugates is about 20 percent greater than the resistance to degradation by trypsin of the mixture of calcitonin drug that is not conjugated with the oligomer, and, most preferably, the resistance to degradation by trypsin of the mixture of calcitonin drug-oligomer conjugates is about 30 percent greater than the resistance to degradation by trypsin of the mixture of calcitonin drug that is not conjugated with the oligomer.

As still another example, a mixture of calcitonin drug-oligomer conjugates having a dispersity coefficient greater than 10,000 preferably has a higher bioefficacy than the bioefficacy of the calcitonin drug which is not coupled to the oligomer. The bioefficacy of a particular compound corresponds to its area-under-the-curve (AUC) value. Preferably, the bioefficacy of the mixture is about 5 percent greater than the bioefficacy of the calcitonin drug which is not coupled to the oligomer. More preferably, the bioefficacy of the mixture is about 10 percent greater than the bioefficacy of the calcitonin drug which is not coupled to the oligomer.

A yet another example, a mixture of calcitonin drug-oligomer conjugates having a dispersity coefficient greater than 10,000 preferably has an in vivo activity that is greater than the in vivo activity of a polydispersed mixture of calcitonin drug-oligomer conjugates having the same number average molecular weight as the mixture of calcitonin drug-oligomer conjugates having a dispersity coefficient greater than 10,000. As will be understood by those skilled in the art, the number average molecular weight of a mixture may be measured by various methods including, but not limited to, size exclusion chromatography such as gel permeation chromatography as described, for example, in H. R. Allcock & F. W. Lampe, CONTEMPORARY POLYMER CHEMISTRY 394–402 (2d. ed., 1991).

As another example, a mixture of calcitonin drug-oligomer conjugates having a dispersity coefficient greater than 10,000 preferably has an in vitro activity that is greater than the in vitro activity of a polydispersed mixture of calcitonin drug-oligomer conjugates having the same number average molecular weight as the mixture of calcitonin drug-oligomer conjugates having a dispersity coefficient greater than 10,000. As will be understood by those skilled in the art, the number average molecular weight of a mixture may be measured by various methods including, but not limited to, size exclusion chromatography.

As still another example, a mixture of calcitonin drug-oligomer conjugates having a dispersity coefficient greater than 10,000 preferably has an increased resistance to degradation by chymotrypsin and/or trypsin when compared to the resistance to degradation by chymotrypsin and/or trypsin of a polydispersed mixture of calcitonin drug-oligomer conjugates having the same number average molecular weight as the mixture of calcitonin drug-oligomer conjugates having a dispersity coefficient greater than 10,000. As will be understood by those skilled in the art, the number average molecular weight of a mixture may be measured by various methods including, but not limited to, size exclusion chromatography.

As yet another example, a mixture of calcitonin drug-oligomer conjugates having a dispersity coefficient greater than 10,000 preferably has an inter-subject variability that is less than the inter-subject variability of a polydispersed mixture of calcitonin drug-oligomer conjugates having the same number average molecular weight as the mixture of calcitonin drug-oligomer conjugates having a dispersity coefficient greater than 10,000. As will be understood by those skilled in the art, the number average molecular weight of a mixture may be measured by various methods including, but not limited to, size exclusion chromatography. The inter-subject variability may be measured by various methods, as will be understood by those skilled in the art. The inter-subject variability is preferably calculated as follows. The area under a dose response curve (AUC) (i.e., the area between the dose-response curve and a baseline value) is determined for each subject. The average AUC for all subjects is determined by summing the AUCs of each subject and dividing the sum by the number of subjects. The absolute value of the difference between the subject's AUC and the average AUC is then determined for each subject. The absolute values of the differences obtained are then summed to give a value that represents the inter-subject variability. Lower values represent lower inter-subject variabilities and higher values represent higher inter-subject variabilities.

Mixtures of calcitonin drug-oligomer conjugates having a dispersity coefficient greater than 10,000 according to embodiments of the present invention preferably have two or more of the above-described improved properties. More preferably, mixtures of calcitonin drug-oligomer conjugates having a dispersity coefficient greater than 10,000 according to embodiments of the present invention have three or more of the above-described improved properties. Most preferably, mixtures of calcitonin drug-oligomer conjugates having a dispersity coefficient greater than 10,000 according to embodiments of the present invention have four or more of the above-described improved properties.

According to other embodiments of the present invention, a mixture of conjugates in which each conjugate includes a calcitonin drug coupled to an oligomer and has the same number of polyethylene glycol subunits is provided.

The calcitonin drug is preferably calcitonin. More preferably, the calcitonin drug is salmon calcitonin. However, it is to be understood that the calcitonin drug may be selected from various calcitonin drugs known to those skilled in the art including, for example, calcitonin precursor peptides, calcitonin, calcitonin analogs, calcitonin fragments, and calcitonin fragment analogs. Calcitonin precursor peptides include, but are not limited to, katacalcin (PDN-21) (C-pro-calcitonin), and N-proCT (amino-terminal procalcitonin cleavage peptide), human. Calcitonin analogs may be provided by substitution of one or more amino acids in calcitonin as described above. Calcitonin fragments include, but are not limited to, calcitonin 1–7, human; and calcitonin 8–32, salmon. Calcitonin fragment analogs may be provided by substitution of one or more of the amino acids in a calcitonin fragment as described above.

The oligomer may be various oligomers comprising a polyethylene glycol moiety as will be understood by those skilled in the art. Preferably, the polyethylene glycol moiety of the oligomer has at least 2, 3 or 4 polyethylene glycol subunits. More preferably, the polyethylene glycol moiety has at least 5 or 6 polyethylene glycol subunits and, most preferably, the polyethylene glycol moiety has at least 7 polyethylene glycol subunits.

The oligomer may comprise one or more other moieties as will be understood by those skilled in the art including, but not limited to, additional hydrophilic moieties, lipophilic moieties, spacer moieties, linker moieties, and terminating moieties. The various moieties in the oligomer are covalently coupled to one another by either hydrolyzable or non-hydrolyzable bonds.

The oligomer may further comprise one or more additional hydrophilic moieties (i.e., moieties in addition to the polyethylene glycol moiety) including, but not limited to, sugars, polyalkylene oxides, and polyamine/PEG copolymers. As polyethylene glycol is a polyalkylene oxide, the additional hydrophilic moiety may be a polyethylene glycol moiety. Adjacent polyethylene glycol moieties will be considered to be the same moiety if they are coupled by an ether bond. For example, the moiety

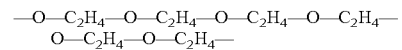

is a single polyethylene glycol moiety having six polyethylene glycol subunits. If this moiety were the only hydrophilic moiety in the oligomer, the oligomer would not contain an additional hydrophilic moiety. Adjacent polyethylene glycol moieties will be considered to be different moieties if they are coupled by a bond other than an ether bond. For example, the moiety

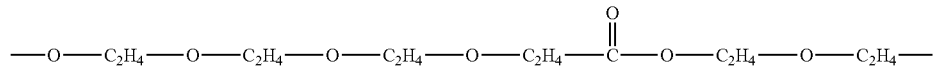

is a polyethylene glycol moiety having four polyethylene glycol subunits and an additional hydrophilic moiety having two polyethylene glycol subunits. Preferably, oligomers according to embodiments of the present invention comprise a polyethylene glycol moiety and no additional hydrophilic moieties.

The oligomer may further comprise one or more lipophilic moieties as will be understood by those skilled in the art. The lipophilic moiety is preferably a saturated or unsaturated, linear or branched alkyl moiety or a saturated or unsaturated, linear or branched fatty acid moiety. When the lipophilic moiety is an alkyl moiety, it is preferably a linear, saturated or unsaturated alkyl moiety having 1 to 28 carbon atoms. More preferably, the alkyl moiety has 2 to 12 carbon atoms. When the lipophilic moiety is a fatty acid moiety, it is preferably a natural fatty acid moiety that is linear, saturated or unsaturated, having 2 to 18 carbon atoms. More preferably, the fatty acid moiety has 3 to 14 carbon atoms. Most preferably, the fatty acid moiety has at least 4, 5 or 6 carbon atoms.

The oligomer may further comprise one or more spacer moieties as will be understood by those skilled in the art. Spacer moieties may, for example, be used to separate a hydrophilic moiety from a lipophilic moiety, to separate a lipophilic moiety or hydrophilic moiety from the calcitonin drug, to separate a first hydrophilic or lipophilic moiety from a second hydrophilic or lipophilic moiety, or to separate a hydrophilic moiety or lipophilic moiety from a linker moiety. Spacer moieties are preferably selected from the group consisting of sugar, cholesterol and glycerine moieties.

The oligomer may further comprise one or more linker moieties that are used to couple the oligomer with the calcitonin drug as will be understood by those skilled in the art. Linker moieties are preferably selected from the group consisting of alkyl and fatty acid moieties.

The oligomer may further comprise one or more terminating moieties at the one or more ends of the oligomer which are not coupled to the calcitonin drug. The terminating moiety is preferably an alkyl or alkoxy moiety, and is more preferably a lower alkyl or lower alkoxy moiety. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugars, cholesterol, alcohols, and fatty acids.

The oligomer is preferably covalently coupled to the calcitonin drug. In some embodiments, the calcitonin drug is coupled to the oligomer utilizing a hydrolyzable bond (e.g., an ester or carbonate bond). A hydrolyzable coupling may provide a calcitonin drug-oligomer conjugate that acts as a prodrug. In certain instances, for example where the calcitonin drug-oligomer conjugate is inactive (i.e., the conjugate lacks the ability to affect the body through the calcitonin drug's primary mechanism of action), a hydrolyzable coupling may provide for a time-release or controlled-release effect, administering the calcitonin drug over a given time period as one or more oligomers are cleaved from their respective calcitonin drug-oligomer conjugates to provide the active drug. In other embodiments, the calcitonin drug is coupled to the oligomer utilizing a non-hydrolyzable bond (e.g., a carbamate, amide, or ether bond). Use of a non-hydrolyzable bond may be preferable when it is desirable to allow the calcitonin drug-oligomer conjugate to circulate in the bloodstream for an extended period of time, preferably at least 2 hours. When the oligomer is covalently coupled to the calcitonin drug, the oligomer further comprises one or more bonding moieties that are used to covalently couple the oligomer with the calcitonin drug as will be understood by those skilled in the art. Bonding moieties are preferably selected from the group consisting of covalent bond(s), ester moieties, carbonate moieties, carbamate moieties, amide moieties and secondary amine moieties. More than one moiety on the oligomer may be covalently coupled to the calcitonin drug.

While the oligomer is preferably covalently coupled to the calcitonin drug, it is to be understood that the oligomer may be non-covalently coupled to the calcitonin drug to form a non-covalently conjugated calcitonin drug-oligomer complex. As will be understood by those skilled in the art, non-covalent couplings include, but are not limited to, hydrogen bonding, ionic bonding, Van der Waals bonding, and micellular or liposomal encapsulation. According to embodiments of the present invention, oligomers may be suitably constructed, modified and/or appropriately functionalized to impart the ability for non-covalent conjugation in a selected manner (e.g., to impart hydrogen bonding capability), as will be understood by those skilled in the art. According to other embodiments of present invention, oligomers may be derivatized with various compounds including, but not limited to, amino acids, oligopeptides, peptides, bile acids, bile acid derivatives, fatty acids, fatty acid derivatives, salicylic acids, salicylic acid derivatives, aminosalicylic acids, and aminosalicylic acid derivatives. The resulting oligomers can non-covalently couple (complex) with drug molecules, pharmaceutical products, and/or pharmaceutical excipients. The resulting complexes preferably have balanced lipophilic and hydrophilic properties. According to still other embodiments of the present invention, oligomers may be derivatized with amine and/or alkyl amines. Under suitable acidic conditions, the resulting oligomers can form non-covalently conjugated complexes with drug molecules, pharmaceutical products and/or pharmaceutical excipients. The products resulting from such complexation preferably have balanced lipophilic and hydrophilic properties.

More than one oligomer (i.e., a plurality of oligomers) may be coupled to the calcitonin drug. The oligomers in the plurality are preferably the same. However, it is to be understood that the oligomers in the plurality may be different from one another, or, alternatively, some of the oligomers in the plurality may be the same and some may be different. When a plurality of oligomers are coupled to the calcitonin drug, it may be preferable to couple one or more of the oligomers to the calcitonin drug with hydrolyzable bonds and couple one or more of the oligomers to the calcitonin drug with non-hydrolyzable bonds. Alternatively, all of the bonds coupling the plurality of oligomers to the calcitonin drug may be hydrolyzable, but have varying degrees of hydrolyzability such that, for example, one or more of the oligomers is rapidly removed from the calcitonin drug by hydrolysis in the body and one or more of the oligomers is slowly removed from the calcitonin drug by hydrolysis in the body.

The oligomer may be coupled to the calcitonin drug at various nucleophilic residues of the calcitonin drug including, but not limited to, nucleophilic hydroxyl functions and/or amino functions. When the calcitonin drug is a polypeptide, a nucleophilic hydroxyl function may be found, for example, at serine and/or tyrosine residues, and a nucleophilic amino function may be found, for example, at histidine and/or lysine residues, and/or at the one or more N-termini of the polypeptide. When an oligomer is coupled to the one or more N-terminus of the calcitonin polypeptide, the coupling preferably forms a secondary amine. When the calcitonin drug is salmon calcitonin, for example, the oligomer may be coupled to an amino functionality of the salmon calcitonin, including the amino functionality of $Lys^{11}$, $Lys^{18}$ and/or the N-terminus. While one or more oligomers may be coupled to the salmon calcitonin, a higher bioefficacy, such as improved serum calcium lowering ability, is observed for the di-conjugated salmon calcitonin where an oligomer is coupled to the amino functionalities of $Lys^{11}$ and the $Lys^{18}$.

Mixtures of calcitonin drug-oligomer conjugates where each conjugate in the mixture has the same number of polyethylene glycol subunits may be synthesized by various methods. For example, a mixture of oligomers consisting of carboxylic acid and polyethylene glycol where each oligomer in the mixture has the same number of polyethylene glycol subunits is synthesized by contacting a mixture of carboxylic acid with a mixture of polyethylene glycol where each polyethylene glycol molecule in the mixture has the same number of polyethylene glycol subunits under conditions sufficient to provide a mixture of oligomers where each oligomer in the mixture has the same number of polyethylene glycol subunits. The oligomers of the mixture where each oligomer in the mixture has the same number of polyethylene glycol subunits are then activated so that they are capable of reacting with a calcitonin drug to provide a calcitonin drug-oligomer conjugate. One embodiment of a synthesis route for providing a mixture of activated oligomers where each oligomer in the mixture has the same number of polyethylene glycol subunits is illustrated in FIG. 3 and described in Examples 11–18 hereinbelow. Another embodiment of a synthesis route for providing a mixture of activated oligomers where each oligomer in the mixture has the same number of polyethylene glycol subunits is illustrated in FIG. 4 and described in Examples 19–24 hereinbelow. Still another embodiment of a synthesis route for providing a mixture of activated oligomers where each oligomer in the mixture has the same number of polyethylene glycol subunits is illustrated in FIG. 5 and described in Examples 25–29 hereinbelow. Yet another embodiment of a synthesis route for providing a mixture of activated oligomers where each oligomer in the mixture has the same number of polyethylene glycol subunits is illustrated in FIG. 6 and described in Examples 30–31 hereinbelow. Another embodiment of a synthesis route for providing a mixture of activated oligomers where each oligomer in the mixture has the same number of polyethylene glycol subunits is illustrated in FIG. 7 and described in Examples 32–37 hereinbelow. Still another embodiment of a synthesis route for providing a mixture of activated oligomers where each oligomer in the mixture has the same number of polyethylene glycol subunits is illustrated in FIG. 8 and described in Example 38 hereinbelow. Yet another embodiment of a synthesis route for providing a mixture of activated oligomers where each oligomer in the mixture has the same number of polyethylene glycol subunits is illustrated in FIG. 9 and described in Example 39 hereinbelow. Another embodiment of a synthesis route for providing a mixture of activated oligomers having a mixture of activated oligomers where each oligomer in the mixture has the same number of polyethylene glycol subunits is illustrated in FIG. 10 and described in Example 40 hereinbelow.

The mixture of activated oligomers where each oligomer in the mixture has the same number of polyethylene glycol subunits is reacted with a mixture of calcitonin drugs under conditions sufficient to provide a mixture of calcitonin drug-oligomer conjugates. A preferred synthesis is described in Example 41 hereinbelow. As will be understood by those skilled in the art, the reaction conditions (e.g., selected molar ratios, solvent mixtures and/or pH) may be controlled such that the mixture of calcitonin drug-oligomer conjugates resulting from the reaction of the mixture of activated oligomers where each oligomer in the mixture has the same number of polyethylene glycol subunits and the mixture of calcitonin drugs is a mixture of conjugates where each conjugate in the mixture has the same number of polyethylene glycol subunits. For example, conjugation at the amino functionality of lysine may be suppressed by maintaining the pH of the reaction solution below the $pK_a$ of lysine. Alternatively, the mixture of calcitonin drug-oligomer conjugates may be separated and isolated utilizing, for example, HPLC to provide a mixture of calcitonin drug-oligomer conjugates, for example mono-, di-, or tri-conjugates, where each conjugate in the mixture has the same number of polyethylene glycol subunits. The degree of conjugation (e.g., whether the isolated molecule is a mono-, di-, or tri-conjugate) of a particular isolated conjugate may be determined and/or verified utilizing various techniques as will be understood by those skilled in the art including, but not limited to, mass spectroscopy. The particular conjugate structure (e.g., whether the oligomer is at $Lys^{11}$, $Lys^{18}$ or the N-terminus of a salmon calcitonin monoconjugate) may be determined and/or verified utilizing various techniques as will be understood by those skilled in the art including, but not limited to, sequence analysis, peptide mapping, selective enzymatic cleavage, and/or endopeptidase cleavage.

As will be understood by those skilled in the art, one or more of the reaction sites on the calcitonin drug may be blocked by, for example, reacting the calcitonin drug with a suitable blocking reagent such as N-tert-butoxycarbonyl (t-BOC), or N-(9-fluorenylmethoxycarbonyl) (N-FMOC). This process may be preferred, for example, when the calcitonin drug is a polypeptide and it is desired to form an unsaturated conjugate (i.e., a conjugate wherein not all nucleophilic residues are conjugated) having an oligomer at the N-terminus of the polypeptide. Following such blocking, the mixture of blocked calcitonin drugs may be reacted with the mixture of activated oligomers where each oligomer in the mixture has the same number of polyethylene glycol subunits to provide a mixture of calcitonin drug-oligomer conjugates having oligomer(s) coupled to one or more nucleophilic residues and having blocking moieties coupled to other nucleophilic residues. After the conjugation reaction, the calcitonin drug-oligomer conjugates may be de-blocked as will be understood by those skilled in the art. If necessary, the mixture of calcitonin drug-oligomer conjugates may then be separated as described above to provide a mixture of calcitonin drug-oligomer conjugates where each conjugate in the mixture has the same number of polyethylene glycol subunits. Alternatively, the mixture of calcitonin drug-oligomer conjugates may be separated prior to de-blocking.

Mixtures of calcitonin drug-oligomer conjugates where each conjugate in the mixture has the same number of polyethylene glycol subunits according to embodiments of the present invention preferably have improved properties when compared with those of conventional mixtures. For example, a mixture of calcitonin drug-oligomer conjugates where each conjugate in the mixture has the same number of polyethylene glycol subunits preferably is capable of lowering serum calcium levels by at least 5 percent. Preferably, the mixture of conjugates is capable of lowering serum calcium levels by at least 10, 11, 12, 13 or 14 percent. More preferably, the mixture of conjugates is capable of lowering serum calcium levels by at least 15, 16, 17, 18 or 19 percent, and, most preferably, the mixture of conjugates is capable of lowering serum calcium levels by at least 20 percent.

As anther example, a mixture of calcitonin drug-oligomer conjugates where each conjugate in the mixture has the same number of polyethylene glycol subunits preferably has an increased resistance to degradation by chymotrypsin and/or trypsin when compared to the resistance to degradation by chymotrypsin and/or trypsin, respectively, of the calcitonin drug which is not coupled to the oligomer. Resistance to chymotrypsin or trypsin corresponds to the percent remaining when the molecule to be tested is digested in the applicable enzyme using a procedure similar to the one outlined in Example 51 below. Preferably, the resistance to degradation by chymotrypsin of the mixture of calcitonin drug-oligomer conjugates is about 10 percent greater than the resistance to degradation by chymotrypsin of the mixture of calcitonin drugs that is not conjugated with the oligomer. More preferably, the resistance to degradation by chymotrypsin of the mixture of calcitonin drug-oligomer conjugates is about 15 percent greater than the resistance to degradation by chymotrypsin of the mixture of calcitonin drug that is not conjugated with the oligomer, and, most preferably, the resistance to degradation by chymotrypsin of the mixture of calcitonin drug-oligomer conjugates is about 20 percent greater than the resistance to degradation by chymotrypsin of the mixture of calcitonin drug that is not conjugated with the oligomer. Preferably, the resistance to degradation by trypsin of the mixture of calcitonin drug-oligomer conjugates is about 10 percent greater than the resistance to degradation by trypsin of the mixture of calcitonin drug that is not conjugated with the oligomer. More preferably, the resistance to degradation by trypsin of the mixture of calcitonin drug-oligomer conjugates is about 20 percent greater than the resistance to degradation by trypsin of the mixture of calcitonin drug that is not conjugated with the oligomer, and, most preferably, the resistance to degradation by trypsin of the mixture of calcitonin drug-oligomer conjugates is about 30 percent greater than the resistance to degradation by trypsin of the mixture of calcitonin drug that is not conjugated with the oligomer.

As still another example, a mixture of calcitonin drug-oligomer conjugates where each conjugate in the mixture has the same number of polyethylene glycol subunits preferably has a higher bioefficacy than the bioefficacy of the calcitonin drug which is not coupled to the oligomer. The bioefficacy of a particular compound corresponds to its area-under-the-curve (AUC) value. Preferably, the bioefficacy of the mixture is about 5 percent greater than the bioefficacy of the calcitonin drug which is not coupled to the oligomer. More preferably, the bioefficacy of the mixture is about 10 percent greater than the bioefficacy of the calcitonin drug which is not coupled to the oligomer.

As yet another example, a mixture of calcitonin drug-oligomer conjugates where each conjugate in the mixture has the same number of polyethylene glycol subunits preferably has an in vivo activity that is greater than the in vivo activity of a polydispersed mixture of calcitonin drug-oligomer conjugates having the same number average molecular weight as the mixture of calcitonin drug-oligomer conjugates where each conjugate in the mixture has the same number of polyethylene glycol subunits. As will be understood by those skilled in the art, the number average molecular weight of a mixture may be measured by various methods including, but not limited to, size exclusion chromatography such as gel permeation chromatography as described, for example, in H. R. Allcock & F. W. Lampe, CONTEMPORARY POLYMER CHEMISTRY 394–402 (2d. ed., 1991).

As another example, a mixture of calcitonin drug-oligomer conjugates where each conjugate in the mixture has the same number of polyethylene glycol subunits preferably has an in vitro activity that is greater than the in vitro activity of a polydispersed mixture of calcitonin drug-oligomer conjugates having the same number average molecular weight as the mixture of calcitonin drug-oligomer conjugates where each conjugate in the mixture has the same number of polyethylene glycol subunits. As will be understood by those skilled in the art, the number average molecular weight of a mixture may be measured by various methods including, but not limited to, size exclusion chromatography.

As still another example, a mixture of calcitonin drug-oligomer conjugates where each conjugate in the mixture has the same number of polyethylene glycol subunits preferably has an increased resistance to degradation by chymotrypsin and/or trypsin when compared to the resistance to degradation by chymotrypsin and/or trypsin of a polydispersed mixture of calcitonin drug-oligomer conjugates having the same number average molecular weight as the mixture of calcitonin drug-oligomer conjugates where each conjugate in the mixture has the same number of polyethylene glycol subunits. As will be understood by those skilled in the art, the number average molecular weight of a mixture may be measured by various methods including, but not limited to, size exclusion chromatography.

As yet another example, a mixture of calcitonin drug-oligomer conjugates where each conjugate in the mixture has the same number of polyethylene glycol subunits preferably has an inter-subject variability that is less than the inter-subject variability of a polydispersed mixture of calcitonin drug-oligomer conjugates having the same number average molecular weight as the mixture of calcitonin drug-oligomer conjugates where each conjugate in the mixture has the same number of polyethylene glycol subunits. As will be understood by those skilled in the art, the number average molecular weight of a mixture may be measured by various methods including, but not limited to, size exclusion chromatography. The inter-subject variability may be measured by various methods, as will be understood by those skilled in the art. The inter-subject variability is preferably calculated as follows. The area under a dose response curve (AUC) (i.e., the area between the dose-response curve and a baseline value) is determined for each subject. The average AUC for all subjects is determined by summing the AUCs of each subject and dividing the sum by the number of subjects. The absolute value of the difference between the subject's AUC and the average AUC is then determined for each subject. The absolute values of the differences obtained are then summed to give a value that represents the inter-subject variability. Lower values represent lower inter-subject variabilities and higher values represent higher inter-subject variabilities.

Mixtures of calcitonin drug-oligomer conjugates where each conjugate in the mixture has the same number of polyethylene glycol subunits according to embodiments of the present invention preferably have two or more of the above-described improved properties. More preferably, mixtures of calcitonin drug-oligomer conjugates where each conjugate in the mixture has the same number of polyethylene glycol subunits according to embodiments of the present invention have three or more of the above-described improved properties. Most preferably, mixtures of calcitonin drug-oligomer conjugates where each conjugate in the mixture has the same number of polyethylene glycol subunits according to embodiments of the present invention have four or more of the above-described improved properties.

According to still other embodiments of the present invention, a mixture of conjugates is provided in which each conjugate has the same molecular weight and has the structure of Formula A:

$$\text{Calcitonin Drug} - [B - L_j - G_k - R - G'_m - R' - G''_n - T]_p \quad \text{(A)}$$

wherein:
B is a bonding moiety;
L is a linker moiety;
G, G' and G'' are individually selected spacer moieties;
R is a lipophilic moiety and R' is a polyalkylene glycol moiety, or R' is the lipophilic moiety and R is the polyalkylene glycol moiety;
T is a terminating moiety;
j, k, m and n are individually 0 or 1; and
p is an integer from 1 to the number of nucleophilic residues on the calcitonin drug.

The calcitonin drug is preferably calcitonin. More preferably, the calcitonin drug is salmon calcitonin. However, it is to be understood that the calcitonin drug may be selected from various calcitonin drugs known to those skilled in the art including, for example, calcitonin precursor peptides, calcitonin, calcitonin analogs, calcitonin fragments, and calcitonin fragment analogs. Calcitonin precursor peptides include, but are not limited to, katacalcin (PDN-21) (C-procalcitonin), and N-proCT (amino-terminal procalcitonin cleavage peptide), human. Calcitonin analogs may be provided by substitution of one or more amino acids in calcitonin as described above. Calcitonin fragments include, but are not limited to, calcitonin 1–7, human; and calcitonin 8–32, salmon. Calcitonin fragment analogs may be provided by substitution of one or more of the amino acids in a calcitonin fragment as described above.

According to these embodiments of the present invention, the polyalkylene glycol moiety of the oligomer preferably has at least 2, 3 or 4 polyalkylene glycol subunits. More preferably, the polyalkylene glycol moiety has at least 5 or 6 polyalkylene glycol subunits and, most preferably, the polyethylene glycol moiety has at least 7 polyalkylene glycol subunits. The polyalkylene glycol moiety is preferably a lower polyalkylene glycol moiety such as a polyethylene glycol moiety, a polypropylene glycol moiety, or a polybutylene glycol moiety. More preferably, the polyalkylene glycol moiety is a polyethylene glycol moiety or a polypropylene glycol moiety. Most preferably, the polyalkylene glycol moiety is a polyethylene glycol moiety. When the polyalkylene glycol moiety is a polypropylene glycol moiety, the moiety preferably has a uniform (i.e., not random) structure. An exemplary polypropylene glycol moiety having a uniform structure is as follows:

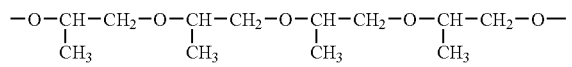

This uniform polypropylene glycol structure may be described as having only one methyl substituted carbon atom adjacent each oxygen atom in the polypropylene glycol chain. Such uniform polypropylene glycol moieties may exhibit both lipophilic and hydrophilic characteristics and thus be useful in providing amphiphilic calcitonin drug-oligomer conjugates without the use of lipophilic polymer moieties. Furthermore, coupling the secondary alcohol moiety of the polypropylene glycol moiety with a calcitonin drug may provide the calcitonin drug (e.g., salmon calcitonin) with improved resistance to degradation caused by enzymes such as trypsin and chymotrypsin found, for example, in the gut.

Figure 11:
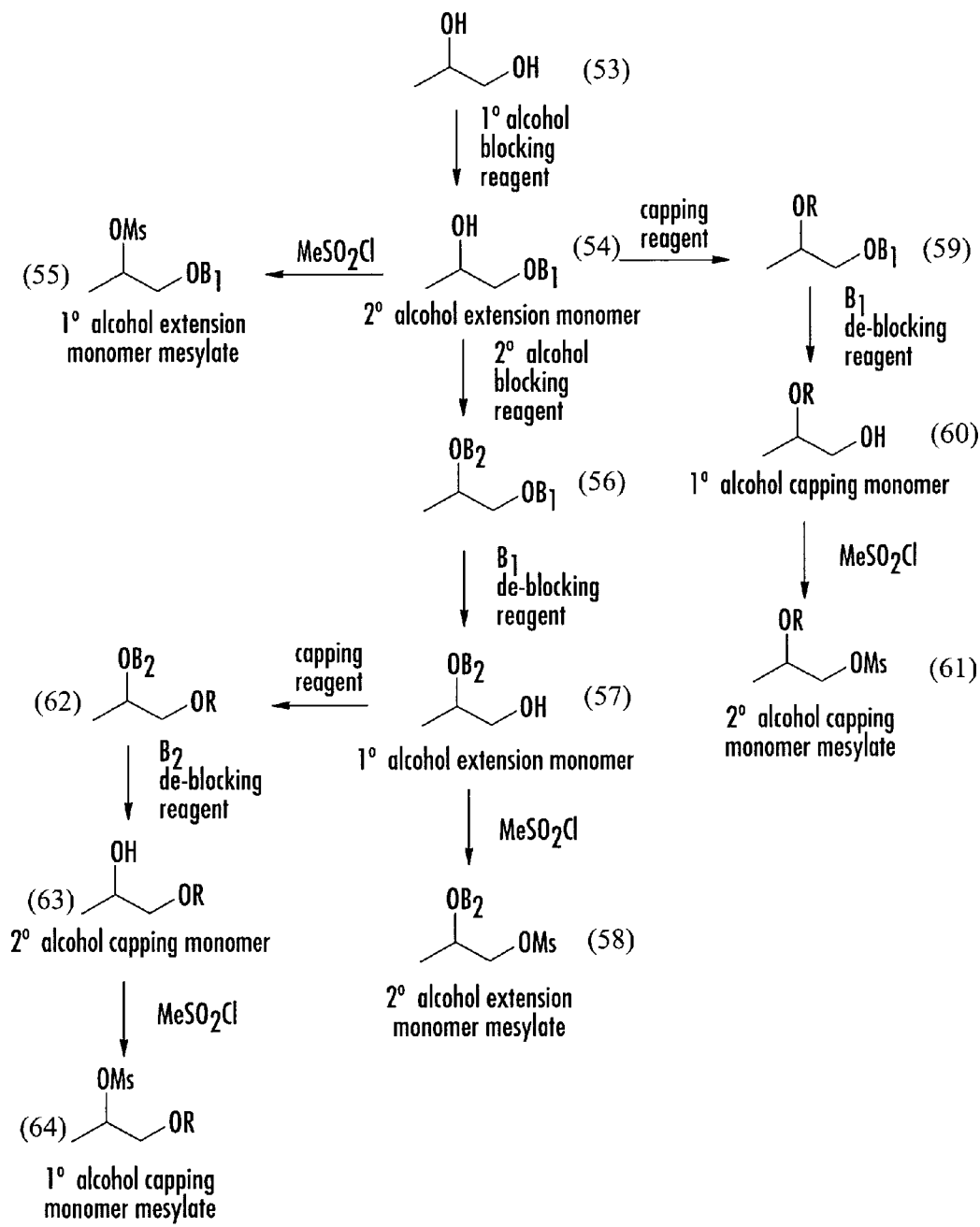
FIG. 11 illustrates a scheme for synthesizing various propylene glycol monomers according to embodiments of the present invention.
Figure 12:
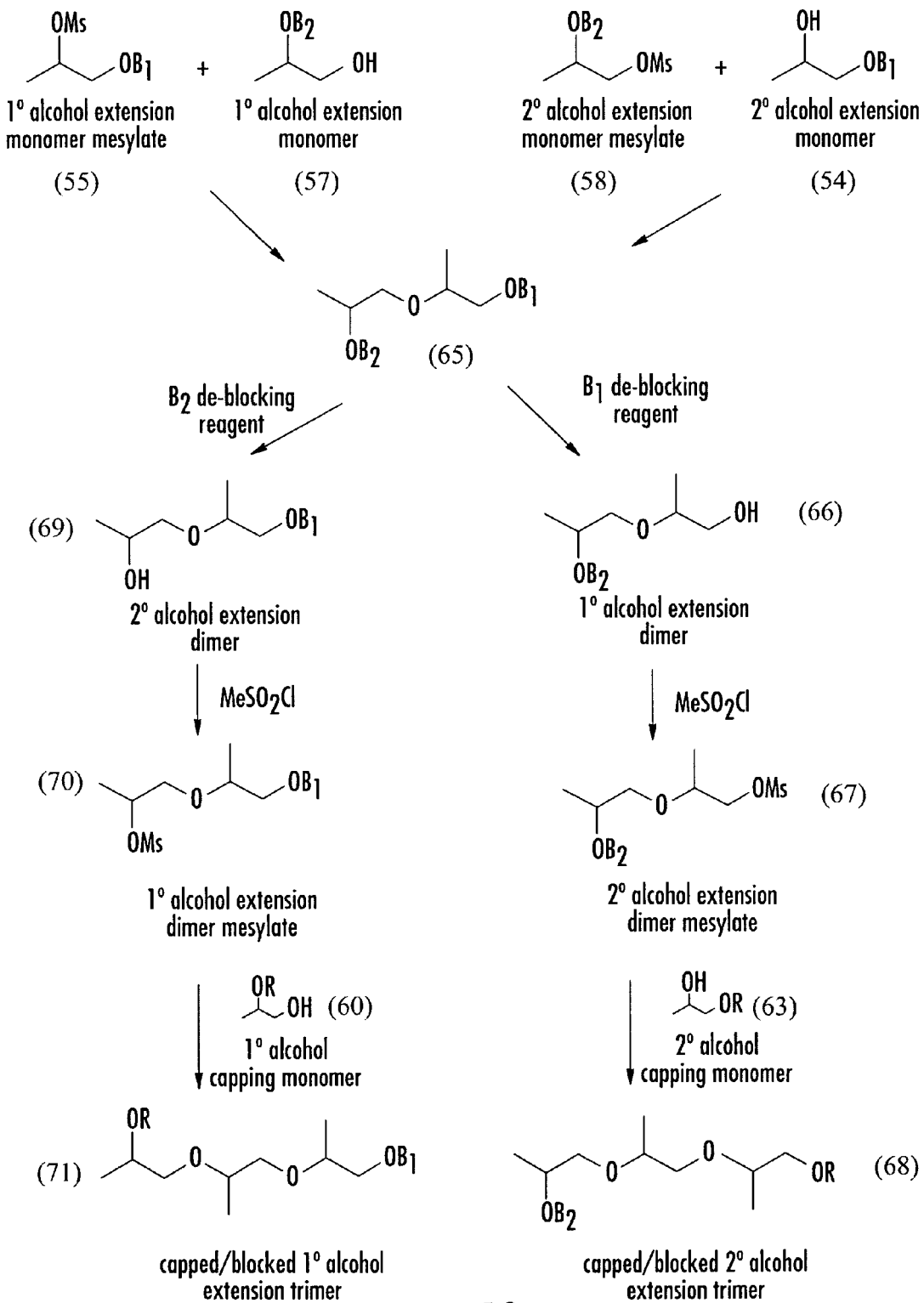
FIG. 12 illustrates a scheme for synthesizing various propylene glycol polymers according to embodiments of the present invention.
Figure 13:
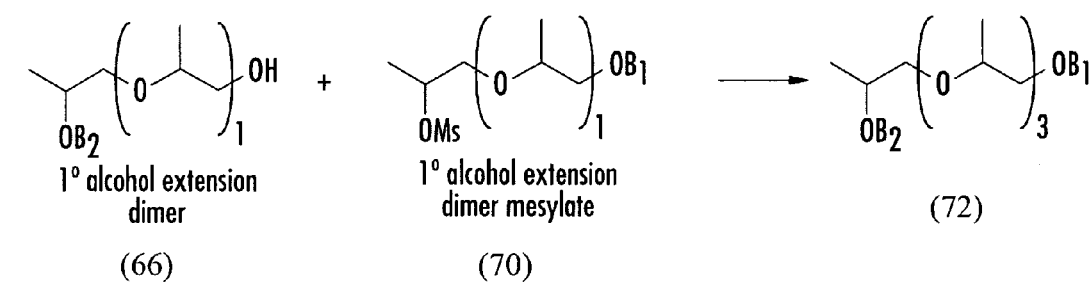
FIG. 13 illustrates a scheme for synthesizing various propylene glycol polymers according to embodiments of the present invention.
Figure 13:
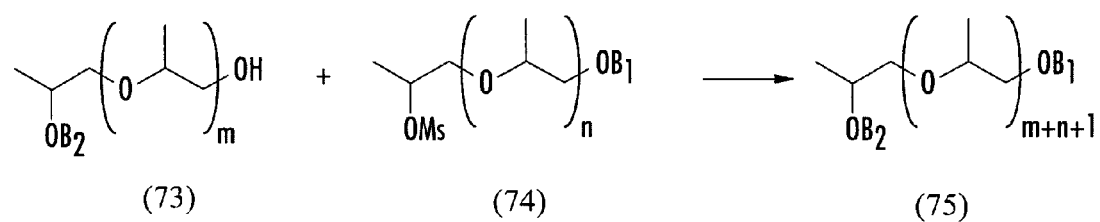

Uniform polypropylene glycol according to embodiments of the present invention is preferably synthesized as illustrated in FIGS. 11 through 13, which will now be described. As illustrated in FIG. 11, 1,2-propanediol 53 is reacted with a primary alcohol blocking reagent to provide a secondary alcohol extension monomer 54. The primary alcohol blocking reagent may be various primary alcohol blocking reagents as will be understood by those skilled in the art including, but not limited to, silylchloride compounds such as t-butyldiphenylsilylchloride and t-butyldimethylsilylchloride, and esterification reagents such as $Ac_2O$. Preferably, the primary alcohol blocking reagent is a primary alcohol blocking reagent that is substantially non-reactive with secondary alcohols, such as t-butyldiphenylsilylchloride or t-butyldimethylsilylchloride. The secondary alcohol extension monomer (54) may be reacted with methanesulfonyl chloride ($MeSO_2Cl$) to provide a primary extension alcohol monomer mesylate 55.

Alternatively, the secondary alcohol extension monomer 54 may be reacted with a secondary alcohol blocking reagent to provide compound 56. The secondary alcohol blocking reagent may be various secondary alcohol blocking reagents as will be understood by those skilled in the art including, but not limited to, benzyl chloride. The compound 56 may be reacted with a $B_1$ de-blocking reagent to remove the blocking moiety $B_1$ and provide a primary alcohol extension monomer 57. The $B_1$ de-blocking reagent may be selected from various de-blocking reagents as will be understood by one skilled in the art. When the primary alcohol has been blocked by forming an ester, the $B_1$ de-blocking reagent is a de-esterification reagent, such as a base (e.g., potassium carbonate). When the primary alcohol has been blocked using a silylchloride, the $B_1$ de-blocking reagent is preferably tetrabutylammonium fluoride (TBAF). The primary alcohol extension monomer 57 may be reacted with methane sulfonyl chloride to provide a secondary alcohol extension monomer mesylate 58.

The primary alcohol extension monomer 54 and the secondary alcohol extension monomer 57 may be capped as follows. The secondary alcohol extension monomer 54 may be reacted with a capping reagent to provide a compound 59. The capping reagent may be various capping reagents as will be understood by those skilled in the art including, but not limited to, alkyl halides such as methyl chloride. The compound 59 may be reacted with a $B_1$ de-blocking agent as described above to provide a primary alcohol capping monomer 60. The primary alcohol capping monomer 60 may be reacted with methane sulfonyl chloride to provide the secondary alcohol capping monomer mesylate 61. The primary alcohol extension monomer 57 may be reacted with a capping reagent to provide a compound 62. The capping reagent may be various capping reagents as described above. The compound 62 may be reacted with a $B_2$ de-blocking reagent to remove the blocking moiety $B_2$ and provide a secondary alcohol capping monomer 63. The $B_2$ de-blocking reagent may be various de-blocking agents as will be understood by those skilled in the art including, but not limited to, $H_2$ in the presence of a palladium/activated carbon catalyst. The secondary alcohol capping monomer may be reacted with methanesulfonyl chloride to provide a primary alcohol capping monomer mesylate 64. While the embodiments illustrated in FIG. 11 show the synthesis of capping monomers, it is to be understood that similar reactions may be performed to provide capping polymers.

In general, chain extensions may be effected by reacting a primary alcohol extension mono- or poly-mer such as the primary alcohol extension monomer 57 with a primary alcohol extension mono- or poly-mer mesylate such as the primary alcohol extension monomer mesylate 55 to provide various uniform polypropylene chains or by reacting a secondary alcohol extension mono- or poly-mer such as the secondary alcohol extension monomer 54 with a secondary alcohol extension mono-or poly-mer mesylate such as the secondary alcohol extension monomer mesylate 58.

For example, in FIG. 13, the primary alcohol extension monomer mesylate 55 is reacted with the primary alcohol extension monomer 57 to provide a dimer compound 65. Alternatively, the secondary alcohol extension monomer mesylate 58 may be reacted with the secondary alcohol extension monomer 54 to provide the dimer compound 65. The $B_1$ blocking moiety on the dimer compound 65 may be removed using a $B_1$ de-blocking reagent as described above to provide a primary alcohol extension dimer 66. The primary alcohol extension dimer 66 may be reacted with methane sulfonyl chloride to provide a secondary alcohol extension dimer mesylate 67. Alternatively, the $B_2$ blocking moiety on the dimer compound 65 may be removed using the $B_2$ de-blocking reagent as described above to provide a secondary alcohol extension dimer 69. The secondary alcohol extension dimer 69 may be reacted with methane sulfonyl chloride to provide a primary alcohol extension dimer mesylate 70.

As will be understood by those skilled in the art, the chain extension process may be repeated to achieve various other chain lengths. For example, as illustrated in FIG. 13, the primary alcohol extension dimer 66 may be reacted with the primary alcohol extension dimer mesylate 70 to provide a tetramer compound 72. As further illustrated in FIG. 13, a generic chain extension reaction scheme involves reacting the primary alcohol extension mono- or poly-mer 73 with the primary alcohol extension mono- or poly-mer mesylate 74 to provide the uniform polypropylene polymer 75. The values of m and n may each range from 0 to 1000 or more. Preferably, m and n are each from 0 to 50. While the embodiments illustrated in FIG. 13 show primary alcohol extension mono- and/or poly-mers being reacted with primary alcohol extension mono- and/or poly-mer mesylates, it is to be understood that similar reactions may be carried out using secondary alcohol extension mono- and/or poly-mers and secondary alcohol extension mono- and/or poly-mer mesylates.

An end of a primary alcohol extension mono- or poly-mer or an end of a primary alcohol extension mono- or poly-mer mesylate may be reacted with a primary alcohol capping mono- or poly-mer mesylate or a primary alcohol capping mono- or poly-mer, respectively, to provide a capped uniform polypropylene chain. For example, as illustrated in FIG. 12, the primary alcohol extension dimer mesylate 70 is reacted with the primary alcohol capping monomer 60 to provide the capped/blocked primary alcohol extension trimer 71. As will be understood by those skilled in the art, the $B_1$ blocking moiety may be removed and the resulting capped primary alcohol extension trimer may be reacted with a primary alcohol extension mono- or poly-mer mesylate to extend the chain of the capped trimer 71.

An end of a secondary alcohol extension mono-or poly-mer or an end of a secondary alcohol extension mono-or poly-mer mesylate may be reacted with a secondary alcohol capping mono-or poly-mer mesylate or a secondary alcohol capping mono- or poly-mer, respectively, to provide a capped uniform polypropylene chain. For example, as illustrated in FIG. 12, the secondary alcohol extension dimer mesylate 67 is reacted with the secondary alcohol capping monomer 63 to provide the capped/blocked primary alcohol extension trimer 68. The $B_2$ blocking moiety may be removed as described above and the resulting capped secondary alcohol extension trimer may be reacted with a secondary alcohol extension mer mesylate to extend the chain of the capped trimer 68. While the syntheses illustrated in FIG. 12 show the reaction of a dimer with a capping monomer to provide a trimer, it is to be understood that the capping process may be performed at any point in the synthesis of a uniform polypropylene glycol moiety, or, alternatively, uniform polypropylene glycol moieties may be provided that are not capped. While the embodiments illustrated in FIG. 12 show the capping of a polybutylene oligomer by synthesis with a capping monomer, it is to be understood that polybutylene oligomers of the present invention may be capped directly (i.e., without the addition of a capping monomer) using a capping reagent as described above in FIG. 11.

Uniform polypropylene glycol moieties according to embodiments of the present invention may be coupled to a calcitonin drug, a lipophilic moiety such as a carboxylic acid, and/or various other moieties by various methods as will be understood by those skilled in the art including, but not limited to, those described herein with respect to polyethylene glycol moieties.

According to these embodiments of the present invention, the lipophilic moiety is a lipophilic moiety as will be understood by those skilled in the art. The lipophilic moiety is preferably a saturated or unsaturated, linear or branched alkyl moiety or a saturated or unsaturated, linear or branched fatty acid moiety. When the lipophilic moiety is an alkyl moiety, it is preferably a linear, saturated or unsaturated alkyl moiety having 1 to 28 carbon atoms. More preferably, the alkyl moiety has 2 to 12 carbon atoms. When the lipophilic moiety is a fatty acid moiety, it is preferably a natural fatty acid moiety that is linear, saturated or unsaturated, having 2 to 18 carbon atoms. More preferably, the fatty acid moiety has 3 to 14 carbon atoms. Most preferably, the fatty acid moiety has at least 4, 5 or 6 carbon atoms.

According to these embodiments of the present invention, the spacer moieties, G, G' and G", are spacer moieties as will be understood by those skilled in the art. Spacer moieties are preferably selected from the group consisting of sugar, cholesterol and glycerine moieties. Preferably, oligomers of these embodiments do not include spacer moieties (i.e., k, m and n are preferably 0).

According to these embodiments of the present invention, the linker moiety, L, may be used to couple the oligomer with the drug as will be understood by those skilled in the art. Linker moieties are preferably selected from the group consisting of alkyl and fatty acid moieties.

According to these embodiments of the present invention, the terminating moiety is preferably an alkyl or alkoxy moiety, and is more preferably a lower alkyl or lower alkoxy moiety. Most preferably, the terminating moiety is methyl or methoxy. While the terminating moiety is preferably an alkyl or alkoxy moiety, it is to be understood that the terminating moiety may be various moieties as will be understood by those skilled in the art including, but not limited to, sugars, cholesterol, alcohols, and fatty acids.

According to these embodiments of the present invention, the oligomer, which is represented by the bracketed portion of the structure of Formula A, is covalently coupled to the calcitonin drug. In some embodiments, the calcitonin drug is coupled to the oligomer utilizing a hydrolyzable bond (e.g., an ester or carbonate bond). A hydrolyzable coupling may provide a calcitonin drug-oligomer conjugate that acts as a prodrug. In certain instances, for example where the calcitonin drug-oligomer conjugate is inactive (i.e., the conjugate lacks the ability to affect the body through the calcitonin drug's primary mechanism of action), a hydrolyzable coupling may provide for a time-release or controlled-release effect, administering the calcitonin drug over a given time period as one or more oligomers are cleaved from their respective calcitonin drug-oligomer conjugates to provide the active drug. In other embodiments, the calcitonin drug is coupled to the oligomer utilizing a non-hydrolyzable bond (e.g., a carbamate, amide, or ether bond). Use of a non-hydrolyzable bond may be preferable when it is desirable to allow the calcitonin drug-oligomer conjugate to circulate in the bloodstream for an extended period of time, preferably at least 2 hours. The bonding moiety, B, may be various bonding moieties that may be used to covalently couple the oligomer with the calcitonin drug as will be understood by those skilled in the art. Bonding moieties are preferably selected from the group consisting of covalent bond(s), ester moieties, carbonate moieties, carbamate moieties, amide moieties and secondary amine moieties.

The variable p is an integer from 1 to the number of nucleophilic residues on the calcitonin drug. When p is greater than 1, more than one oligomer (i.e., a plurality of oligomers) is coupled to the drug. According the these embodiments of the present invention, the oligomers in the plurality are the same. When a plurality of oligomers are coupled to the drug, it may be preferable to couple one or more of the oligomers to the drug with hydrolyzable bonds and couple one or more of the oligomers to the drug with non-hydrolyzable bonds. Alternatively, all of the bonds coupling the plurality of oligomers to the drug may be hydrolyzable, but have varying degrees of hydrolyzability such that, for example, one or more of the oligomers is rapidly removed from the drug by hydrolysis in the body and one or more of the oligomers is slowly removed from the drug by hydrolysis in the body. When the calcitonin drug is salmon calcitonin, p is preferably 1 or 2, and is more preferably 2.

The oligomer may be coupled to the calcitonin drug at various nucleophilic residues of the calcitonin drug including, but not limited to, nucleophilic hydroxyl functions and/or amino functions. When the calcitonin drug is a polypeptide, a nucleophilic hydroxyl function may be found, for example, at serine and/or tyrosine residues, and a nucleophilic amino function may be found, for example, at histidine and/or lysine residues, and/or at the one or more N-termini of the polypeptide. When an oligomer is coupled to the one or more N-terminus of the calcitonin polypeptide, the coupling preferably forms a secondary amine. When the calcitonin drug is salmon calcitonin, for example, the oligomer may be coupled to an amino functionality of the salmon calcitonin, including the amino functionality of $Lys^{11}$, $Lys^{18}$ and/or the N-terminus. While one or more oligomers may be coupled to the salmon calcitonin, a higher bioefficacy, such as improved serum calcium lowering ability, is observed for the di-conjugated salmon calcitonin where an oligomer is coupled to the amino functionalities of $Lys^{11}$ and the $Lys^{18}$.

Mixtures of calcitonin drug-oligomer conjugates where each conjugate in the mixture has the same molecular weight and has the structure of Formula A may be synthesized by various methods. For example, a mixture of oligomers consisting of carboxylic acid and polyethylene glycol is synthesized by contacting a mixture of carboxylic acid with a mixture of polyethylene glycol under conditions sufficient to provide a mixture of oligomers. The oligomers of the mixture are then activated so that they are capable of reacting with a calcitonin drug to provide a calcitonin drug-oligomer conjugate. One embodiment of a synthesis route for providing a mixture of activated oligomers where each oligomer has the same molecular weight and has a structure of the oligomer of Formula A is illustrated in FIG. 3 and described in Examples 11–18 hereinbelow. Another embodiment of a synthesis route for providing a mixture of activated oligomers where each oligomer has the same molecular weight and has a structure of the oligomer of Formula A is illustrated in FIG. 4 and described in Examples 19–24 hereinbelow. Still another embodiment of a synthesis route for providing a mixture of activated oligomers where each oligomer has the same molecular weight and has a structure of the oligomer of Formula A is illustrated in FIG. 5 and described in Examples 25–29 hereinbelow. Yet another embodiment of a synthesis route for providing a mixture of activated oligomers where each oligomer has the same molecular weight and has a structure of the oligomer of Formula A is illustrated in FIG. 6 and described in Examples 30–31 hereinbelow. Another embodiment of a synthesis route for providing a mixture of activated oligomers where each oligomer has the same molecular weight and has a structure of the oligomer of Formula A is illustrated in FIG. 7 and described in Examples 32–37 hereinbelow. Still another embodiment of a synthesis route for providing a mixture of activated oligomers where each oligomer has the same molecular weight and has a structure of the oligomer of Formula A is illustrated in FIG. 8 and described in Example 38 hereinbelow. Yet another embodiment of a synthesis route for providing a mixture of activated oligomers where each oligomer has the same molecular weight and has a structure of the oligomer of Formula A is illustrated in FIG. 9 and described in Example 39 hereinbelow. Another embodiment of a synthesis route for providing a mixture of activated oligomers where each oligomer has the same molecular weight and has a structure of the oligomer of Formula A is illustrated in FIG. 10 and described in Example 40 hereinbelow.

The mixture of activated oligomers where each oligomer has the same molecular weight and has a structure of the oligomer of Formula A is reacted with a mixture of calcitonin drugs where each drug in the mixture has the same molecular weight under conditions sufficient to provide a mixture of calcitonin drug-oligomer conjugates. A preferred synthesis is described in Example 41 hereinbelow. As will be understood by those skilled in the art, the reaction conditions (e.g., selected molar ratios, solvent mixtures and/or pH) may be controlled such that the mixture of calcitonin drug-oligomer conjugates resulting from the reaction of the mixture of activated oligomers where each oligomer has the same molecular weight and has a structure of the oligomer of Formula A and the mixture of calcitonin drugs is a mixture of conjugates where each conjugate has the same molecular weight and has the structure Formula A. For example, conjugation at the amino functionality of lysine may be suppressed by maintaining the pH of the reaction solution below the $pK_a$ of lysine. Alternatively, the mixture of calcitonin drug-oligomer conjugates may be separated and isolated utilizing, for example, HPLC to provide a mixture of calcitonin drug-oligomer conjugates, for example mono-, di-, or tri-conjugates, where each conjugate in the mixture has the same number molecular weight and has the structure of Formula A. The degree of conjugation (e.g., whether the isolated molecule is a mono-, di-, or tri-conjugate) of a particular isolated conjugate may be determined and/or verified utilizing various techniques as will be understood by those skilled in the art including, but not limited to, mass spectroscopy. The particular conjugate structure (e.g., whether the oligomer is at $Lys^{11}$, $Lys^{18}$ or the N-terminus of a salmon calcitonin monoconjugate) may be determined and/or verified utilizing various techniques as will be understood by those skilled in the art including, but not limited to, sequence analysis, peptide mapping, selective enzymatic cleavage, and/or endopeptidase cleavage.

As will be understood by those skilled in the art, one or more of the reaction sites on the calcitonin drug may be blocked by, for example, reacting the calcitonin drug with a suitable blocking reagent such as N-tert-butoxycarbonyl (t-BOC), or N-(9-fluorenylmethoxycarbonyl) (N-FMOC). This process may be preferred, for example, when the calcitonin drug is a polypeptide and it is desired to form an unsaturated conjugate (i.e., a conjugate wherein not all nucleophilic residues are conjugated) having an oligomer at the N-terminus of the polypeptide. Following such blocking, the mixture of blocked calcitonin drugs may be reacted with the mixture of activated oligomers where each oligomer in the mixture has the same molecular weight and has a structure of the oligomer of Formula A to provide a mixture of calcitonin drug-oligomer conjugates having oligomer(s) coupled to one or more nucleophilic residues and having blocking moieties coupled to other nucleophilic residues. After the conjugation reaction, the calcitonin drug-oligomer conjugates may be de-blocked as will be understood by those skilled in the art. If necessary, the mixture of calcitonin drug-oligomer conjugates may then be separated as described above to provide a mixture of calcitonin drug-oligomer conjugates where each conjugate in the mixture has the same number molecular weight and has the structure of Formula A. Alternatively, the mixture of calcitonin drug-oligomer conjugates may be separated prior to de-blocking.

Mixtures of calcitonin drug-oligomer conjugates where each conjugate in the mixture has the same molecular weight and has the structure of Formula A according to embodiments of the present invention preferably have improved properties when compared with those of conventional mixtures. For example, a mixture of calcitonin drug-oligomer conjugates where each conjugate in the mixture has the same molecular weight and has the structure of Formula A preferably is capable of lowering serum calcium levels by at least 5 percent. Preferably, the mixture of conjugates is capable of lowering serum calcium levels by at least 10, 11, 12, 13 or 14 percent. More preferably, the mixture of conjugates is capable of lowering serum calcium levels by at least 15, 16, 17, 18 or 19 percent, and, most preferably, the mixture of conjugates is capable of lowering serum calcium levels by at least 20 percent.

As another example, a mixture of calcitonin drug-oligomer conjugates where each conjugate in the mixture has the same molecular weight and has the structure of Formula A preferably has an increased resistance to degradation by chymotrypsin and/or trypsin when compared to the resistance to degradation by chymotrypsin and/or trypsin, respectively, of the calcitonin drug which is not coupled to the oligomer. Resistance to chymotrypsin or trypsin corresponds to the percent remaining when the molecule to be tested is digested in the applicable enzyme using a procedure similar to the one outlined in Example 51 below. Preferably, the resistance to degradation by chymotrypsin of the mixture of calcitonin drug-oligomer conjugates is about 10 percent greater than the resistance to degradation by chymotrypsin of the mixture of calcitonin drugs that is not conjugated with the oligomer. More preferably, the resistance to degradation by chymotrypsin of the mixture of calcitonin drug-oligomer conjugates is about 15 percent greater than the resistance to degradation by chymotrypsin of the mixture of calcitonin drug that is not conjugated with the oligomer, and, most preferably, the resistance to degradation by chymotrypsin of the mixture of calcitonin drug-oligomer conjugates is about 20 percent greater than the resistance to degradation by chymotrypsin of the mixture of calcitonin drug that is not conjugated with the oligomer. Preferably, the resistance to degradation by trypsin of the mixture of calcitonin drug-oligomer conjugates is about 10 percent greater than the resistance to degradation by trypsin of the mixture of calcitonin drug that is not conjugated with the oligomer. More preferably, the resistance to degradation by trypsin of the mixture of calcitonin drug-oligomer conjugates is about 20 percent greater than the resistance to degradation by trypsin of the mixture of calcitonin drug that is not conjugated with the oligomer, and, most preferably, the resistance to degradation by trypsin of the mixture of calcitonin drug-oligomer conjugates is about 30 percent greater than the resistance to degradation by trypsin of the mixture of calcitonin drug that is not conjugated with the oligomer.

As still another example, a mixture of calcitonin drug-oligomer conjugates where each conjugate in the mixture has the same molecular weight and has the structure of Formula A preferably has a higher bioefficacy than the bioefficacy of the calcitonin drug which is not coupled to the oligomer. The bioefficacy of a particular compound corresponds to its area-under-the-curve (AUC) value. Preferably, the bioefficacy of the mixture is about 5 percent greater than the bioefficacy of the calcitonin drug which is not coupled to the oligomer. More preferably, the bioefficacy of the mixture is about 10 percent greater than the bioefficacy of the calcitonin drug which is not coupled to the oligomer.

As yet another example, a mixture of calcitonin drug-oligomer conjugates where each conjugate in the mixture has the same molecular weight and has the structure of Formula A preferably has an in vivo activity that is greater than the in vivo activity of a polydispersed mixture of calcitonin drug-oligomer conjugates having the same number average molecular weight as the mixture of calcitonin drug-oligomer conjugates where each conjugate in the mixture has the same molecular weight and has the structure of Formula A. As will be understood by those skilled in the art, the number average molecular weight of a mixture may be measured by various methods including, but not limited to, size exclusion chromatography such as gel permeation chromatography as described, for example, in H. R. Allcock & F. W. Lampe, CONTEMPORARY POLYMER CHEMISTRY 394–402 (2d. ed., 1991).

As another example, a mixture of calcitonin drug-oligomer conjugates where each conjugate in the mixture has the same molecular weight and has the structure of Formula A preferably has an in vitro activity that is greater than the in vitro activity of a polydispersed mixture of calcitonin drug-oligomer conjugates having the same number average molecular weight as the mixture of calcitonin drug-oligomer conjugates where each conjugate in the mixture has the same molecular weight and has the structure of Formula A. As will be understood by those skilled in the art, the number average molecular weight of a mixture may be measured by various methods including, but not limited to, size exclusion chromatography.

As still another example, a mixture of calcitonin drug-oligomer conjugates where each conjugate in the mixture has the same molecular weight and has the structure of Formula A preferably has an increased resistance to degradation by chymotrypsin and/or trypsin when compared to the resistance to degradation by chymotrypsin and/or trypsin of a polydispersed mixture of calcitonin drug-oligomer conjugates having the same number average molecular weight as the mixture of calcitonin drug-oligomer conjugates where each conjugate in the mixture has the same molecular weight and has the structure of Formula A. As will be understood by those skilled in the art, the number average molecular weight of a mixture may be measured by various methods including, but not limited to, size exclusion chromatography.

As yet another example, a mixture of calcitonin drug-oligomer conjugates where each conjugate in the mixture has the same molecular weight and has the structure of Formula A preferably has an inter-subject variability that is less than the inter-subject variability of a polydispersed mixture of calcitonin drug-oligomer conjugates having the same number average molecular weight as the mixture of calcitonin drug-oligomer conjugates where each conjugate in the mixture has the same molecular weight and has the structure of Formula A. As will be understood by those skilled in the art, the number average molecular weight of a mixture may be measured by various methods including, but not limited to, size exclusion chromatography. The inter-subject variability may be measured by various methods, as will be understood by those skilled in the art. The inter-subject variability is preferably calculated as follows. The area under a dose response curve (AUC) (i.e., the area between the dose-response curve and a baseline value) is determined for each subject. The average AUC for all subjects is determined by summing the AUCs of each subject and dividing the sum by the number of subjects. The absolute value of the difference between the subject's AUC and the average AUC is then determined for each subject. The absolute values of the differences obtained are then summed to give a value that represents the inter-subject variability. Lower values represent lower inter-subject variabilities and higher values represent higher inter-subject variabilities.

Mixtures of calcitonin drug-oligomer conjugates where each conjugate in the mixture has the same molecular weight and has the structure of Formula A according to embodiments of the present invention preferably have two or more of the above-described improved properties. More preferably, mixtures of calcitonin drug-oligomer conjugates where each conjugate in the mixture has the same molecular weight and has the structure of Formula A according to embodiments of the present invention have three or more of the above-described improved properties. Most preferably, mixtures of calcitonin drug-oligomer conjugates where each conjugate in the mixture has the same molecular weight and has the structure of Formula A according to embodiments of the present invention have four or more of the above-described improved properties.

Pharmaceutical compositions comprising a conjugate mixture according to embodiments of the present invention are also provided. The mixtures of calcitonin drug-oligomer conjugates described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical composition according to embodiments of the present invention, the mixture of calcitonin drug-oligomer conjugates is typically admixed with, inter alia, a pharmaceutically acceptable carrier. The carrier must, of course, be acceptable in the sense of being compatible with any other ingredients in the pharmaceutical composition and should not be deleterious to the patient. The carrier may be a solid or a liquid, or both, and is preferably formulated with the mixture of calcitonin drug-oligomer conjugates as a unit-dose formulation, for example, a tablet, which may contain from about 0.01 or 0.5% to about 95% or 99% by weight of the mixture of calcitonin drug-oligomer conjugates. The pharmaceutical compositions may be prepared by any of the well known techniques of pharmacy including, but not limited to, admixing the components, optionally including one or more accessory ingredients.

The pharmaceutical compositions according to embodiments of the present invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, inracerebral, intraarterial, or intravenous), topical (i.e., both skin and mucosal surfaces, including airway surfaces) and transdermal administration, although the most suitable route in any given case will depend on the nature and severity of the condition being treated and on the nature of the particular mixture of calcitonin drug-oligomer conjugates which is being used.

Pharmaceutical compositions suitable for oral administration may be presented in discrete units, such as capsules, cachets, lozenges, or tables, each containing a predetermined amount of the mixture of calcitonin drug-oligomer conjugates; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the mixture of calcitonin drug-oligomer conjugates and a suitable carrier (which may contain one or more accessory ingredients as noted above). In general, the pharmaceutical composition according to embodiments of the present invention are prepared by uniformly and intimately admixing the mixture of calcitonin drug-oligomer conjugates with a liquid or finely divided solid carrier, or both, and then, if necessary, shaping the resulting mixture. For example, a tablet may be prepared by compressing or molding a powder or granules containing the mixture of calcitonin drug-oligomer conjugates, optionally with one or more accessory ingredients. Compressed tablets may be prepared by compressing, in a suitable machine, the mixture in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Pharmaceutical compositions suitable for buccal (sub-lingual) administration include lozenges comprising the mixture of calcitonin drug-oligomer conjugates in a flavoured base, usually sucrose and acacia or tragacanth; and pastilles comprising the mixture of calcitonin drug-oligomer conjugates in an inert base such as gelatin and glycerin or sucrose and acacia.

Pharmaceutical compositions according to embodiments of the present invention suitable for parenteral administration comprise sterile aqueous and non-aqueous injection solutions of the mixture of calcitonin drug-oligomer conjugates, which preparations are preferably isotonic with the blood of the intended recipient. These preparations may contain anti-oxidants, buffers, bacteriostats and solutes which render the composition isotonic with the blood of the intended recipient. Aqueous and non-aqueous sterile suspensions may include suspending agents and thickening agents. The compositions may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, an injectable, stable, sterile composition comprising a mixture of calcitonin drug-oligomer conjugates in a unit dosage form in a sealed container may be provided. The mixture of calcitonin drug-oligomer conjugates is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the mixture of calcitonin drug-oligomer conjugates. When the mixture of calcitonin drug-oligomer conjugates is substantially water-insoluble, a sufficient amount of emulsifying agent which is physiologically acceptable may be employed in sufficient quantity to emulsify the mixture of calcitonin drug-oligomer conjugates in an aqueous carrier. One such useful emulsifying agent is phosphatidyl choline.

Pharmaceutical compositions suitable for rectal administration are preferably presented as unit dose suppositories. These may be prepared by admixing the mixture of calcitonin drug-oligomer conjugates with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3 (6):318 (1986)) and typically take the form of an optionally buffered aqueous solution of the mixture of calcitonin drug-oligomer conjugates. Suitable formulations comprise citrate or bis\tris buffer (pH 6) or ethanol/water and contain from 0.1 to 0.2M active ingredient.

Methods of treating a bone disorder in a subject in need of such treatment by administering an effective amount of such pharmaceutical compositions are also provided. The bone disorder is preferably characterized by excessive osteoclastic bone resorption and/or hypercalcemic serum effects. Bone disorders that may be treated and/or prevented by methods of the present invention include, but are not limited to, osteoporosis, Paget's disease, and hypercalcemia.

The effective amount of any mixture of calcitonin drug-oligomer conjugates, the use of which is in the scope of present invention, will vary somewhat from mixture to mixture, and patient to patient, and will depend upon factors such as the age and condition of the patient and the route of delivery. Such dosages can be determined in accordance with routine pharmacological procedures known to those skilled in the art. As a general proposition, a dosage from about 0.1 to about 50 mg/kg will have therapeutic efficacy, with all weights being calculated based upon the weight of the mixture of calcitonin drug-oligomer conjugates. Toxicity concerns at the higher level may restrict intravenous dosages to a lower level such as up to about 10 mg/kg, with all weights being calculated based upon the weight of the active base. A dosage from about 10 mg/kg to about 50 mg/kg may be employed for oral administration. Typically, a dosage from about 0.5 mg/kg to 5 mg/kg may be employed for intramuscular injection. The frequency of administration is usually one, two, or three times per day or as necessary to control the condition. Alternatively, the drug-oligomer conjugates may be administered by continuous infusion. The duration of treatment depends on the type of bone disorder being treated and may be for as long as the life of the patient.

Methods of synthesizing conjugate mixtures according to embodiments of the present invention are also provided. While the following embodiments of a synthesis route are directed to synthesis of a monodispersed mixture, similar synthesis routes may be utilized for synthesizing other calcitonin drug-oligomer conjugate mixtures according to embodiments of the present invention.

A substantially monodispersed mixture of polymers comprising polyethylene glycol moieties is provided as illustrated in reaction 1:

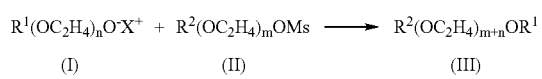

(I)　　　(II)　　　(III)

$R^1$ is H or a lipophilic moiety. $R^1$ is preferably H, alkyl, aryl alkyl, an aromatic moiety, a fatty acid moiety, an ester of a fatty acid moiety, cholesteryl, or adamantyl. $R^1$ is more preferably H, lower alkyl, or an aromatic moiety. $R^1$ is most preferably H, methyl, or benzyl.

In Formula I, n is from 1 to 25. Preferably n is from 1 to 6.

$X^+$ is a positive ion. Preferably $X^+$ is any positive ion in a compound, such as a strong base, that is capable of ionizing a hydroxyl moiety on PEG. Examples of positive ions include, but are not limited to, sodium ions, potassium ions, lithium ions, cesium ions, and thallium ions.

$R^2$ is H or a lipophilic moiety. $R^2$ is preferably linear or branched alkyl, aryl alkyl, an aromatic moiety, a fatty acid moiety, or an ester of a fatty acid moiety. $R^2$ is more preferably lower alkyl, benzyl, a fatty acid moiety having 1 to 24 carbon atoms, or an ester of a fatty acid moiety having 1 to 24 carbon atoms. $R^2$ is most preferably methyl, a fatty acid moiety having 1 to 18 carbon atoms or an ethyl ester of a fatty acid moiety having 1 to 18 carbon atoms.

In Formula II, m is from 1 to 25. Preferably m is from 1 to 6.

Ms is a mesylate moiety (i.e., $CH_3S(O_2)$—).

As illustrated in reaction 1, a mixture of compounds having the structure of Formula I is reacted with a mixture of compounds having the structure of Formula II to provide a mixture of polymers comprising polyethylene glycol moieties and having the structure of Formula III. The mixture of compounds having the structure of Formula I is a substantially monodispersed mixture. Preferably, at least about 96, 97, 98 or 99 percent of the compounds in the mixture of compounds of Formula I have the same molecular weight, and, more preferably, the mixture of compounds of Formula I is a monodispersed mixture. The mixture of compounds of Formula II is a substantially monodispersed mixture. Preferably, at least about 96, 97, 98 or 99 percent of the compounds in the mixture of compounds of Formula II have the same molecular weight, and, more preferably, the mixture of compounds of Formula II is a monodispersed mixture. The mixture of compounds of Formula III is a substantially monodispersed mixture. Preferably, at least about 96, 97, 98 or 99 percent of the compounds in the mixture of compound of Formula III have the same molecular weight. More preferably, the mixture of compounds of Formula III is a monodispersed mixture.

Reaction 1 is preferably performed between about 0° C. and about 40° C., is more preferably performed between about 15° C. and about 35° C., and is most preferably performed at room temperature (approximately 25° C.).

Reaction 1 may be performed for various periods of time as will be understood by those skilled in the art. Reaction 1 is preferably performed for a period of time between about 0.25, 0.5 or 0.75 hours and about 2, 4 or 8 hours.

Reaction 1 is preferably carried out in an aprotic solvent such as, but not limited to, N,N-dimethylacetamide (DMA), N,N-dimethylformamide (DMF), dimethyl sulfoxide (DMSO), hexamethylphosphoric triamide, tetrahydrofuran (THF), dioxane, diethyl ether, methyl t-butyl ether (MTBE), toluene, benzene, hexane, pentane, N-methylpyrollidinone, tetrahydronaphthalene, decahydronaphthalene, 1,2-dichlorobenzene, 1,3-dimethyl-2-imidazolidinone, or a mixture thereof. More preferably, the solvent is DMF, DMA or toluene.

The molar ratio of the compound of Formula I to the compound of Formula II is preferably greater than about 1:1. More preferably, the molar ratio is at least about 2:1. By providing an excess of the compounds of Formula I, one can ensure that substantially all of the compounds of Formula II are reacted, which may aid in the recovery of the compounds of Formula III as discussed below.

Compounds of Formula I are preferably prepared as illustrated in reaction 2:

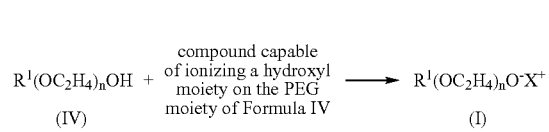

$R^1$ and $X^+$ are as described above and the mixture of compounds of Formula IV is substantially monodispersed; preferably, at least about 96, 97, 98 or 99 percent of the compounds in the mixture of compounds of Formula IV have the same molecular weight; and, more preferably, the mixture of compounds of Formula IV is a monodispersed mixture.

Various compounds capable of ionizing a hydroxyl moiety on the PEG moiety of the compound of Formula IV will be understood by those skilled in the art. The compound capable of ionizing a hydroxyl moiety is preferably a strong base. More preferably, the compound capable of ionizing a hydroxyl moiety is selected from the group consisting of sodium hydride, potassium hydride, sodium t-butoxide, potassium t-butoxide, butyl lithium (BuLi), and lithium diisopropylamine. The compound capable of ionizing a hydroxyl moiety is more preferably sodium hydride.

The molar ratio of the compound capable of ionizing a hydroxyl moiety on the PEG moiety of the compound of Formula IV to the compound of Formula IV is preferably at least about 1:1, and is more preferably at least about 2:1. By providing an excess of the compound capable of ionizing the hydroxyl moiety, it is assured that substantially all of the compounds of Formula IV are reacted to provide the compounds of Formula I. Thus, separation difficulties, which may occur if both compounds of Formula IV and compounds of Formula I were present in the reaction product mixture, may be avoided.

Reaction 2 is preferably performed between about 0° C. and about 40° C., is more preferably performed between about 0° C. and about 35° C., and is most preferably performed between about 0° C. and room temperature (approximately 25° C.).

Reaction 2 may be performed for various periods of time as will be understood by those skilled in the art. Reaction 2 is preferably performed for a period of time between about 0.25, 0.5 or 0.75 hours and about 2, 4 or 8 hours.

Reaction 2 is preferably carried out in an aprotic solvent such as, but not limited to, N,N-dimethylacetamide (DMA), N,N-dimethylformamide (DMF), dimethyl sulfoxide (DMSO), hexamethylphosphoric triamide, tetrahydrofuran (THF), dioxane, diethyl ether, methyl t-butyl ether (MTBE), toluene, benzene, hexane, pentane, N-methylpyrollidinone, dichloromethane, chloroform, tetrahydronaphthalene, decahydronaphthalene, 1,2-dichlorobenzene, 1,3-dimethyl-2-imidazolidinone, or a mixture thereof. More preferably, the solvent is DMF, dichloromethane or toluene.

Compounds of Formula II are preferably prepared as illustrated in reaction 3:

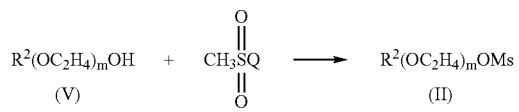

$R^2$ and Ms are as described above and the compound of Formula V is present as a substantially monodispersed mixture of compounds of Formula V; preferably at least about 96, 97, 98 or 99 percent of the compounds in the mixture of compounds of Formula V have the same molecular weight; and, more preferably, the mixture of compounds of Formula V is a monodispersed mixture.

Q is a halide? preferably chloride or fluoride.

$CH_3S(O_2)Q$ is methanesulfonyl halide. The methanesulfonyl halide is preferably methanesulfonyl chloride or methanesulfonyl fluoride. More preferably, the methanesulfonyl halide is methanesulfonyl chloride.

The molar ratio of the methane sulfonyl halide to the compound of Formula V is preferably greater than about 1:1, and is more preferably at least about 2:1. By providing an excess of the methane sulfonyl halide, it is assured that substantially all of the compounds of Formula V are reacted to provide the compounds of Formula II. Thus, separation difficulties, which may occur if both compounds of Formula V and compounds of Formula II were present in the reaction product mixture, may be avoided.

Reaction 3 is preferably performed between about −10° C. and about 40° C., is more preferably performed between about 0° C. and about 35° C., and is most preferably performed between about 0° C. and room temperature (approximately 25° C.).

Reaction 3 may be performed for various periods of time as will be understood by those skilled in the art. Reaction 3 is preferably performed for a period of time between about 0.25, 0.5 or 0.75 hours and about 2, 4 or 8 hours.

Reaction 3 is preferably carried out in the presence of an aliphatic amine including, but not limited to, monomethylamine, dimethylamine, trimethylamine, monoethylamine, diethylamine, triethylamine, monoisopropylamine, diisopropylamine, mono-n-butylamine, di-n-butylamine, tri-n-butylamine, monocyclohexylamine, dicyclohexylamine, or mixtures thereof. More preferably, the aliphatic amine is a tertiary amine such as triethylamine.

As will be understood by those skilled in the art, various substantially monodispersed mixtures of compounds of Formula V are commercially available. For example, when $R^2$ is H or methyl, the compounds of Formula V are PEG or mPEG compounds, respectively, which are commercially available from Aldrich of Milwaukee, Wis.; Fluka of Switzerland, and/or TCl America of Portland, Oreg.

When $R^2$ is a lipophilic moiety such as, for example, higher alkyl, fatty acid, an ester of a fatty acid, cholesteryl, or adamantyl, the compounds of Formula V may be provided by various methods as will be understood by those skilled in the art. The compounds of Formula V are preferably provided as follows:

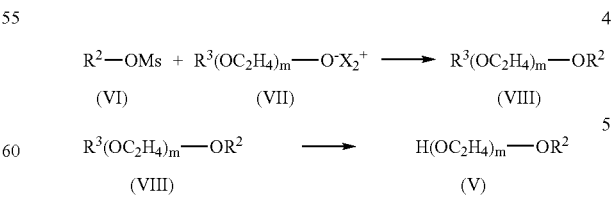

$R^2$ is a lipophilic moiety, preferably higher alkyl, fatty acid ester, cholesteryl, or adamantyl, more preferably a lower alkyl ester of a fatty acid, and most preferably an ethyl ester of a fatty acid having from 1 to 18 carbon atoms.

$R^3$ is H, benzyl, trityl, tetrahydropyran, or other alcohol protecting groups as will be understood by those skilled in the art.

$X_2^+$ is a positive ion as described above with respect to $X^+$.

The value of m is as described above.

Regarding reaction 4, a mixture of compounds of Formula VI is reacted with a mixture of compounds of Formula VII under reaction conditions similar to those described above with reference to reaction 1. The mixture of compounds of Formula VI is a substantially monodispersed mixture. Preferably, at least about 96, 97, 98 or 99 percent of the compounds in the mixture of compounds of Formula VI have the same molecular weight. More preferably, the mixture of compounds of Formula VI is a monodispersed mixture. The mixture of compounds of Formula VII is a substantially monodispersed mixture. Preferably, at least about 96, 97, 98 or 99 percent of the compounds in the mixture of compounds of Formula VII have the same molecular weight. More preferably, the mixture of compounds of Formula VII is a monodispersed mixture.

Regarding reaction 5, the compound of Formula VIII may be hydrolyzed to convert the $R^3$ moiety into an alcohol by various methods as will be understood by those skilled in the art. When $R^3$ is benzyl or trityl, the hydrolysis is preferably performed utilizing $H_2$ in the presence of a palladium-charcoal catalyst as is known by those skilled in the art. Of course, when $R^3$ is H, reaction 5 is unnecessary.

The compound of Formula VI may be commercially available or be provided as described above with reference to reaction 3. The compound of Formula VII may be provided as described above with reference to reaction 2.

Substantially monodispersed mixtures of polymers comprising PEG moieties and having the structure of Formula III above can further be reacted with other substantially monodispersed polymers comprising PEG moieties in order to extend the PEG chain. For example, the following scheme may be employed:

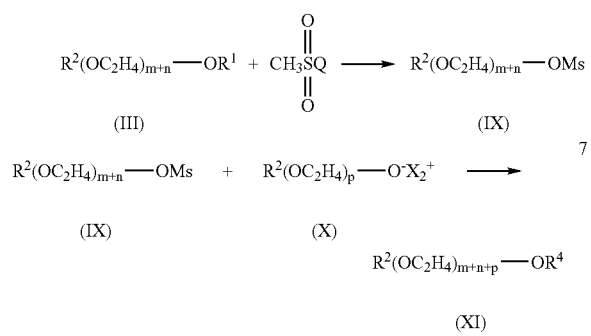

Ms, m and n are as described above with reference to reaction 1; p is similar to n and m, and $X_2^+$ is similar to $X^+$ as described above with reference to reaction 1. Q is as described above with reference to reaction 3. $R^2$ is as described above with reference to reaction 1 and is preferably lower alkyl. $R^1$ is H. Reaction 6 is preferably performed in a manner similar to that described above with reference to reaction 3. Reaction 7 is preferably performed in a manner similar to that described above with reference to reaction 1. Preferably, at least about 96, 97, 98 or 99 percent of the compounds in the mixture of compounds of Formula III have the same molecular weight, and, more preferably, the mixture of compounds of Formula III is a monodispersed mixture. The mixture of compounds of Formula X is a substantially monodispersed mixture. Preferably, at least about 96, 97, 98 or 99 percent of the compounds in the mixture of compounds of Formula X have the same molecular weight, and, more preferably, the mixture of compounds of Formula X is a monodispersed mixture.

A process according to embodiments of the present invention is illustrated by the scheme shown in FIG. 1, which will now be described. The synthesis of substantially monodispersed polyethylene glycol-containing oligomers begins by the preparation of the monobenzyl ether (1) of a substantially monodispersed polyethylene glycol. An excess of a commercially available substantially monodispersed polyethylene glycol is reacted with benzyl chloride in the presence of aqueous sodium hydroxide as described by Coudert et al (*Synthetic Communications*, 16(1): 19–26 (1986)). The sodium salt of 1 is then prepared by the addition of NaH, and this sodium salt is allowed to react with the mesylate synthesized from the ester of a hydroxyalkanoic acid (2). The product (3) of the displacement of the mesylate is debenzylated via catalytic hydrogenation to obtain the alcohol (4). The mesylate (5) of this alcohol may be prepared by addition of methanesulfonyl chloride and used as the electrophile in the reaction with the sodium salt of the monomethyl ether of a substantially monodispersed polyethylene glycol derivative, thereby extending the polyethylene glycol portion of the oligomer to the desired length, obtaining the elongated ester (6). The ester may be hydrolyzed to the acid (7) in aqueous base and transformed into the activated ester (8) by reaction with a carbodiimide and N-hydroxysuccinimide. While the oligomer illustrated in FIG. 1 is activated using N-hydroxysuccinimide, it is to be understood that various other reagents may be used to activate oligomers of the present invention including, but not limited to, active phenyl chloroformates such as para-nitrophenyl chloroformate, phenyl chloroformate, 3,4-phenyldichloroformate, and 3,4-phenyldichloroformate; tresylation; and acetal formation.

Still referring to FIG. 1, q is from 1 to 24. Preferably, q is from 1 to 18, and q is more preferably from 4 to 16. $R^4$ is a moiety capable of undergoing hydrolysis to provide the carboxylic acid. $R^4$ is preferably lower alkyl and is more preferably ethyl. The variables n and m are as described above with reference to reaction 1.

All starting materials used in the procedures described herein are either commercially available or can be prepared by methods known in the art using commercially available starting materials.

The present invention will now be described with reference to the following examples. It should be appreciated that these examples are for the purposes of illustrating aspects of the present invention, and do not limit the scope of the invention as defined by the claims.

EXAMPLES

Examples 1 through 10

Figure 2:
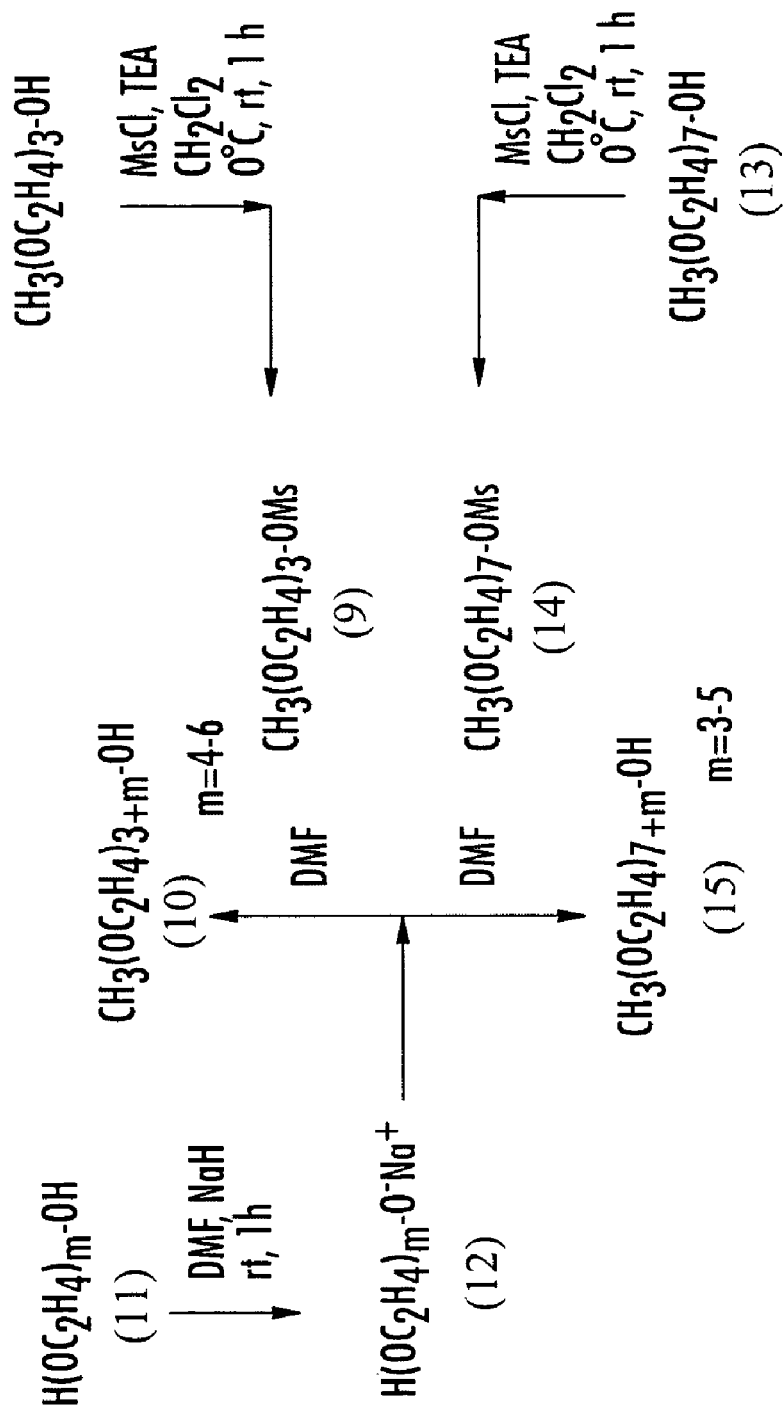
FIG. 2 illustrates a scheme for synthesizing a mixture of mPEG according to embodiments of the present invention.

Reactions in Examples 1 through 10 were carried out under nitrogen with magnetic stirring, unless otherwise specified. "Work-up" denotes extraction with an organic solvent, washing of the organic phase with saturated NaCl solution, drying (MgSO$_4$), and evaporation (rotary evaporator). Thin layer chromatography was conducted with Merck glass plates precoated with silica gel 60° F.-254 and spots were visualized by iodine vapor. All mass spectra were determined by Macromolecular Resources Colorado State University, CO and are reported in the order m/z, (relative intensity). Elemental analyses and melting points were performed by Galbraith Laboratories, Inc., Knoxyille, Tenn. Examples 1–10 refer to the scheme illustrated in FIG. 2.

Example 1

8-Methoxy-1-(methylsulfonyl)oxy-3,6-dioxaoctane (9)

A solution of non-polydispersed triethylene glycol monomethyl ether molecules (4.00 mL, 4.19 g, 25.5 mmol) and triethylamine (4.26 mL, 3.09 g, 30.6 mmol) in dry dichloromethane (50 mL) was chilled in an ice bath and place under a nitrogen atmosphere. A solution of methanesulfonyl chloride (2.37 mL, 3.51 g, 30.6 mmol) in dry dichloromethane (20 mL) was added dropwise from an addition funnel. Ten minutes after the completion of the chloride addition, the reaction mixture was removed from the ice bath and allowed to come to room temperature. The mixture was stirred for an additional hour, at which time TLC ($CHCl_3$ with 15% MeOH as the elutant) showed no remaining triethylene glycol monomethyl ether.

The reaction mixture was diluted with another 75 mL of dichloromethane and washed successively with saturated $NaHCO_3$, water and brine. The organics were dried over $Na_2SO_4$, filtered and concentrated in vacuo to give a non-polydispersed mixture of compounds 9 as a clear oil (5.31 g, 86%).

Example 2

Ethylene Glycol Mono Methyl Ether (10) (m=4,5,6)

To a stirred solution of non-polydispersed compound 11 (35.7 mmol) in dry DMF (25.7 mL), under $N_2$ was added in portion a 60% dispersion of NaH in mineral oil, and the mixture was stirred at room temperature for 1 hour. To this salt 12 was added a solution of non-polydispersed mesylate 9 (23.36) in dry DMF (4 ml) in a single portion, and the mixture was stirred at room temperature for 3.5 hours. Progress of the reaction was monitored by TLC (12% $CH_3OH$—$CHCl_3$). The reaction mixture was diluted with an equal amount of 1N HCl, and extracted with ethyl acetate (2×20 ml) and discarded. Extraction of aqueous solution and work-up gave non-polydispersed polymer 10 (82–84% yield).

Example 3

3,6,9,12,15,18,21-Heptaoxadocosanol (10) (m=4)

Oil; Rf 0.46 (methanol:chloroform=3:22); MS m/z calc'd for $C_{15}H_{32}O_8$ 340.21 ($M^+$+1), found 341.2.

Example 4

3,6,9,12,15,18,21,24-Octaoxapentacosanol (10) (m=5)

Oil; Rf 0.43 (methanol:chloroform=6:10); MS m/z calc'd for $C_{17}H_{36}O_9$ 384.24 ($M^+$+1), found 385.3.

Example 5

3,6,9,12,15,18,21,24,27-Nonaoxaoctacosanol (10) (m=6)

Oil; Rf 0.42 (methanol:chloroform=6:10); MS m/z calc'd for $C_{19}H_{40}O_{10}$ 428.26 ($M^+$+1), found 429.3.

Example 6

20-methoxy-1-(methylsulfonyl)oxy-3,6,9,12,15,18-hexaoxaeicosane (14)

Non-polydispersed compound 14 was obtained in quantitative yield from the alcohol 13 (m=4) and methanesulfonyl chloride as described for 9, as an oil; Rf 0.4 (ethyl acetate:acetonitrile=1:5); MS m/z calc'd for $C_{17}H_{37}O_{10}$ 433.21 ($M^+$+1), found 433.469.

Example 7

Ethylene Glycol Mono Methyl Ether (15) (m=3,4,5)

The non-polydispersed compounds 15 were prepared from a diol by using the procedure described above for compound 10.

Example 8

3,6,9,12,15,18,21,24,27,30-Decaoxaheneicosanol (15) (m=3)

Oil; Rf 0.41 (methanol:chloroform=6:10); MS m/z calc'd for $C_{21}H_{44}O_{11}$ 472.29 ($M^+$+1), found 472.29.

Example 9

3,6,9,12,15,18,21,24,27,30,33-Unecaoxatetratricosanol (15) (m=4)

Oil; Rf 0.41 (methanol:chloroform=6:10); MS m/z calc'd for $C_{23}H_{48}O_{12}$ 516.31 ($M^+$+1), found 516.31.

Example 10

3,6,9,12,15,18,21,24,27,30,33,36-Dodecaoxaheptatricosanol (15) (m=5) Oil; Rf 0.41 (methanol:chloroform=6:10); MS m/z calc'd for $C_{25}H_{52}O_{13}$ 560.67 (M++1), found 560.67.

Examples 11 through 18 refer to the scheme illustrated in FIG. 3.

Example 11

Hexaethylene Glycol Monobenzyl Ether (16)

An aqueous sodium hydroxide solution prepared by dissolving 3.99 g (100 mmol) NaOH in 4 ml water was added slowly to non-polydispersed hexaethylene glycol (28.175 g, 25 ml, 100 mmol). Benzyl chloride (3.9 g, 30.8 mmol, 3.54 ml) was added and the reaction mixture was heated with stirring to 100° C. for 18 hours. The reaction mixture was then cooled, diluted with brine (250 ml) and extracted with methylene chloride (200 ml×2). The combined organic layers were washed with brine once, dried over $Na_2SO_4$, filtered and concentrated in vacuo to a dark brown oil. The crude product mixture was purified via flash chromatography (silica gel, gradient elution: ethyl acetate to 9/1 ethyl acetate/methanol) to yield 8.099 g (70%) of non-polydispersed 16 as a yellow oil.

Example 12

Ethyl 6-methylsulfonyloxyhexanoate (17)

A solution of non-polydispersed ethyl 6-hydroxyhexanoate (50.76 ml, 50.41 g, 227 mmol) in dry dichloromethane (75 ml) was chilled in a ice bath and placed under a nitrogen atmosphere. Triethylamine (34.43 ml, 24.99 g, 247 mmol) was added. A solution of methanesulfonyl chloride (19.15 ml, 28.3 g, 247 mmol) in dry dichloromethane (75 ml) was added dropwise from an addition funnel. The mixture was stirred for three and one half hours, slowly being allowed to come to room temperature as the ice bath melted. The mixture was filtered through silica gel, and the filtrate was washed successively with water, saturated NaHCO$_3$, water and brine. The organics were dried over Na$_2$SO$_4$, filtered and concentrated in vacuo to a pale yellow oil. Final purification of the crude product was achieved by flash chromatography (silica gel, 1/1 hexanes/ethyl acetate) to give the non-polydispersed product (46.13 g, 85%) as a clear, colorless oil. FAB MS: m/e 239 (M+H), 193 (M-C$_2$H$_5$O).

Example 13

6-{2-[2-(2-{2-[2-(2-Benzyloxyethoxy)ethoxy]ethoxy}-ethoxy)-ethoxy]-ethoxy}-hexanoic acid ethyl ester (18)

Sodium hydride (3.225 g or a 60% oil dispersion, 80.6 mmol) was suspended in 80 ml of anhydrous toluene, placed under a nitrogen atmosphere and cooled in an ice bath. A solution of the non-polydispersed alcohol 16 (27.3 g, 73.3 mmol) in 80 ml dry toluene was added to the NaH suspension. The mixture was stirred at 0° C. for thirty minutes, allowed to come to room temperature and stirred for another five hours, during which time the mixture became a clear brown solution. The non-polydispersed mesylate 17 (19.21 g, 80.6 mmol) in 80 ml dry toluene was added to the NaH/alcohol mixture, and the combined solutions were stirred at room temperature for three days. The reaction mixture was quenched with 50 ml methanol and filtered through basic alumina. The filtrate was concentrated in vacuo and purified by flash chromatography (silica gel, gradient elution: 3/1 ethyl acetate/hexanes to ethyl acetate) to yield the non-polydispersed product as a pale yellow oil (16.52 g, 44%). FAB MS: m/e 515 (M+H).

Example 14

6-{2-[2-(2-{2-[2-(2-hydroxyethoxy)ethoxy]ethoxy}-ethoxy)-ethoxy]-ethoxy}-hexanoic acid ethyl ester (19)

Non-polydispersed benzyl ether 18 (1.03 g, 2.0 mmol) was dissolved in 25 ml ethanol. To this solution was added 270 mg 10% Pd/C, and the mixture was placed under a hydrogen atmosphere and stirred for four hours, at which time TLC showed the complete disappearance of the starting material. The reaction mixture was filtered through Celite 545 to remove the catalyst, and the filtrate was concentrated in vacuo to yield the non-polydispersed title compound as a clear oil (0.67 g, 79%). FAB MS: m/e 425 (M+H), 447 (M+Na).

Example 15

6-{2-[2-(2-{2-[2-(2-methylsulfonylethoxy)ethoxy]ethoxy}-ethoxy)-ethoxy]-ethoxy}-hexanoic acid ethyl ester (20)

The non-polydispersed alcohol 19 (0.835 g, 1.97 mmol) was dissolved in 3.5 ml dry dichloromethane and placed under a nitrogen atmosphere. Triethylamine (0.301 ml, 0.219 g, 2.16 mmol) was added and the mixture was chilled in an ice bath. After two minutes, the methanesulfonyl chloride (0.16 ml, 0.248 g, 2.16 mmol) was added. The mixture was stirred for 15 minutes at 0° C., then at room temperature for two hours. The reaction mixture was filtered through silica gel to remove the triethylammonium chloride, and the filtrate was washed successively with water, saturated NaHCO$_3$, water and brine. The organics were dried over Na$_2$SO$_4$, filtered and concentrated in vacuo. The residue was purified by column chromatography (silica gel, 9/1 ethyl acetate/methanol) to give non-polydispersed compound 20 as a clear oil (0.819 g, 83%). FAB MS: m/e 503 (M+H).

Example 16

6-(2-{2-[2-(2-{2-[2-(2-methoxyethoxy)ethoxy]-ethoxy}-ethoxy)-ethoxy]-ethoxy}-ethoxy)-hexanoic acid ethyl ester (21)

NaH (88 mg of a 60% dispersion in oil, 2.2 mmol) was suspended in anhydrous toluene (3 ml) under N$_2$ and chilled to 0° C. Non-polydispersed diethylene glycol monomethyl ether (0.26 ml, 0.26 g, 2.2 mmol) that had been dried via azeotropic distillation with toluene was added. The reaction mixture was allowed to warm to room temperature and stirred for four hours, during which time the cloudy grey suspension became clear and yellow and then turned brown. Mesylate 20 (0.50 g, 1.0 mmol) in 2.5 ml dry toluene was added. After stirring at room temperature over night, the reaction was quenched by the addition of 2 ml of methanol and the resultant solution was filtered through silica gel. The filtrate was concentrated in vacuo and the FAB MS: m/e 499 (M+H), 521 (M+Na). Additional purification by preparatory chromatography (silica gel, 19/3 chloroform/methanol) provided the non-polydispersed product as a clear yellow oil (0.302 g 57%). FAB MS: m/e 527 (M+H), 549 (M+Na).

Example 17

6-(2-{2-[2-(2-{2-[2-(2-methoxyethoxy)ethoxy]-ethoxy}-ethoxy)-ethoxy]-ethoxy}-ethoxy)-hexanoic acid (22)

Non-polydispersed ester 21 (0.25 g, 0.46 mmol) was stirred for 18 hours in 0.71 ml of 1 N NaOH. After 18 hours, the mixture was concentrated in vacuo to remove the alcohol and the residue dissolved in a further 10 ml of water. The aqueous solution was acidified to pH 2 with 2 N HCl and the product was extracted into dichloromethane (30 ml×2). The combined organics were then washed with brine (25 ml×2), dried over Na$_2$SO$_4$, filtered and concentrated in vacuo to yield the non-polydispersed title compound as a yellow oil (0.147 g, 62%). FAB MS: m/e 499 (M+H), 521 (M+Na).

Example 18

6-(2-{2-[2-(2-{2-[2-(2-methoxyethoxy)ethoxy]-ethoxy}-ethoxy)-ethoxy]-ethoxy}-ethoxy)- hexanoic acid 2,5-dioxo-pyrrolidin-1-yl ester (23)

Non-polydispersed acid 22 (0.209 g, 0.42 mmol) were dissolved in 4 ml of dry dichloromethane and added to a dry flask already containing NHS(N-hydroxysuccinimide) (57.8 mg, 0.502 mmol) and EDC (1-(3-dimethylaminopropyl)-3-ethylcarbodiimide hydrochloride) (98.0 mg, 0.502 mmol) under a $N_2$ atmosphere. The solution was stirred at room temperature overnight and filtered through silica gel to remove excess reagents and the urea formed from the EDC. The filtrate was concentrated in vacuo to provide the non-polydispersed product as a dark yellow oil (0.235 g, 94%). FAB MS: m/e 596 (M+H), 618 (M+Na).

Examples 19 through 24 refer to the scheme illustrated in FIG. 4.

Example 19

Mesylate of Triethylene Glycol Monomethyl Ether (24)

To a solution of $CH_2Cl_2$ (100 mL) cooled to 0° C. in an ice bath was added non-polydispersed triethylene glycol monomethyl ether (25 g, 0.15 mol). Then triethylamine (29.5 mL, 0.22 mol) was added and the solution was stirred for 15 min at 0° C., which was followed by dropwise addition of methanesulfonyl chloride (13.8 mL, 0.18 mol, dissolved in 20 mL $CH_2Cl_2$). The reaction mixture was stirred for 30 min at 0° C., allowed to warm to room temperature, and then stirred for 2 h. The crude reaction mixture was filtered through Celite (washed $CH_2Cl_2$~200 mL), then washed with $H_2O$ (300 mL), 5% $NaHCO_3$ (300 mL), $H_2O$ (300 mL), sat. NaCl (300 mL), dried $MgSO_4$, and evaporated to dryness. The oil was then placed on a vacuum line for ~2 h to ensure dryness and afforded the non-polydispersed title compound as a yellow oil (29.15 g, 80% yield).

Example 20

Heptaethylene Glycol Monomethyl Ether (25)

To a solution of non-polydispersed tetraethylene glycol (51.5 g, 0.27 mol) in THF (1 L) was added potassium t-butoxide (14.8 g, 0.13 mol, small portions over 30 min). The reaction mixture was then stirred for 1 h and then 24 (29.15 g, 0.12 mol) dissolved in THF (90 mL) was added dropwise and the reaction mixture was stirred overnight. The crude reaction mixture was filtered through Celite (washed $CH_2Cl_2$, ~200 mL) and evaporated to dryness. The oil was then dissolved in HCl (250 mL, 1N) and washed with ethyl acetate (250 mL) to remove excess 24. Additional washings of ethyl acetate (125 mL) may be required to remove remaining 24. The aqueous phase was washed repetitively with $CH_2Cl_2$ (125 mL volumes) until most of the 25 has been removed from the aqueous phase. The first extraction will contain 24, 25, and dicoupled side product and should be back extracted with HCl (125 mL, 1N). The organic layers were combined and evaporated to dryness. The resultant oil was then dissolved in $CH_2Cl_2$ (100 mL) and washed repetitively with $H_2O$ (50 mL volumes) until 25 was removed. The aqueous fractions were combined, total volume 500 mL, and NaCl was added until the solution became cloudy and then was washed with $CH_2Cl_2$ (2×500 mL). The organic layers were combined, dried $MgSO_4$, and evaporated to dryness to afford a the non-polydispersed title compound as an oil (16.9 g, 41% yield). It may be desirable to repeat one or more steps of the purification procedure to ensure high purity.

Example 21

8-Bromooctoanate (26)

To a solution of 8-bromooctanoic acid (5.0 g, 22 mmol) in ethanol (100 mL) was added $H_2SO_4$ (0.36 mL, 7.5 mmol) and the reaction was heated to reflux with stirring for 3 h. The crude reaction mixture was cooled to room temperature and washed $H_2O$ (100 mL), sat. $NaHCO_3$ (2×100 mL), $H_2O$ (100 mL), dried $MgSO_4$, and evaporated to dryness to afford a clear oil (5.5 g, 98% yield).

Example 22

Synthesis of MPEG7-C8 Ester (27)

To a solution of the non-polydispersed compound 25 (3.0 g, 8.8 mmol) in ether (90 mL) was added potassium t-butoxide (1.2 g, 9.6 mmol) and the reaction mixture was stirred for 1 h. Then dropwise addition of the non-polydispersed compound 26 (2.4 g, 9.6 mmol), dissolved in ether (10 mL), was added and the reaction mixture was stirred overnight. The crude reaction mixture was filtered through Celite (washed $CH_2Cl_2$, ~200 mL) and evaporated to dryness. The resultant oil was dissolved in ethyl acetate and washed $H_2O$ (2×200 mL), dried $MgSO_4$, and evaporated to dryness. Column chromatography (Silica, ethyl acetate to ethyl acetate/methanol, 10:1) was performed and afforded the non-polydispersed title compound as a clear oil (0.843 g, 19% yield).

Example 23

MPEG7-C8 Acid (28)

To the oil of the non-polydispersed compound 27 (0.70 g, 1.4 mmol) was added 1N NaOH (2.0 mL) and the reaction mixture was stirred for 4 h. The crude reaction mixture was concentrated, acidified (pH~2), saturated with NaCl, and washed $CH_2Cl_2$ (2×50 mL). The organic layers were combined, washed sat. NaCl, dried $MgSO_4$, and evaporated to dryness to afford the non-polydispersed title compound as a clear oil (0.35 g, 53% yield).

Example 24

Activation of MPEG7-C8 Acid (29)

Non-polydispersed mPEG7-C8-acid 28 (0.31 g, 0.64 mmol) was dissolved in 3 ml of anhydrous methylene chloride and then solution of N-hydroxysuccinimide (0.079 g, 0.69 mmol) and EDCI·HCl (135.6 mg, 0.71 mmol) in anhydrous methylene chloride added. Reaction was stirred for several hours, then washed with 1N HCl, water, dried over $MgSO_4$, filtered and concentrated. Crude material was purified by column chromatography, concentrated to afford the non-polydispersed title compound as a clear oil and dried via vacuum.

Examples 25 through 29 refer to the scheme illustrated in FIG. 5.

Example 25

10-hydroxydecanoate (30)

To a solution of non-polydispersed 10-hydroxydecanoic acid (5.0 g, 26.5 mmol) in ethanol (100 mL) was added $H_2SO_4$ (0.43 mL, 8.8 mmol) and the reaction was heated to reflux with stirring for 3 h. The crude reaction mixture was cooled to room temperature and washed $H_2O$ (100 mL), sat. $NaHCO_3$ (2×100 mL), $H_2O$ (100 mL), dried $MgSO_4$, and evaporated to dryness to afford the non-polydispersed title compound as a clear oil (6.9 g, 98% yield).

Example 26

Mesylate of 10-hydroxydecanoate (31)

To a solution of $CH_2Cl_2$ (27 mL) was added non-polydispersed 10-hydroxydecanoate 30 (5.6 g, 26 mmol) and cooled to 0° C. in an ice bath. Then triethylamine (5 mL, 37 mmol) was added and the reaction mixture was stirred for 15 min at 0° C. Then methanesulfonyl chloride (2.7 mL, 24 mmol) dissolved in $CH_2Cl_2$ (3 mL) was added and the reaction mixture was stirred at 0° C. for 30 min, the ice bath was removed and the reaction was stirred for an additional 2 h at room temperature. The crude reaction mixture was filtered through Celite (washed $CH_2Cl_2$, 80 mL) and the filtrate was washed $H_2O$ (100 mL), 5% $NaHCO_3$ (2×100 mL), $H_2O$ (100 mL), sat. NaCl (100 mL), dried $MgSO_4$, and evaporated to dryness to afford the non-polydispersed title compound as a yellowish oil (7.42 g, 97% yield).

Example 27

$MPEG_7$-$C_{10}$ Ester (32)

To a solution of non-polydispersed heptaethylene glycol monomethyl ether 25 (2.5 g, 7.3 mmol) in tetrahydrofuran (100 mL) was added sodium hydride (0.194 g, 8.1 mmol) and the reaction mixture was stirred for 1 h. Then dropwise addition of mesylate of non-polydispersed 10-hydroxydecanoate 31 (2.4 g, 8.1 mmol), dissolved in tetrahydrofuran (10 mL), was added and the reaction mixture was stirred overnight. The crude reaction mixture was filtered through Celite (washed $CH_2Cl_2$, ~200 mL) and evaporated to dryness. The resultant oil was dissolved in ethyl acetate and washed $H_2O$ (2×200 mL), dried $MgSO_4$, evaporated to dryness, chromatographed (silica, ethyl acetate/methanol, 10:1), and chromatographed (silica, ethyl acetate) to afford the non-polydispersed title compound as a clear oil (0.570 g, 15% yield).

Example 28

$MPEG_7$-$C_{10}$ Acid (33)

To the oil of non-polydispersed $mPEG_7$-$C_{10}$ ester 32 (0.570 g, 1.1 mmol) was added 1N NaOH (1.6 mL) and the reaction mixture was stirred overnight. The crude reaction mixture was concentrated, acidified (pH~2), saturated with NaCl, and washed $CH_2Cl_2$ (2×50 mL). The organic layers were combined, washed sat. NaCl (2×50 mL), dried $MgSO_4$, and evaporated to dryness to afford the non-polydispersed title compound as a clear oil (0.340 g, 62% yield).

Example 29

Activation of $MPEG_7$-$C_{10}$ Acid (34)

The non-polydispersed acid 33 was activated using procedures similar to those described above in Example 24.

Examples 30 and 31 refer to the scheme illustrated in FIG. 6.

Example 30

Synthesis of C18(PEG6) Oligomer (36)

Non-polydispersed stearoyl chloride 35 (0.7 g, 2.31 mmol) was added slowly to a mixture of PEG6 (5 g, 17.7 mmol) and pyridine (0.97 g, 12.4 mmol) in benzene. The reaction mixture was stirred for several hours (~5). The reaction was followed by TLC using ethylacetate/methanol as a developing solvent. Then the reaction mixture was washed with water, dried over $MgSO_4$, concentrated and dried via vacuum. Purified non-polydispersed compound 36 was analyzed by FABMS: m/e 549/$M^+H$.

Example 31

Activation of C18(PEG6) Oligomer

Activation of non-polydispersed C 18(PEG6) oligomer was accomplished in two steps:

1) Non-polydispersed stearoyl-PEG6 36 (0.8 g, 1.46 mmol) was dissolved in toluene and added to a phosgene solution (10 ml, 20% in toluene) which was cooled with an ice bath. The reaction mixture was stirred for 1 h at 0° C. and then for 3 h at room temperature. Then phosgene and toluene were distilled off and the remaining non-polydispersed stearoyl PEG6 chloroformate 37 was dried over $P_2O_5$ overnight.

2) To a solution of non-polydispersed stearoyl PEG6 chloroformate 36 (0.78 g, 1.27 mmol) and TEA (128 mg, 1.27 mmol) in anhydrous methylene chloride, N-hydroxy succinimide (NHS) solution in methylene chloride was added. The reaction mixture was stirred for 16 hours, then washed with water, dried over $MgSO_4$, filtered, concentrated and dried via vacuum to provide the non-polydispersed activated C18(PEG6) oligomer 38.

Examples 32 through 37 refer to the scheme illustrated in FIG. 7.

Example 32

Tetraethylene Glycol Monobenzylether (39)

To the oil of non-polydispersed tetraethylene glycol (19.4 g, 0.10 mol) was added a solution of NaOH (4.0 g in 4.0 mL) and the reaction was stirred for 15 mm. Then benzyl chloride (3.54 mL, 30.8 mmol) was added and the reaction mixture was heated to 100° C. and stirred overnight. The reaction mixture was cooled to room temperature, diluted with sat. NaCl (250 mL), and washed $CH_2Cl_2$ (2×200 mL). The organic layers were combined, washed sat. NaCl, dried $MgSO_4$, and chromatographed (silica, ethyl acetate) to afford the non-polydispersed title compound as a yellow oil (6.21 g, 71% yield).

Example 33

Mesylate of Tetraethylene Glycol Monobenzylether (40)

To a solution of $CH_2Cl_2$ (20 mL) was added non-polydispersed tetraethylene glycol monobenzylether 39 (6.21 g, 22 mmol) and cooled to 0° C. in an ice bath. Then triethylamine (3.2 mL, 24 mmol) was added and the reaction mixture was stirred for 15 min at 0° C. Then methanesulfonyl chloride (1.7 mL, 24 mmol) dissolved in $CH_2Cl_2$ (2 mL) was added and the reaction mixture was stirred at 0° C. for 30 min, the ice bath was removed and the reaction was stirred for an additional 2 h at room temperature. The crude reaction mixture was filtered through Celite (washed $CH_2Cl_2$, 80 mL) and the filtrate was washed $H_2O$ (100 mL), 5% $NaHCO_3$ (2×100 mL), $H_2O$ (100 mL), sat. NaCl (100 mL), and dried $MgSO_4$. The resulting yellow oil was chromatographed on a pad of silica containing activated carbon (10 g) to afford the non-polydispersed title compound as a clear oil (7.10 g, 89% yield).

Example 34

Octaethylene Glycol Monobenzylether (41)

To a solution of tetrahydrofuran (140 mL) containing sodium hydride (0.43 g, 18 mmol) was added dropwise a solution of non-polydispersed tetraethylene glycol (3.5 g, 18 mmol) in tetrahydrofuran (10 mL) and the reaction mixture was stirred for 1 h. Then mesylate of non-polydispersed tetraethylene glycol monobenzylether 40 (6.0 g, 16.5 mmol) dissolved in tetrahydrofuran (10 mL) was added dropwise and the reaction mixture was stirred overnight. The crude reaction mixture was filtered through Celite (washed, $CH_2Cl_2$, 250 mL) and the filtrate was washed $H_2O$, dried $MgSO_4$, and evaporated to dryness. The resultant oil was chromatographed (silica, ethyl acetate/methanol, 10:1) and chromatographed (silica, chloroform/methanol, 25:1) to afford the non-polydispersed title compound as a clear oil (2.62 g, 34% yield).

Example 35

Synthesis of Stearate PEG8-Benzyl (43)

To a stirred cooled solution of non-polydispersed octaethylene glycol monobenzylether 41 (0.998 g, 2.07 mmol) and pyridine (163.9 mg, 2.07 mmol) was added non-polydispersed stearoyl chloride 42 (627.7 mg, 2.07 mmol) in benzene. The reaction mixture was stirred overnight (18 hours). The next day the reaction mixture was washed with water, dried over $MgSO_4$, concentrated and dried via vacuum. Then the crude product was chromatographed on flash silica gel column, using 10% methanol/90% chloroform. The fractions containing the product were combined, concentrated and dried via vacuum to afford the non-polydispersed title compound.

Example 36

Hydrogenolysis of Stearate-PEG8-Benzyl

To a methanol solution of non-polydispersed stearate-PEG8-Bzl 43 (0.8$^5$4 g 1.138 mmol) Pd/C(10%) (palladium, 10% wt. on activated carbon) was added. The reaction mixture was stirred overnight (18 hours) under hydrogen. Then the solution was filtered, concentrated and purified by flash column chromatography using 10% methanol/90% chloroform, fractions with $R_f$=0.6 collected, concentrated and dried to provide the non-polydispersed acid 44.

Example 37

Activation of C18(PEG8) Oligomer

Two step activation of non-polydispersed stearate-PEG8 oligomer was performed as described for stearate-PEG6 in Example 31 above to provide the non-polydispersed activated C 18(PEG8) oligomer 45.

Example 38

Synthesis of Activated Triethylene Glycol Monomethyl Oligomers

The following description refers to the scheme illustrated in FIG. 8. A solution of toluene containing 20% phosgene (100 ml, approximately 18.7 g, 189 mmol phosgene) was chilled to 0° C. under a $N_2$ atmosphere. Non-polydispersed mTEG (triethylene glycol, monomethyl ether, 7.8 g, 47.5 mmol) was dissolved in 25 mL anhydrous ethyl acetate and added to the chilled phosgene solution. The mixture was stirred for one hour at 0° C., then allowed to warm to room temperature and stirred for another two and one half hours. The remaining phosgene, ethyl acetate and toluene were removed via vacuum distillation to leave the non-polydispersed mTEG chloroformate 46 as a clear oily residue.

The non-polydispersed residue 46 was dissolved in 50 mL of dry dichloromethane to which was added TEA (triethyleamine, 6.62 mL, 47.5 mmol) and NHS (N-hydroxysuccinimide, 5.8 g, 50.4 mmol). The mixture was stirred at room temperature under a dry atmosphere for twenty hours during which time a large amount of white precipitate appeared. The mixture was filtered to remove this precipitate and concentrated in vacuo. The resultant oil 47 was taken up in dichloromethane and washed twice with cold deionized water, twice with 1N HCl and once with brine. The organics were dried over $MgSO_4$, filtered and concentrated to provide the non-polydispersed title compound as a clear, light yellow oil. If necessary, the NHS ester could be further purified by flash chromatography on silica gel using EtOAc as the elutant.

Example 39

Synthesis of Activated Palmitate-TEG Oligomers

The following description refers to the scheme illustrated in FIG. 9. Non-polydispersed palmitic anhydride (5 g; 10 mmol) was dissolved in dry THF (20 mL) and stirred at room temperature. To the stirring solution, 3 mol excess of pyridine was added followed by non-polydispersed triethylene glycol (1.4 mL). The reaction mixture was stirred for 1 hour (progress of the reaction was monitored by TLC; ethyl acetate-chloroform; 3:7). At the end of the reaction, THF was removed and the product was mixed with 10% $H_2SO_4$ acid and extracted ethyl acetate (3×30 mL). The combined extract was washed sequentially with water, brine, dried over $MgSO_4$, and evaporated to give non-polydispersed product 48. A solution of N,N'-disuccinimidyl carbonate (3 mmol) in DMF (~10 mL) is added to a solution of the non-polydispersed product 48 (1 mmol) in 10 mL of anydrous DMF while stirring. Sodium hydride (3 mmol) is added slowly to the reaction mixture. The reaction mixture is stirred for several hours (e.g., 5 hours). Diethyl ether is added to precipitate the activated oligomer. This process is repeated 3 times and the product is finally dried.

Example 40

Synthesis of Activated Hexaethylene Glycol Monomethyl Oligomers

The following description refers to the scheme illustrated in FIG. 10. Non-polydispersed activated hexaethylene glycol monomethyl ether was prepared analogously to that of non-polydispersed triethylene glycol in Example 39 above. A 20% phosgene in toluene solution (35 mL, 6.66 g, 67.4 mmol phosgene) was chilled under a $N_2$ atmosphere in an ice/salt water bath. Non-polydispersed hexaethylene glycol 50 (1.85 mL, 2.0 g, 6.74 mmol) was dissolved in 5 mL anhydrous EtOAc and added to the phosgene solution via syringe. The reaction mixture was kept stirring in the ice bath for one hour, removed and stirred a further 2.5 hours at room temperature. The phosgene, EtOAc, and toluene were removed by vacuum distillation, leaving non-polydispersed compound 51 as a clear, oily residue.

The non-polydispersed residue 51 was dissolved in 20 mL dry dichloromethane and placed under a dry, inert atmosphere. Triethylamine (0.94 mL, 0.68 g, 6.7 mmol) and then NHS (N-hydroxy succinimide, 0.82 g, 7.1 mmol) were added, and the reaction mixture was stirred at room temperature for 18 hours. The mixture was filtered through silica gel to remove the white precipitate and concentrated in vacuo. The residue was taken up in dichloromethane and washed twice with cold water, twice with 1 N HCl and once with brine. The organics were dried over $Na_2SO_4$, filtered and concentrated. Final purification was done via flash chromatography (silica gel, EtOAc) to obtain the UV active non-polydispersed NHS ester 52.

Example 41

150 mg of salmon calcitonin (MW 3432, 0.043 mmol) was dissolved in 30 ml of anhydrous DMF. Then TEA (35 µL) and the activated oligomer of Example 24 (42 mg, 0.067 mmol) in anhydrous THF (2 mL) was added. The reaction was stirred for 1 hour, then quenched with 2 mL of 0.1% TFA in water. The reaction was followed by HPLC. Then the reaction mixture was concentrated and purified by prep. HPLC (RC Vydac C18 Protein and peptide, 1×25 column, water/acetonitrile with 0.1% TFA, detection at 280 nm). Two peaks, corresponding to mono- and di-conjugate were isolated. Samples were analyzed by MALDI-MS. MS for PEG7-octyl-sCT, mono-conjugate: 3897. MS for PEG7-octyl-sCT, di-conjugate: 4361.

Example 42

The procedure of Example 41 was used to conjugate salmon calcitonin with the activated oligomer of Example 29. MS for PEG7-decyl-sCT, mono-conjugate: 3926. MS for PEG7-decyl-sCT, di-conjugate: 4420.

Example 43

The procedure of Example 41 was used to conjugate salmon calcitonin with the activated oligomer of Example 31. MS for stearate-PEG6-sCT, mono-conjugate: 4006. MS for stearate-PEG6-sCT, di-conjugate: 4582.

Example 44

The procedure of Example 41 was used to conjugate salmon calcitonin with the activated oligomer of Example 37. MS for stearate-PEG8-sCT, mono-conjugate: 4095.

Example 45

The procedure of Example 41 is used to conjugate salmon calcitonin with the activated oligomer of Example 18.

Example 46

The procedure of Example 41 is used to conjugate salmon calcitonin with the activated oligomer of Example 38.

Example 47

The procedure of Example 41 is used to conjugate salmon calcitonin with the activated oligomer of Example 39.

Example 48

The procedure of Example 41 is used to conjugate salmon calcitonin with the activated oligomer of Example 40.

Example 49

Determination of the Dispersity Coefficient for a Mixture of Salmon Calcitonin-Oligomer Conjugates The dispersity coefficient of a mixture of salmon calcitonin-oligomer conjugates is determined as follows. A mixture of salmon calcitonin-oligomer conjugates is provided, for example as described above in Example 41. A first sample of the mixture is purified via HPLC to separate and isolate the various salmon calcitonin-oligomer conjugates in the sample. Assuming that each isolated fraction contains a purely monodispersed mixture of conjugates, "n" is equal to the number of fractions collected. The mixture may include one or more of the following conjugates, which are described by stating the conjugation position followed by the degree of conjugation: $Lys^{11}$ monoconjugate; $Lys^{18}$ monoconjugate; N-terminus monoconjugate; $Lys^{11,18}$ diconjugate; $Lys^{11}$, N-terminus diconjugate; $Lys^{18}$, N-terminus diconjugate; and/or $Lys^{11,18}$, N-terminus triconjugate. Each isolated fraction of the mixture is analyzed via mass spectroscopy to determine the mass of the fraction, which allows each isolated fraction to be categorized as a mono-, di-, or tri-conjugate and provides a value for the variable "$M_i$" for each conjugate in the sample.

A second sample of the mixture is analyzed via HPLC to provide an HPLC trace. Assuming that the molar absorptivity does not change as a result of the conjugation, the weight percent of a particular conjugate in the mixture is provided by the area under the peak of the HPLC trace corresponding to the particular conjugate as a percentage of the total area under all peaks of the HPLC trace. The sample is collected and lyophilized to dryness to determine the anhydrous gram weight of the sample. The gram weight of the sample is multiplied by the weight percent of each component in the sample to determine the gram weight of each conjugate in the sample. The variable "$N_i$" is determined for a particular conjugate (the $i^{th}$ conjugate) by dividing the gram weight of the particular conjugate in the sample by the mass of the particular conjugate and multiplying the quotient by Avagadro's number ($6.02205 \times 10^{23}$ $moles^{-1}$), $M_i$, determined above, to give the number of molecules of the particular conjugate, $N_i$, in the sample. The dispersity coefficient is then calculated using n, $M_i$ as determined for each conjugate, and $N_i$ as determined for each conjugate.

Example 50

Cytosensor® Studies

Figure 14:
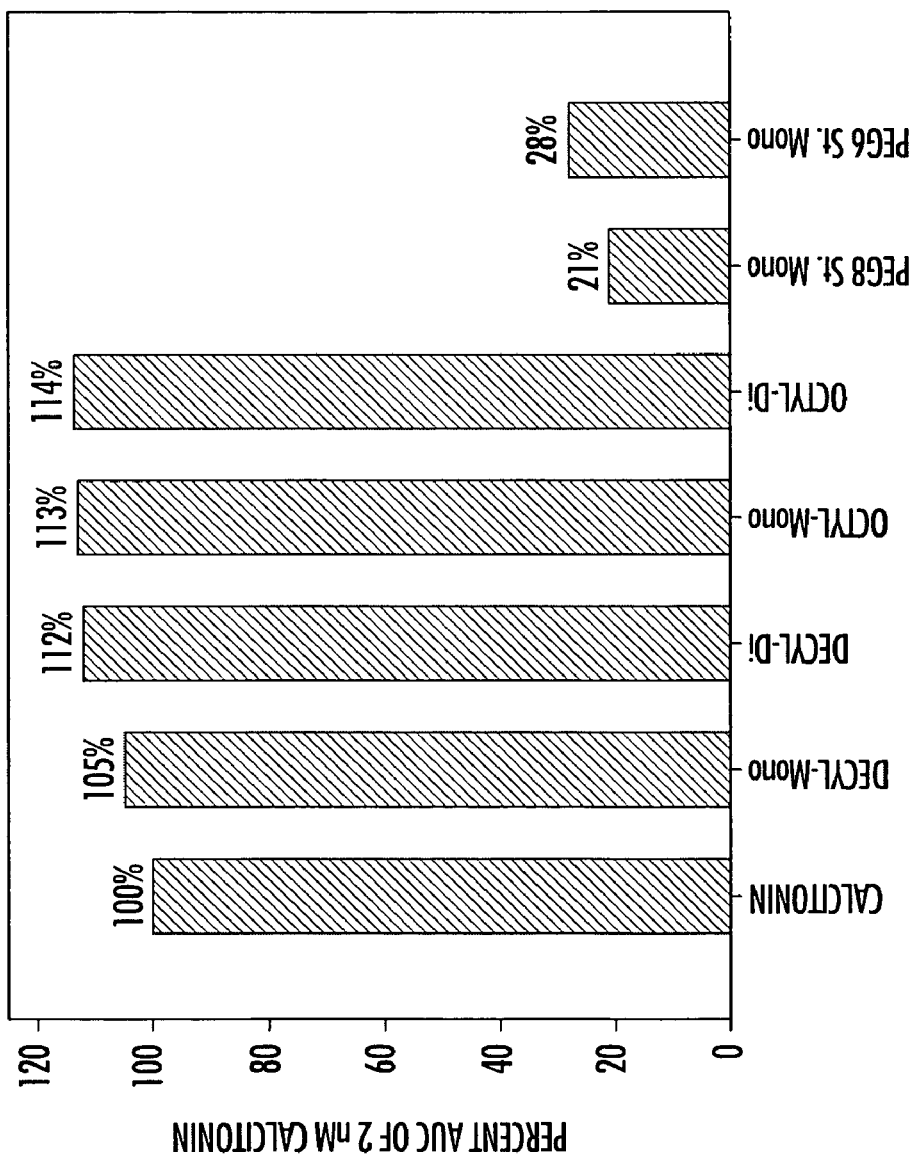
FIG. 14 illustrates a comparison of the average AUCs for various mixtures of calcitonin-oligomer conjugates according to embodiments of the present invention with non-conjugated calcitonin, which is provided for comparison purposes only and does not form part of the invention.
Figure 15:
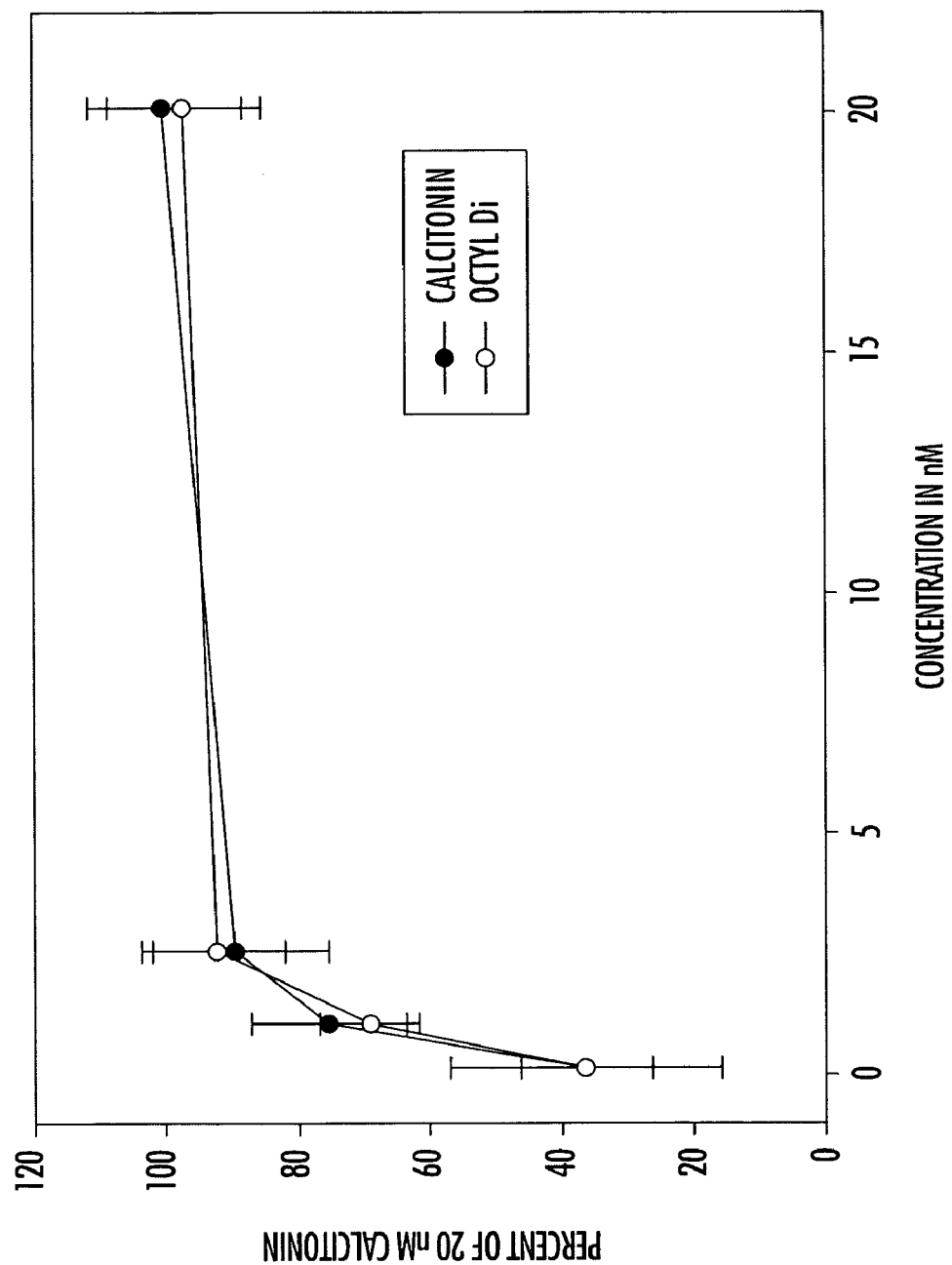
FIG. 15 illustrates a dose-response curve for a mixture of mPEG7-octyl-calcitonin diconjugates according to embodiments of the present invention compared with a dose-response curve for calcitonin, which is provided for comparison purposes and is not a part of the present invention.
Figure 16:
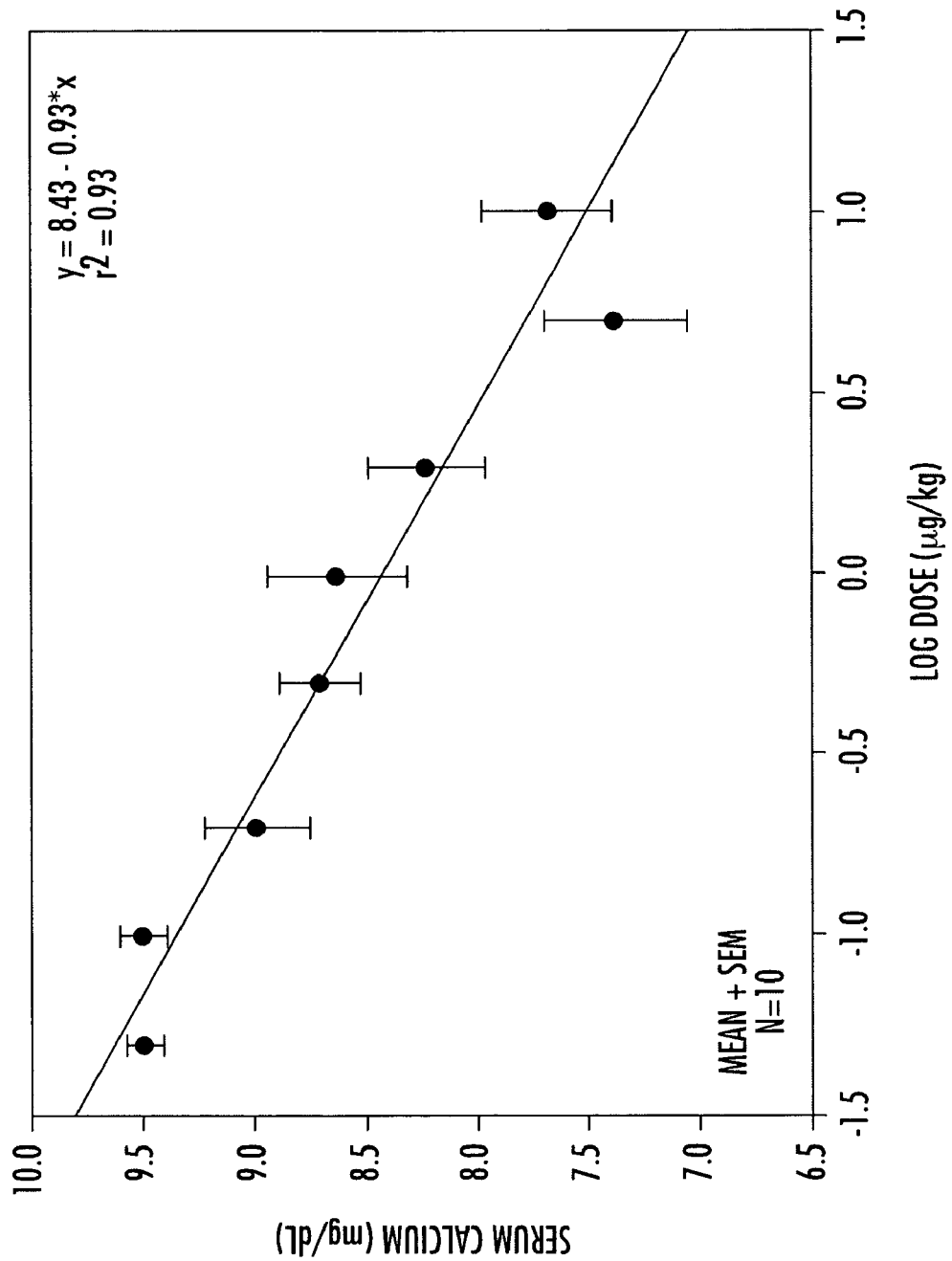
FIG. 16 illustrates a dose-response curve after oral administration of a mixture of mPEG7-octyl-calcitonin diconjugates according to embodiments of the present invention.
Figure 17:
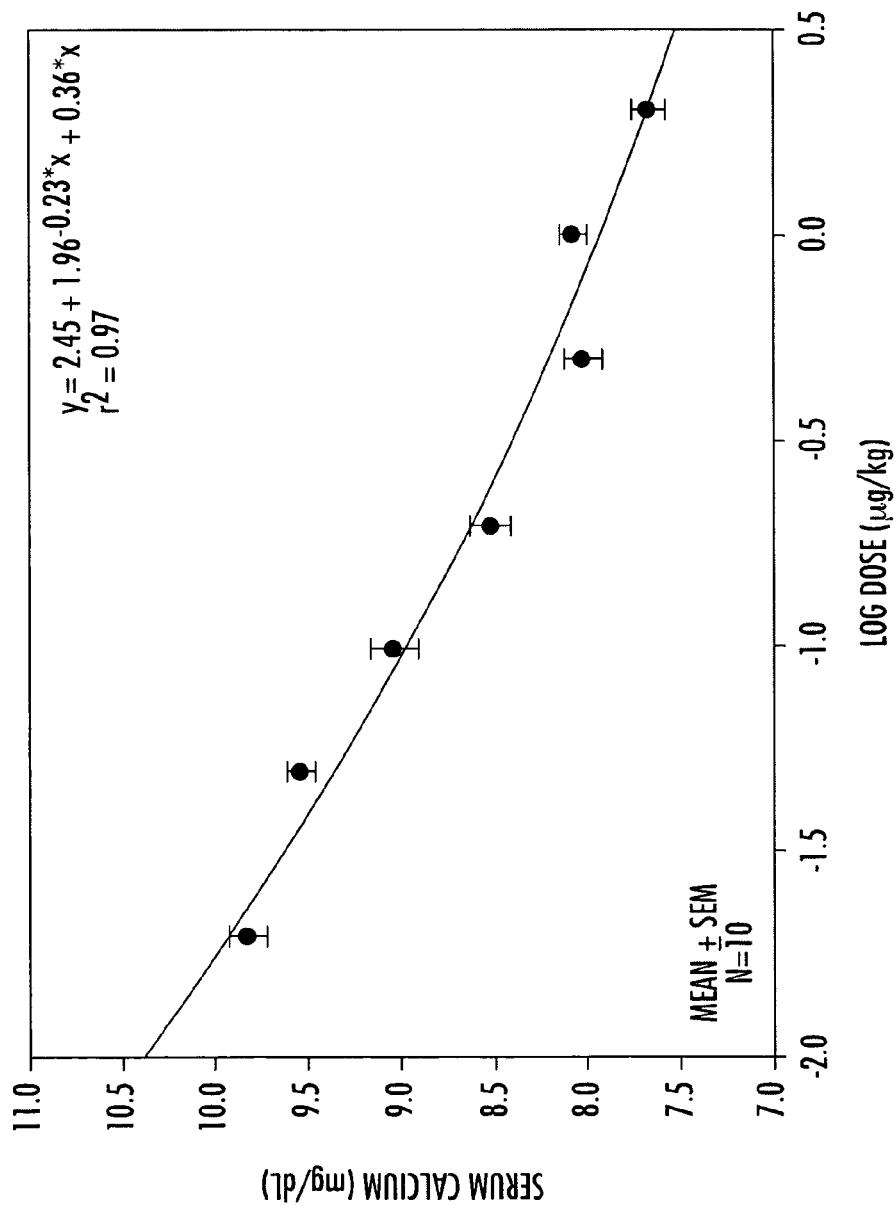
FIG. 17 illustrates a dose-response curve after subcutaneous administration of a mixture of mPEG7-octyl-calcitonin diconjugates according to embodiments of the present invention.
Figure 18:
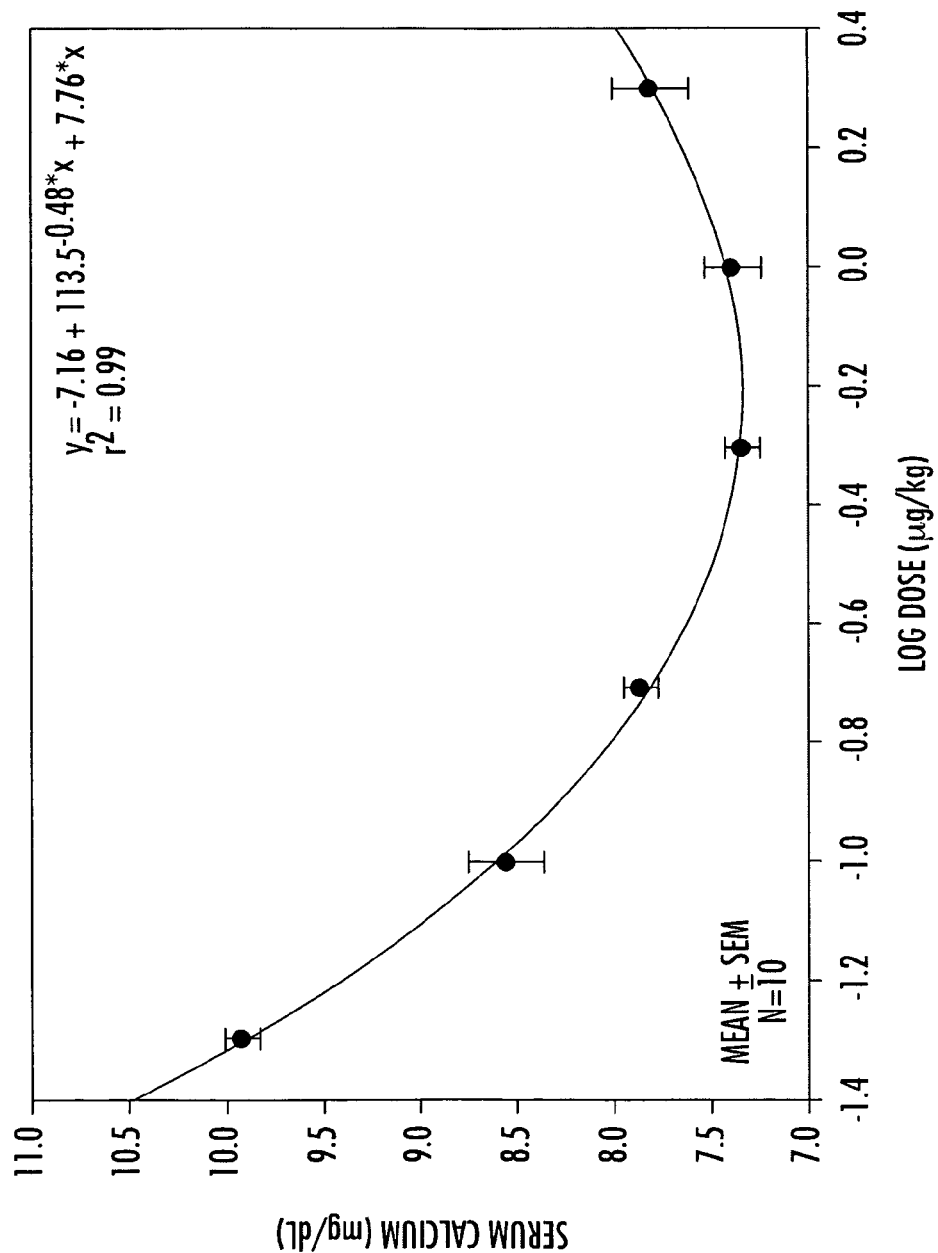
FIG. 18 illustrates a dose-response curve after subcutaneous administration of salmon calcitonin, which is provided for comparison purposes and is not part of the present invention.

T-47D cells (mammary ductal carcinoma cell line, obtained from American Type Culture Collection were suspended at a density of $1\times10^7$ cells/mL in running buffer (low-buffered, serum-free, bicarbonate-free RPMI 1640 medium from Molecular Devices of Sunnyvale, Calif. Approximately 100,000 cells were then immobilized in an agarose cell entrapment medium in a 10 μL droplet and sandwiched between two 3-μm polycarbonate membranes in a cytosensor capsule cup. Cytosensor capsule cups placed in sensor chambers on the Cytosensor® Microphysiometer were then held in very close proximity to pH-sensitive detectors. Running buffer was then pumped across the cells at a rate of 100 μL/min except during 30-second intervals when the flow was stopped, and acidification of the running buffer in the sensor chamber was measured. Acidification rates were determined every 2 minutes. The temperature of the sensor chambers was 37° C. Cells were allowed to equilibrate in the sensor chambers for 2–3 hours prior to the start of the experiment during which time basal acidification rates were monitored. Cells were then exposed to test compounds (Salmon Calcitonin or Octyl-Di-Calcitonin) diluted in running buffer at various nM concentration. Exposure of cells to test compounds occurred for the first 40 seconds of each 2 minute pump cycle in a repeating pattern for a total of 20 minutes. This allowed sufficient exposure of the cells to the test compounds to elicit a receptor-mediated response in cellular metabolism followed by approximately 50 seconds of flow of the running buffer containing no compounds. This procedure rinsed away test solutions (which had a slightly lower pH than running buffer alone) from the sensor chamber before measuring the acidification rate. Thus, the acidification rates were solely a measure of cellular activity. A similar procedure was used to obtain data for PEG7-octyl-sCT, monoconjugate (Octyl-Mono); PEG7-decyl-sCT, monoconjugate (Decyl-Mono); PEG7-decyl-sCT, diconjugate (Decyl-Di); stearate-PEG6-sCT, monoconjugate (PEG6 St. Mono); and stearate-PEG8-sCT, monoconjugate (PEG8 St. Mono). Data was analyzed for relative activity of compounds by calculating the Area Under the Curve (AUC) for each cytosensor chamber acidification rate graph and plotted as a bar chart illustrated in FIG. 14 showing average AUC measurements taken from multiple experiments performed under the same experimental conditions.

Example 51

Enzymatic Stability

Compounds, supplied as lyophilized powders, are resuspended in 10 mM phosphate buffer pH 7.4 and then submitted for concentration determination by HPLC. The phosphate buffer is used to create a solution with a pH that is optimum for activity of each particular gut enzyme. Aliquots of the compound thus prepared are transferred to 1.7 mL microcentrifuge tubes and shaken in a 37° C. water bath for 15 minutes to allow compounds to equilibrate to temperature. After 15 minutes, 2 μL of the appropriate concentrated gut enzyme is added to each tube to achieve the final concentration desired. Chymotrypsin and trypsin are resuspended in 1 mM HCl. Also, as a control, compounds are treated with 2 μL of 1 mM HCl. Immediately following additions, 100 μL of sample is removed from the control tube and quenched with either 25 μL of chymotrypsin/trypsin quenching solution (1:11% TFA:Isopropanol). This sample will serve as T=0 min. A sampling procedure is repeated at various time intervals depending on the gut enzyme used. Chymotrypsin has 15, 30 and 60 minute samples. Trypsin has 30, 60, 120 and 180 minute samples. Once all points have been acquired, a final sample is removed from the control tube to make sure that observed degradation is not temperature or buffer related. The chymotrypsin and trypsin samples may be collected directly into HPLC vials. RP-HPLC (acetonitrile gradient) is used to determine AUC for each sample and % degradation is calculated based from the T=0 min control. The results are provided below in Tables 1 to 4.

TABLE 1

% Remaining Following 0.5 U/mL Chymotrypsin Digest of PEG7-Octyl-Salmon Calcitonin, Diconjugate

| Time | Non-Formulated | | | | Buffered Formulation | | |
|---|---|---|---|---|---|---|---|
| 15 | 63 | 71 | 68 | 69 | 88 | 86 | 88 |
| 30 | 34 | 48 | 50 | 46 | 73 | 88 | 86 |
| 60 | 6 | 15 | 20 | 15 | 61 | 69 | 84 |
| | Control | | | | Control | | |
| 60 | 104 | 88 | 97 | 103 | 116 | 104 | 101 |

TABLE 2

% Remaining Following 0.5 U/mL Chymotrypsin Digest of Salmon Calcitonin (for comparison purposes; not part of the invention)

| Time | Non-Formulated | | | | Buffered Formulation | | |
|---|---|---|---|---|---|---|---|
| 10 | 73 | | | | | | |
| 15 | — | 55 | 62 | 35 | 66 | 59 | 91 | 92 |
| 30 | 30 | 26 | 40 | 13 | 42 | 54 | 86 | 87 |
| 60 | 1.6 | 5 | 12 | 1 | 12 | 55 | 82 | 85 |
| | Control | | | | Control | | |
| 60 | — | 100 | 93 | 45 | 100 | 102 | 98 | 103 |

TABLE 3

% Remaining following 1 U/mL Trypsin Digest of PEG7-Octyl-Salmon Calcitonin, Diconjugate

| Time | Non-Formulated | | | |
|---|---|---|---|---|
| 30 | 87 | 89 | 83 | 90 |
| 60 | 78 | 86 | 76 | 85 |
| 120 | 72 | 82 | 68 | 78 |
| 180 | — | 81 | 61 | 73 |
| | Control | | | |
| 60 | | 103 | 100 | |
| 120 | 106 | 105 | 99 | |
| 180 | | 104 | 99 | |

TABLE 4

% Remaining following 1 U/mL Trypsin Digest of Salmon Calcitonin (for comparison purposes; not part of the invention)

| Time | Non-Formulated | | | |
|---|---|---|---|---|
| 30 | 80 | 50 | 82 | 87 |
| 60 | 66 | 28 | 69 | 76 |
| 120 | 44 | 7 | 46 | 59 |
| 180 | — | 2 | 31 | 46 |
| | Control | | | |
| 60 | | 41 | 101 | |
| 120 | 69 | 16 | 102 | |
| 180 | | 7 | 101 | |

Example 52

Activity and Inter-Subject Variability

Male CF-1 mice (Charles River, Raleigh, N.C.) weighing 20–25 g were housed in the Nobex vivarium in a light- (L:D cycle of 12:12, lights on at 0600 h), temperature- (21–23° C.), and humidity-(40–60% relative humidity) controlled room. Animals were permitted free access to laboratory chow (PMI Nutrition) and tap water. Mice were allowed to acclimate to housing conditions for 48–72 hours prior to the day of experiment.

Prior to dosing, mice were fasted overnight and water was provided ad libitum. Mice were randomly distributed into groups of five animals per time point and were administered a single oral dose of a PEG7-octyl-sCT, diconjugate (Octyl Di) according to the present invention or salmon calcitonin (sCT or Calcitonin) for comparison purposes. Oral doses were administered using a gavaging needle (Popper #18, 5 cm from hub to bevel) at 10 mL/kg in the following 0.2 µg/mL phosphate-buffered PEG7-octyl-sCT, diconjugate, formulation:

| Ingredient | Amount |
|---|---|
| PEG7-octyl-sCT, diconjugate | 20 µg |
| Sodium-cholate | 2.5 g |
| Sodium-deoxy-cholate | 2.5 g |
| Sodium phosphate buffer, 100 mM, pH 7.4 | q.s. to 100 g |

The buffered formulation was prepared by adding 80 mL of phosphate buffer in a clean tared glass beaker. The sodium cholate was slowly added to the phosphate buffer with stirring until dissolved. The deoxy cholate was then added and stirring was continued until dissolved. The PEG7-octyl-sCT, diconjugate, solution equivalent to 20 µg was added. Finally, the remaining phosphate buffer was added to achieve a final weight of 100 g. Vehicle-control mice were used in all experiments. Dose-response curves were constructed using a single time point 60 minutes after drug administration. These curves are illustrated in FIGS. 15–18.

At appropriate time points, mice were ether-anesthetized, the vena cavae exteriorized, and blood samples were obtained via a syringe fitted with a 25-gauge needle. Blood aliquots were allowed to clot at 22° C. for 1 hour, and the sera removed and pipetted into a clean receptacle. Total serum calcium was determined for each animal using a calibrated Vitros DT60 II analyzer.

Serum calcium data were plotted and pharmacokinetic parameters determined via curve-fitting techniques using SigmaPlot software (Version 4.1). Means and standard deviations (or standard errors) were calculated and plotted to determine effect differences among dosing groups. Average serum calcium data for various conjugates are provided in Table 5 below.

TABLE 5

| Conjugate | Dispersity | % Baseline Calcium Drop at 2.0 µg/kg dose |
|---|---|---|
| PEG7-Octyl-sCT, diconjugate | Monodispersed mixture | 21.0 |
| Stearate-PEG6-sCT, diconjugate | Monodispersed mixture | 16.0 |
| PEG7-Decyl-sCT, monoconjugate | Monodispersed mixture | 11.5 |
| Stearate-PEG8-sCT, diconjugate | Monodispersed mixture | 11.0 |
| PEG7-Decyl-sCT, diconjugate | Monodispersed mixture | 8.3 |

Despite an in vitro activity as determined in Example 50 above that may not be comparable with the in vitro activity of PEG7-octyl-sCT and PEG7-decyl-sCT mono- and di-conjugates, the stearate-PEG6-sCT, diconjugate, and stearate-PEG8-sCT, diconjugate, appear to have in vivo activity (as evidenced by the drops in % baseline calcium from Table 5 above) that are comparable with the in vivo activity observed for the PEG7-octyl-sCT and PEG7-decyl-sCT, mono- and di-conjugates. While not wanting to be bound by a particular theory, the improved in vivo activity of the stearate containing conjugates may indicate that these conjugates are undergoing hydrolysis in vivo to provide an active salmon calcitonin or active salmon calcitonin-PEG conjugate.

In the specification, there has been disclosed typical preferred embodiments of the invention and, although specific terms are employed, they are used in a generic and descriptive sense only and not for purposes of limitation, the scope of the invention being set forth in the following claims.

What is claimed is:

1. A mixture of conjugates, wherein each conjugate consists of a calcitonin and a polyethylene glycol moiety, wherein the polyethylene glycol moiety is coupled to an amine function of the calcitonin, wherein the mixture is a monodispersed mixture, a substantially purely monodispersed mixture or a purely monodispersed mixture.

2. The mixture according to claim 1, wherein the polyethylene glycol moiety has at least 2 polyethylene glycol subunits.

3. The mixture according to claim 1, wherein the conjugates have the capability of lowering serum calcium levels by at least 5 percent.

4. The mixture according to claim 1, wherein the conjugates have an increased resistance to degradation by chymotrypsin or trypsin when compared to the resistance to degradation by chymotrypsin or trypsin of the calcitonin which is not coupled to the polyethylene glycol moiety.

5. The mixture according to claim 1, wherein the conjugates have a bioefficacy that is greater than the bioefficacy of the calcitonin which is not coupled to the oligomer.

6. The mixture according to claim 1, wherein the calcitonin is covalently coupled to the polyethylene glycol moiety by a hydrolyzable bond, a non-hydrolyzable bond or both.

7. The mixture according to claim 1, wherein the calcitonin is covalently coupled to the polyethylene glycol moiety.

8. The mixture according to claim 1, wherein each the polyethylene glycol moiety has the same molecular structure.

9. The mixture according to claim 1, wherein the conjugates are each amphihically balanced such that each conjugate is aqueously soluble to penetrate biological membranes.

10. A composition comprising:
    the mixture according to claim 1; and
    a pharmaceutically acceptable carrier.

11. A method of treating a bone disorder in a subject in need of such treatment, said method comprising administering an effective amount of a mixture of conjugates according to claim 1 to the subject to treat the bone disorder.

12. The method according to claim 11, wherein the bone disorder is osteoporosis Paget's disease, or hypercalcemia.

13. A monodispersed mixture of conjugates, wherein each conjugate consists of a calcitonin coupled to at least one polyethylene glycol moiety consisting of at least 4 polyethylene glycol subunits, wherein coupling between the calcitonin and the polyethylene glycol moiety-consists of an amine bond(s), said mixture having a molecular weight distribution with a standard deviation of less than about 22 Daltons.

14. A mixture of conjugates wherein each conjugate consists of a calcitonin coupled to at least one polyethylene glycol moiety, wherein coupling between the calcitonin and the polyethylene glycol moiety consists of an amine bond(s), wherein the mixture has a dispersity coefficient (DC) greater than 10,000 where $$DC = \frac{\left(\sum_{i=1}^{n} N_i M_i\right)^2}{\sum_{i=1}^{n} N_i M_i^2 \sum_{i=1}^{n} N_i - \left(\sum_{i=1}^{n} N_i M_i\right)^2}$$

wherein:
    n is the number of different molecules in the sample;
    $N_i$ is the number of $i^{th}$ molecules in the sample; and
    $M_i$ is the mass of the $i^{th}$ molecule.

15. The mixture of conjugates according to claim 14, wherein the dispersity coefficient is greater than 100,000.

* * * * *

UNITED STATES PATENT AND TRADEMARK OFFICE
CERTIFICATE OF CORRECTION

PATENT NO.        : 7,084,121 B2                                          Page 1 of 1
APPLICATION NO. : 10/806523
DATED             : August 1, 2006
INVENTOR(S)       : Ekwuribe et al.

It is certified that error appears in the above-identified patent and that said Letters Patent is hereby corrected as shown below:

Column 2, Line 65: "$Lys^{18}$" should be --$Lys^{11}$--

Column 7, Line 18: "within +1 of" should be --within ±1 of--

Column 50, Line 8: "halide?" should be --halide,--

Column 61, Line 65: "$0.8^54$ g" should be --0.854 g--

Signed and Sealed this

Twenty-third Day of October, 2007

JON W. DUDAS
*Director of the United States Patent and Trademark Office*